(12) United States Patent
Finley et al.

(10) Patent No.: US 10,806,707 B2
(45) Date of Patent: Oct. 20, 2020

(54) CANNABIS OIL COMPOSITIONS AND METHODS FOR PREPARATION THEREOF

(71) Applicant: Constance Therapeutics, Inc., San Francisco, CA (US)

(72) Inventors: Constance Finley, San Francisco, CA (US); Haley Poole Bestwick, Newberg, OR (US)

(73) Assignee: Constance Therapeutics, Inc., San Francisco, CA (US)

( * ) Notice: Subject to any disclaimer, the term of this patent is extended or adjusted under 35 U.S.C. 154(b) by 79 days.

(21) Appl. No.: 15/778,192

(22) PCT Filed: Nov. 23, 2016

(86) PCT No.: PCT/US2016/063662
§ 371 (c)(1),
(2) Date: May 22, 2018

(87) PCT Pub. No.: WO2017/091764
PCT Pub. Date: Jun. 1, 2017

(65) Prior Publication Data
US 2018/0344661 A1    Dec. 6, 2018

Related U.S. Application Data

(60) Provisional application No. 62/259,549, filed on Nov. 24, 2015.

(51) Int. Cl.
| A61K 36/00 | (2006.01) |
| A61K 31/05 | (2006.01) |
| A61K 31/192 | (2006.01) |
| A61K 31/355 | (2006.01) |
| A61K 36/185 | (2006.01) |
| A61K 31/352 | (2006.01) |
| A61P 35/00 | (2006.01) |

(52) U.S. Cl.
CPC ............ *A61K 31/05* (2013.01); *A61K 31/192* (2013.01); *A61K 31/352* (2013.01); *A61K 31/355* (2013.01); *A61K 36/185* (2013.01); *A61P 35/00* (2018.01); *A61K 2300/00* (2013.01)

(58) Field of Classification Search
CPC ....................................................... A61K 36/00
USPC ......................................................... 424/725
See application file for complete search history.

(56) References Cited

U.S. PATENT DOCUMENTS

| 6,079,418 | A | 6/2000 | Russo |
| 6,383,513 | B1 | 5/2002 | Watts et al. |
| 7,344,736 | B2 | 3/2008 | Whittle et al. |
| 7,887,857 | B1 | 2/2011 | Johnson |
| 8,445,034 | B1 | 5/2013 | Coles, Jr. |
| 8,632,825 | B2 | 1/2014 | Velasco Diez et al. |
| 8,906,429 | B1 | 12/2014 | Kolsky |
| 9,034,395 | B2 | 5/2015 | Whittle et al. |
| 9,066,920 | B2 | 6/2015 | Whalley et al. |
| 2003/0017213 | A1 | 1/2003 | Schmidt |
| 2003/0134018 | A1 | 7/2003 | Turner et al. |
| 2005/0123635 | A1 | 6/2005 | McAughey et al. |
| 2008/0167483 | A1 | 7/2008 | Whittle et al. |
| 2010/0166891 | A1 | 7/2010 | Schmidt |
| 2010/0249223 | A1 | 9/2010 | Di Marzo et al. |
| 2011/0086113 | A1 | 4/2011 | Velasco Diez et al. |
| 2012/0004251 | A1 | 1/2012 | Whalley et al. |
| 2012/0059062 | A1 | 3/2012 | Whittle et al. |
| 2013/0059018 | A1 | 3/2013 | Parolaro et al. |
| 2014/0221469 | A1 | 8/2014 | Ross et al. |
| 2014/0243405 | A1 | 8/2014 | Whalley et al. |
| 2014/0271940 | A1 | 9/2014 | Wurzer |
| 2014/0302185 | A1 | 10/2014 | Cavalieri Manasse |
| 2014/0330030 | A1 | 11/2014 | Ferri |
| 2015/0053742 | A1 | 2/2015 | Koren et al. |
| 2015/0086653 | A1 | 3/2015 | Parolaro et al. |
| 2015/0105455 | A1 | 4/2015 | Bjorncrantz |
| 2015/0105569 | A1 | 4/2015 | Emo |
| 2015/0136158 | A1 | 5/2015 | Stevens et al. |
| 2015/0245991 | A1 | 9/2015 | Nihart |
| 2015/0297654 | A1 | 10/2015 | Speier |

(Continued)

FOREIGN PATENT DOCUMENTS

| CA | 2582289 | 10/2014 |
| CN | 103005427 A | 4/2013 |
| CN | 104304815 A | 1/2015 |

(Continued)

OTHER PUBLICATIONS

Cook-Mills, J.M., et al., "Two faces of vitamin E in the lung." Am. J. Respir. Crit. Care Med. 188, 279-284, 2013.

(Continued)

*Primary Examiner* — Michael V Meller
(74) *Attorney, Agent, or Firm* — Kilpatrick Townsend & Stockton LLP

(57) ABSTRACT

The present invention provides *cannabis* oil compositions, including *cannabis* oil compositions containing vitamin E, and methods for preparing the *cannabis* oil compositions. In some embodiments, the invention provides a method for preparing a *cannabis* oil composition comprising eluting cannabinoids from *cannabis* plant material with a solvent to produce an eluate; filtering the eluate with a filter to produce a filtrate; evaporating the solvent from the filtrate with a distiller to produce a distillate; and purging the distillate under conditions sufficient to remove residual solvent. In some embodiments, the method further includes mixing a quantity of vitamin E with the extract. Blended *cannabis* oil compositions containing mixtures of *cannabis* oil preparations are also described.

4 Claims, 16 Drawing Sheets

(56) References Cited

U.S. PATENT DOCUMENTS

2015/0313867 A1  11/2015  Velasco Diez et al.

FOREIGN PATENT DOCUMENTS

| GB | 2 439 393 A | 12/2007 |
|---|---|---|
| WO | 99/32107 A1 | 7/1999 |
| WO | 2012/071389 A2 | 5/2012 |
| WO | 2013/057487 A1 | 4/2013 |
| WO | 2013/068744 A2 | 5/2013 |
| WO | 2013/165251 A1 | 11/2013 |

OTHER PUBLICATIONS

Hamahata, A. et al., "γ-Tocopherol nebulization by a lipid aerosolization device improves pulmonary function in sheep with burn and smoke inhalation injury." Free Radical Biology and Medicine 45, 425-433, 2008.

Hybertson, B.M. et al., "Aerosol-administered alpha-tocopherol attenuates lung inflammation in rats given lipopolysaccharide intratracheally." Exp. Lung Res. 31, 283-294, 2005.

Morita, N., et al. "Aerosolized alpha-tocopherol ameliorates acute lung injury following combined burn and smoke inhalation injury in sheep." Shock 25, 277, 2006.

Rizvi, S., et al., "The Role of Vitamin E in Human Health and Some Diseases." Sultan Qaboos Univ Med J 14, e157-e165, 2014.

Yamamoto, Y. et al., "Nebulization with Gamma-Tocopherol Ameliorates Acute Lung Injury after Burn and Smoke Inhalation in the Ovine Model" Shock 37, 408-414, 2012.

Stark, Michael, "Marijuana Chemistry Genetics, Processing & Potency", Sep. 1, 1993, URL: https://catnews.org/FREE%20Pot%20Books/Marijuana%20Chemistry%20-%20Genetics,%20Processing,%20&%20Potency%20-%20Michael%20S tarks.pdf, retrieved Aug. 1, 2018, 206 pages.

N.N.: "Hash Oil", Aug. 1, 2018, URL: https://en.wikipedia.org/wild/Hash_oil, retrieved Aug. 1, 2018, 5 pages.

Supplementary European Search Report, dated Sep. 24, 2019, 4 pages.

Berardi, J., "All About Hemp," Precision Nutrition, 20 pgs., 2018.

Leizer, C. et al., "The Composition of Hemp Seed Oil and Its Potential as an Important Source of Nutrition," Journal of Nutraceuticals, vol. 2(4): 35-53, 2000.

International Search Report, dated Feb. 7, 2017 for International Pat. Appl. No. PCT/US2016/063662, 3 pages.

Mansouri, H. et al., "Effects of Gibberellic Acid on Primary Terpenoids and Δ9—Tetrahydrocannabinol in Cannabis sativa at Flowering Stage," Journal of Integrative Plant Biology, vol. 51(6): 553-561, 2009.

Medical Jane, Cannabis Extraction: learn about the various methods in which cannabis is extracted [online], 2016, [retrieved on Nov. 1, 2016]. Retrieved from the Internet: <URL: http://www.medicaljane.com/category/cannabis-classroom/extractions-methods/>, 7 pages.

Mediwiet, Home—Stichting Mediwiet [online], 2016, [retrieved on Nov. 1, 2016]. Retrieved from the Internet: <URL: http://www.stichtingmediwiet.nl/>, 1 page.

Romano, L. and Hazekamp, A., "Cannabis Oil: chemical evaluation of an upcoming cannabis-based medicine," Cannabinoids, 1(1):1-11, 2013.

The Chill Bud "15 Cannabis Strains High in Cannabidiol (CBD)" Aug. 2015 [online] <URL: http://thechillbud.com/15-cannabis-strains-high-in-cannabidiol-cbd/>.

CANNABIS OIL COMPOSITIONS AND METHODS FOR PREPARATION THEREOF

CROSS-REFERENCES TO RELATED APPLICATIONS

The present application is a U.S. national phase of PCT Application No. PCT/US2016/063662, filed on Nov. 23, 2016, which claims priority to U.S. Provisional Pat. Appl. No. 62/259,549, filed Nov. 24, 2015, which application is incorporated herein by reference in its entirety for all purposes.

FIELD OF TECHNOLOGY

This disclosure relates generally to *cannabis* oils and *cannabis* oil formulations, including *cannabis* oil compositions with vitamin E, and methods of preparation thereof.

BACKGROUND OF THE INVENTION

The medicinal use of oils and extracts derived from *cannabis* plant material has been growing in popularity. For example, pharmacologically active compounds in *cannabis* plant material including, but not limited to, delta-9-tetrahydrocannabinol (or THC) and cannabidiol (CBD) have been shown to reduce the effects of nausea and vomiting caused by certain chemotherapy treatments. Research has also shown the ability of cannabinoids and other compounds found in *cannabis* to stimulate bone growth, relieve pain, aid sleep, inhibit bacterial cell growth, inhibit cancer cell growth, and alleviate or otherwise reduce the symptoms of cancer, epilepsy, autoimmune disease, neurodegeneration, Alzheimer's disease, Lyme disease, post-traumatic stress disorder, and inflammation. Furthermore, extracts of *cannabis* plant material, whether ingested or inhaled, have also been shown to have therapeutic effects in patients with glaucoma, dysmenorrhea, migraines, anxiety disorders, or a combination thereof.

However, *cannabis* oil is often highly viscous, making it difficult to work with and load into new delivery devices such as vaporizers and E-cigarettes. In addition, such oils, when vaporized or smoked, are often rough on a patient's throat and may induce coughing or gagging.

Therefore, a solution is needed in order to make such extracts more conducive to today's delivery devices and make the inhalation/consumption of such extracts more palatable for patients. In addition, such a solution should also not have an adverse effect on the potency of the extract's active compounds and preserve the extract's gustatory or aromatic qualities.

BRIEF SUMMARY OF THE INVENTION

Disclosed herein are *cannabis* oil extracts, compositions containing blended mixtures of the extracts, and methods for preparing the extracts and compositions. In particular, a method is disclosed for preparing a *cannabis* oil composition comprising eluting cannabinoids from *cannabis* plant material with a solvent to produce an eluate, filtering the eluate with a filter to produce a filtrate, evaporating the solvent from the filtrate with a distiller to produce a distillate, and dehydrating/purging the distillate with a dehydrator or vacuum oven to produce an extract. In some embodiments, the method further includes mixing a quantity of vitamin E with the extract. In some embodiments, the quantity of vitamin E is sufficient to reduce the viscosity of the composition to less than 3500 cP. In some embodiments, the method includes eluting cannabinoids and terpenes from *cannabis* plant material to produce the eluate. In some embodiments, the method includes mixing the extract with essential oils.

In certain embodiments, the invention provides a composition comprising a first *cannabis* oil preparation having a first cannabinoid profile and a second *cannabis* oil preparation having a second cannabinoid profile. In some embodiments, the composition comprises $\Delta^9$-tetrahydrocannabinol (THC) and (−)-cannabidiol (CBD). In some embodiments, the ratio of THC to CBD ranges from about 20:1 to about 1:20 by weight. In some embodiments, the ratio of THC to CBD is about 4:1 by weight. In some embodiments, the composition comprises one or more additional *cannabis* oils having additional cannabinoid profiles.

The methods and compositions disclosed herein may be implemented in any means for achieving various aspects. Other features will be apparent from the accompanying drawings and from the detailed description that follows.

BRIEF DESCRIPTION OF THE DRAWINGS

Exemplary embodiments are illustrated by way of example and are not limited to the figures of the accompanying drawings, in which, like references indicate similar elements.

Figure 1A:
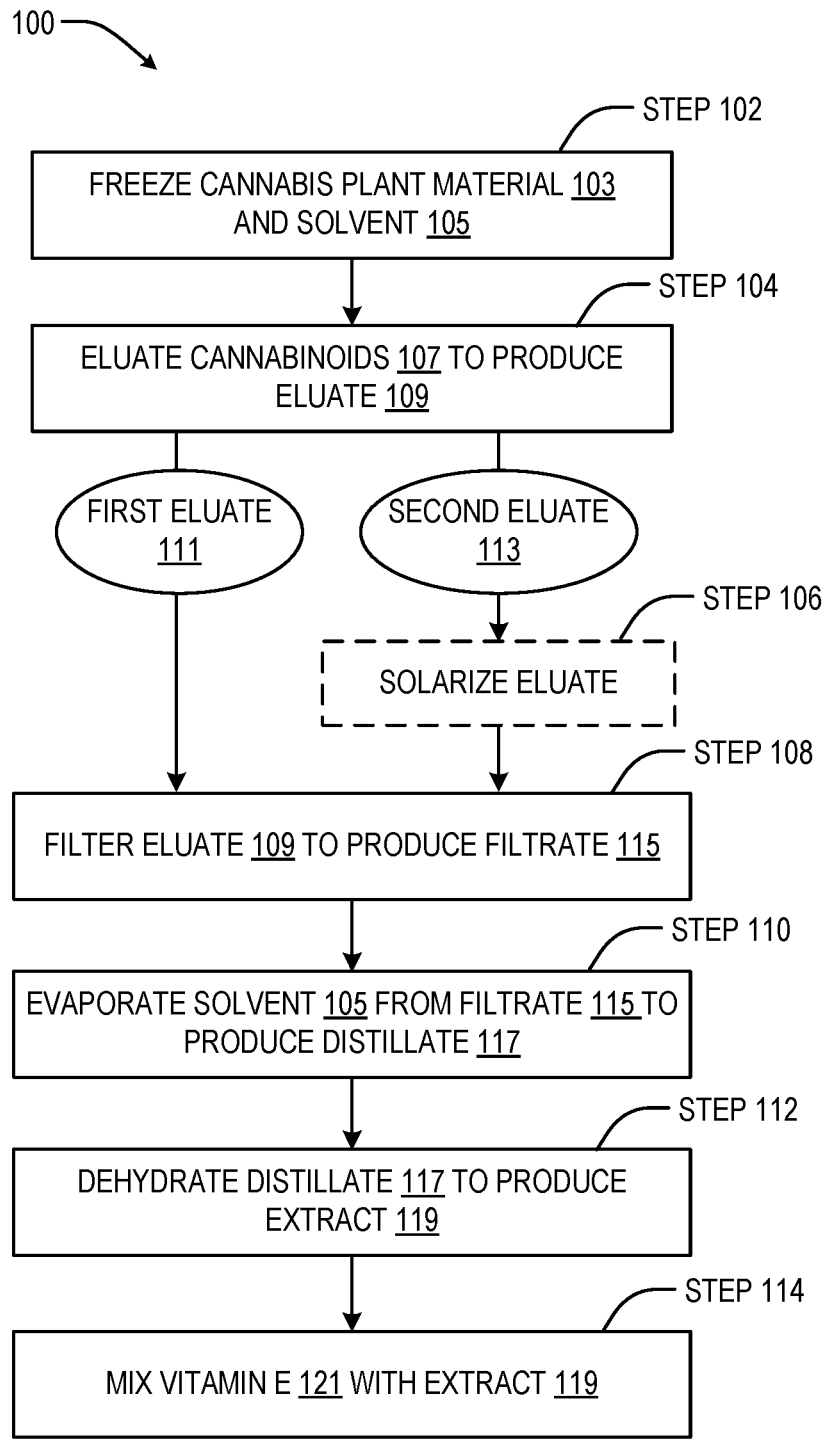
FIG. 1A shows a method of preparing a *cannabis* oil composition according to one embodiment of the invention.
Figure 1B:
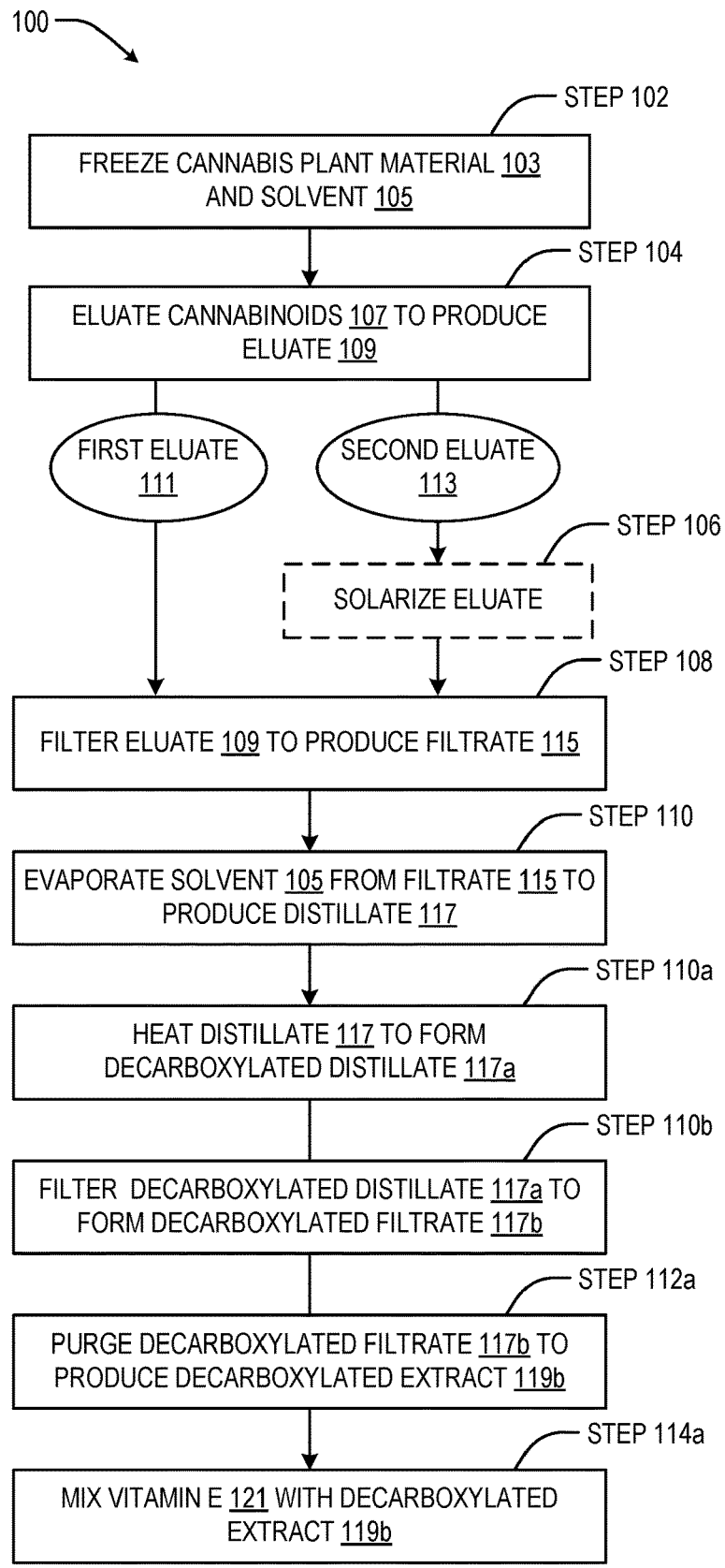
FIG. 1B shows a method of preparing a *cannabis* oil composition according to an embodiment of the invention including optional decarboxylation and filtration steps.

Other features of the present embodiments will be apparent from the accompanying drawings and from the detailed description that follows.

DETAILED DESCRIPTION OF THE INVENTION

I. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

The term "*cannabis*" refers to plants of the genus *cannabis*, including *cannabis sativa*, *cannabis indica*, and *cannabis ruderalis*.

The term "*cannabis* oil" refers to a mixture of compounds obtained from the extraction of *cannabis* plants. Such compounds include, but are not limited to, cannabinoids, terpenes, terpenoids, and other compounds found in the *cannabis* plant. The exact composition of *cannabis* oil will depend on the strain of *cannabis* that is used for extraction, the efficiency and process of the extraction itself, and any additives that might be incorporated to alter the palatability or improve administration of the *cannabis* oil.

The term "cannabinoid" refers to a chemical compound that shows direct or indirect activity at a cannabinoid receptor. There are two main cannabinoid receptors, CNR1 (also known as CB1) and CNR2 (also known as CB2). Other receptors that research suggests have cannabinoid activity include the GPR55, GPR18, and TRPV1 receptors. The term "phytocannabinoid" refers to cannabinoids that occur in a plant species or are derived from cannabinoids occurring in a plant species. Examples of cannabinoids include, but are not limited to, tetrahydrocannabinol (THC), cannabidiol (CBD), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), and cannabigerol monomethyl ether (CBGM).

The term "acidic cannabinoid" refers to a cannabinoid having one or more carboxylic acid functional groups. Examples of acidic cannabinoids include, but are not limited to, tetrahydrocannabinolic acid (THCA), cannabidiolic acid (CBDA), and cannabichromenic acid (CBC). Acidic cannabinoids are frequently the predominant cannabinoids found in raw (i.e., unprocessed) *cannabis* plant material.

The term "neutral cannabinoid" refers to a cannabinoid without carboxylic acid functional groups. Examples of neutral cannabinoids include, but are not limited to, THC, CBD, CBG, CBC, and CBN.

As used herein, the term "cannabinoid profile" refers to the number, identity, and quantity of cannabinoids in a *cannabis* oil preparation. *Cannabis* oil compositions of the invention generally contain a blend of at least two *cannabis* oil preparations having distinct cannabinoid profiles. In certain embodiments, *cannabis* oil preparations are blended to provide defined cannabinoid levels in the compositions. When a certain amount (e.g., 75%) of a particular cannabinoid (e.g., THC) is derived from a particular *cannabis* oil preparation (e.g., a first *cannabis* oil preparation), that amount of the cannabinoid is said to be "present" in the cannabinoid profile corresponding to the *cannabis* oil preparation. When 75% of the THC in a composition is said to be present in a first cannabinoid profile, for example, it is meant that 75% of the THC in the final composition is derived from a first *cannabis* oil preparation in the composition. The remaining 25% of the THC in the final composition is derived from the other *cannabis* oil preparations (e.g., a second or third *cannabis* oil preparation) in the blend. It will be appreciated that cannabinoid profiles do not remain distinct from each other, or otherwise segregated, after blending in a composition.

The term "degradation" refers to the structural and/or chemical deterioration of a substance such as chlorophyll or other plant components. Degradation can include, for example, the alteration of chemical structure, oxidation state, or metal-binding properties of the substance.

The term "eluate" refers to a solution that is collected after contacting a plant material, such as raw *cannabis* plant material, with an extraction solvent. The eluate can contain dissolved cannabinoids as well as other compounds of medicinal value.

The term "solarizing" refers to exposing an eluate to a light source. Solarizing can be achieved using natural or non-natural light sources. In some instances, the light source is used to improve the quality and/or palatability of the eluate.

The term "filtrate" refers to a solution that has passed through a membrane or strainer of variable porousness or permeability to remove either particulate matter or unwanted compounds. In the methods of the invention, an eluate is passed through a filter to produce a filtrate.

The term "distillate" refers to a solution that has been concentrated by any known means of evaporation or distillation. In the methods of the invention, the filtrate is evaporated to form the distillate.

The terms "dehydration" and "dehydrating" refer to a process of purging or otherwise removing residual solvent from the distillate. In the methods of the invention, the distillate can be dehydrated by methods including use of a vacuum pump with or without elevating the temperature.

The term "extract" refers to a solution that has been purged or dehydrated to remove residual solvent. In the methods of the invention, the extract is formed by purging or dehydrating the distillate using any known means in the art.

The terms "winterizing" and "freezing" refer to cooling an eluate from a *cannabis* plant to below ambient temperatures. In some instances, winterizing is used to remove unwanted or non-desirable compounds from the eluate. In some instances, winterizing is used to store the eluate before further processing.

The term "viscosity" is used to quantify the resistance of a substance such as a *cannabis* oil to deformation under shear stress and/or tensile stress.

The term "essential oil" refers to natural plant oil typically obtained by distillation and having a chemical composition and organoleptic properties (e.g., fragrance) characteristic of the plant or other source from which it is extracted.

The term "strain" refers to different varieties of a particular plant genus. For example, the term strain can refer to different varieties of *cannabis* plants. Different *cannabis* strains often exhibit distinct chemical compositions with characteristic levels of cannabinoids and terpenes, as well as other components. Differing cannabinoid and terpene profiles associated with different *cannabis* strains can be useful for the treatment of different diseases, or for treating different subjects with the same disease.

The term "vitamin E" refers to a group of compounds that include both tocopherols and tocotrienols including, but not limited to α-tocopherol, β-tocopherol, γ-tocopherol, δ-tocopherol, α-tocotrienol, β-tocotrienol, γ-tocotrienol, δ-tocotrienol, salts thereof, and combinations thereof. Vitamin E can be obtained from sources including, but not limited, to soybeans, sunflowers, and combinations thereof.

The terms "treat," "treating," and "treatment" refer to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom. The treatment or amelioration of symptoms can be based on any objective or subjective parameter; including, e.g., the result of a physical examination.

The terms "a," "an," or "the" as used herein include plural referents unless the context clearly dictates otherwise.

The terms "about" and "around," as used herein to modify a numerical value, indicate a close range surrounding that explicit value. If "X" were the value, "about X" or "around X" would indicate a value from 0.8× to 1.2×, preferably a value from 0.9× to 1.1×, and, more preferably, a value from 0.95× to 1.05×. Any reference to "about X" or "around X" specifically indicates at least the values X, 0.95×, 0.96×, 0.97×, 0.98×, 0.99×, 1.01×, 1.02×, 1.03×, 1.04×, and 1.05×. Thus, "about X" and "around X" are intended to teach and provide written description support for a claim limitation of, e.g., "0.98×."

II. Extraction Methods for Preparing *Cannabis* Oils

In one aspect, the present invention provides methods for preparing *cannabis* extracts and compositions containing the extracts. The method includes eluting cannabinoids from *cannabis* plant material with a solvent to produce an eluate, filtering the eluate with a filter to produce a filtrate, evaporating the solvent from the filtrate with a distiller to produce a distillate, and purging the distillate under conditions sufficient to remove residual solvent, thereby producing a *cannabis* oil extract. In certain embodiments, the eluate obtained from the *cannabis* plant material further includes one or more terpenes, terpenoids, or other plant components. In some embodiments, the method further comprises mixing a quantity of vitamin E with the extract to produce a *cannabis* oil composition. In some embodiments, the method further includes combining the *cannabis* oil or *cannabis* oil/vitamin E mixture with an essential oil or a carrier oil to produce a *cannabis* oil composition.

Reference is now made to FIG. 1A, which is a method 100 of preparing the *cannabis* oil composition according to one embodiment. The method 100 can include freezing *cannabis* plant material 103 and solvent 105 in step 102.

In some embodiments, the *cannabis* plant material 103 can be plant material from a *cannabis indica* plant. In some embodiment, the *cannabis* plant material 103 can be plant material from a *cannabis sativa* plant. In some embodiment, the *cannabis* plant material 103 can be plant material from a hybrid *cannabis indica* and *cannabis sativa* plant. In these and other embodiments, the *cannabis* plant material 103 can be fresh plant matter.

In some embodiments, the *cannabis* plant material is a strain selected from the group consisting of AC/DC, Afghan Goo, Atomic Northern Lights, Blackberry Kush, Blueberry, Blueberry Kush, Blueberry Muffin Top, Blueberry OG, Blue Diesel, Blue Dream, Buddha Passion, Cannatonic, Chocolate Kush, Fire OG, Jilly Bean, Gran Daddy Purple, Grape Blackberry Kush, Harle OG, Harle Tsu, Harlequin, Hope Springs, Infinite Euphoria, Long Valley Royal Kush, Medihaze, Pineapple Jack, Prize Kush, Sour Diesel, Sour Kush, and Tahoe OG.

In some embodiments, the *cannabis* plant material is a strain selected from the group consisting of AC/DC, Blueberry, Afghan Goo, Prize Kush, Medihaze, and Cannatonic. In a more specific embodiment, the *cannabis* plant material 103 can be a strain of *cannabis* selected from the group consisting of AC/DC, Blueberry, and Cannatonic.

Further strains and hybrid strains contemplated for use in the methods of the invention include, but are not limited to: Afgoo; Afghan Kush; Agent Orange; AK-47; Amnesia Haze; Atomic Jam; Atomic Northern Lights; Avidekel; BC Grapefruit; *Belladonna*; Berry White; Blackberry British Columbia; Blackberry Kush; Black Romulan; Black Queen; Blueberry Kush; Blueberry OG; Blue Dream; Blue Cheese; Blueberry Cheese; Blue Diesel; Blue Dream; Blue Jay Way; Blue Velvet; Boost; Bubba Kush; Bubble Gum; Buddha Passion; BW Cookies; Cadillac Purple; Canna Sue; CannaTsu; Casey Jones; Charlotte's Web; Cheese; Cheeze; Cherry AK; Cherry Cola; Cherry Pie; Chemdawg; Chem Scout; Chocolate Kush; Chocolope; Chiesel; Cinderella 99; Cotton Candy Kush; Critical Jack; Death Star; Diesel Cookies; Downtown Diesel; Double Diesel; Dream Kush; Durban Cookies; Durban Poison; Dutch Treat; Dr. Tod; Elektra; Exodus; Fern Dog; Fire OG; Frankenstein OG; G13; God's Gift; Gran Daddy Purps; Granddaddy Purple; Granny Durkel; Grape Ape; Grape Puff; Grapefruit Rom; Grapekush; Grape Blackberry Kush; Girl Scout Cookies; Green Crack; Green Goddess; Headband; Heady Kush; Harlequin; Hash Plant; Hindica; Hindu Kush; Hopesprings; Huckleberry; Hubba Bubba; Infinite Euphoria; Island Sweet Skunk; Jack Herer; Jamaican Lion; Jamaican Skunk; Jelly Bean; Jilly Bean; Kushage; LA Confidential; Larry OG; Lavender; Lemon Haze; Lemon Kush; Lemon Skunk; Liberty Haze; Lion Fire; Manawell; Mango; Mango Haze; Maplewreck; Master Kush; Maui Waui; Misty; Mr. Nice; Northern Lights; NYC Diesel; OG Afgani; OG Kush; Ol' Betsy; Orange Crush; Orange Kush; Phenom Phen; Pineapple Express; Pineapple Haze; Pineapple Jack; Pineapple Kush; Pineapple Thai; Platinum Cookies; Platinum Kush; Pomegranate Kush; Purps; Purple Diesel; Purple Goo; Purple Hash Plant; Purple Haze; Purple Jasmine; Purple Kush; Purple Nice; Purple Platinum; Purple Trainwreck; Purple Urkle; R4; Rain; Red Raspberry Kush; Romulan; Royal Cookies; Sage Diesel; Sensi Star; Sierra; Sierra Purple; Silver Diesel; Silver Dragon; Silver Haze; Skywalker; Skywalker OG; Snow Cap; Sour Boogie; Sour Diesel; Sour Kush; Sour OG; Sour Tsunami; Stinky Purple; Strawberry Cough; Sunset Sherbert; Super Lemon Haze; Super Silver Haze; Sunra; Sweetooth SFV; Tahoe OG Kush; Thin Mints; Tangerine Dream; Tora Bora; Trainwreck; Ultraviolet; Unicorn; Vanilla Kush; West Point Snow; White Erkle; White Rhino; White Russian; White Widow; and Wizard's Potion.

The *cannabis* plant material 103 can include *cannabis* flowers, buds, trichomes, leaves, stems, portions therein or combinations thereof. In some embodiments, the *cannabis* plant material consists essentially of *cannabis* buds. The buds can be whole buds or buds that are cut or broken into pieces. Step 102 can include freezing the *cannabis* plant material 103 and the solvent 105 for at least about 12 hours (e.g., about 16-24 hours). In one or more embodiments, the *cannabis* plant material and the solvent can be frozen at a temperature between about 0° C. and about −20° C. One unexpected benefit from freezing the *cannabis* plant material 103, the solvent 105, or a combination thereof is the preservation of valuable terpenes or other volatile molecules when preparing the *cannabis* oil extract. In addition, freezing the *cannabis* plant material and/or solvent can decrease the quantity of chlorophyll in the *cannabis* oils (an unwanted byproduct of the process).

In general, the plant material and/or extraction solvent are held at a particular temperature for a period of time sufficient to ensure that the materials reach the temperature. One of skill in the art will appreciate that the length of cooling or freezing time will depend in part on factors such as the targeted freezing/cooling temperature and the quantity of materials used in the method, as well as the particular extraction solvent and *cannabis* strain. Accordingly, *cannabis* plant material and/or extraction solvents are typically held for periods of time ranging from several minutes to several hours in length. For example, *cannabis* plant material and/or extraction solvents can be held at a reduced temperature for anywhere from about 10 minutes to about 72 hours prior to extraction. *Cannabis* plant material and/or extraction solvents can be held at a reduced temperature for a period of from about 30 minutes to about 48 hours, or from about 1 hour to about 36 hours, or from about 4 hours to about 24 hours, or from about 12 hours to about 18 hours prior to extraction. *Cannabis* plant material and/or extraction solvents can be held at a reduced temperature for a period of about 8, 9, 10, 11, 12, 13, 14, 15, 16, 17, or 18 hours prior to extraction. In some embodiments, *cannabis* plant material and ethanol are held at around −20° C. for around a minimum of 16 hr prior to extracting the *cannabis* plant material with the ethanol.

Typically, the materials used in the methods of the present invention are cooled to temperatures below ambient temperature (i.e., below about 25° C.) prior to and/or during the extraction step. For example, the *cannabis* plant material and/or the extraction solvent can be held at a temperature ranging from about −80° C. to about 20° C. The *cannabis* plant material and/or the extraction solvent can be held at a temperature ranging from about −80° C. to about −20° C., or from about −20° C. to about 0° C., or from about 0° C. to about 4° C., or from about 4° C. to about 20° C. In some embodiments, the *cannabis* plant material and the extraction solvent are held at about 0° C. prior to the extraction step. In some embodiments, the *cannabis* plant material and the extraction solvent are held at about −20° C. prior to the extraction step. In some embodiments, the *cannabis* plant material and the extraction solvent are held at about −23° C. prior to and/or during the extraction step.

The extraction step can be conducted at temperatures ranging from about −80° C. to about 30° C. The extraction step can be conducted, for example, at a temperature ranging from about −80° C. to about −20° C., or from about −20° C. to about 0° C., or from about 0° C. to about 4° C., or from about 4° C. to about 20° C. In some embodiments, the extraction step is conducted a temperature below about 0° C. In some embodiments, the extraction step is conducted at about −23° C. The extraction can be conducted with materials that have been frozen or chilled as described above or with materials at ambient temperatures.

The solvent 105 can be a predominantly polar solvent. In one embodiment, the solvent 105 can be an alcohol such as ethanol. The solvent 105 can also be a polar solvent derived from organic sources. In a more specific embodiment, the solvent 105 can be a 95% biodynamic ethanol. In an even more specific embodiment, the solvent 105 can be 190 proof organic grain wheat spirit. In other embodiments, the solvent 105 can include organic ethers, esters, and/or ketones. In some embodiments, the solvent can include USDA certified organic corn, grape, or cane sugar, food-grade organic alcohol, and/or biodynamic ethanol.

One of skill in the art will appreciate that a large number of organic solvents can be used for this extraction. Examples of organic solvents that can be used include, but are not limited to, acetonitrile, methanol, isopropanol, 1-butanol, 2-butanol, dichloromethane, ethyl acetate, isopropyl acetate, isopropyl ether, methyl tert-butyl ether, diethyl ether, acetone, butane, hexane, heptane, and combinations thereof. In some embodiments, isopropanol is used as the extraction solvent. In some embodiments, ethyl acetate is used as the extraction solvent. In some embodiments mixtures of organic solvents can be used to improve the extraction process.

The method 100 can also include eluting cannabinoids 107, such as THC and CBD, from the *cannabis* plant material 103 with the solvent 105 to produce an eluate 109 in step 104. In one embodiment, step 104 can include eluting the cannabinoids 107 from the *cannabis* plant material 107 frozen in step 102 with the solvent 105 also frozen from step 102 representing an eluent. The *cannabis* plant material 103 can also be referred to as a marc. The eluate 109 can also be referred to as a menstruum.

As will be discussed in more detail below, step 104 can yield a first eluate 111 and a second eluate 113. For ease of reference, both the first eluate 111 and the second eluate 113 can be referred to as the eluate 109.

In one embodiment, step 104 can include placing the *cannabis* plant material 103 in a strainer or perforated filter funnel over a collection receptacle. In a more specific embodiment, the strainer can be a colander such as a ROSLE colander and the collection receptacle can be a bucket or other type of open container. In other embodiments, the strainer can be a sieve or straining basket. In these embodiments, the *cannabis* plant material 103 frozen from step 102 can be placed in the strainer over the collection receptacle.

Step 104 can include pouring the solvent 105 representing the eluent over the *cannabis* plant material 103 placed in the strainer and collecting the eluate or menstruum from this pouring step in the collection receptacle.

Any amount of solvent suitable for extracting cannabinoids and other desired compounds can be used in the methods of the invention. For example, the ratio of extraction solvent (L) to *cannabis* plant material (lb) in the extraction step can range from about 0.1 L:1 lb to about 10 L:1 lb or more. The extraction solvent to *cannabis* plant material ratio can be from about 0.1 L:1 lb to about 1 L:1 lb, from about 1 L:1 lb to about 2 L:1 lb, from about 1 L:1 lb to about 2 L:1 lb, from about 2 L:1 lb to about 4 L:1 lb, from about 4 L:1 lb to about 8 L:1 lb. The ratio of solvent to *cannabis* plant material can also include from about 2.5:1 to about 3.5:1, from about 2.3:1 to about 3.7:1, from about 2.2:1 to about 3.8:1, from about 2:1 to about 4:1, from about 1.8:1 to about 4.2, or from about 1.5:1 to about 4.5:1. In some embodiments, the extraction solvent to *cannabis* plant material ratio in the extraction step is about 3L:1 lb.

In one embodiment, three liters of the solvent 105 can be poured over one pound of the *cannabis* plant material 103. In a more specific embodiment, the solvent 105 can be organic ethanol.

In one or more embodiments, the eluate or menstruum collected from this pouring step can be poured over the same *cannabis* plant material 103 again to elute more of the cannabinoids 107 from the *cannabis* plant material 103. This pouring step can be repeated until the *cannabis* plant material 103 has been poured over a total of three to six times, or until the coloration of the eluate or menstruum exhibits hues of green due to accumulation of chlorophyll or other undesired plant material in the eluate.

Any number of pouring steps can be used to elute the cannabinoids from the *cannabis* plant material during the extraction step. The number of pours can range from 1 to about 15 or more. For example, there can be 1, 2, 3, 4, 5, 6, 7, 8, 9, 10, 11, 12 13, 14, 15 or more pouring steps. In some embodiments, multiple pouring steps are achieved by reusing the collected eluate or menstruum of the initial pouring step. In some embodiments, multiple pouring steps are achieved by using fresh extraction solvent. In some embodiments the volume of extraction solvent is altered in different pouring steps. In some embodiments, the number of pouring steps is terminated before the eluate turns green, which color can indicate an undesirable level of chlorophyll or other undesired plant material accumulation in the eluate.

At this point, the eluate or menstruum produced by the repeated pours can be filtered to yield the first eluate 111. The eluate or menstruum produced by the repeated pours can be filtered by pouring through a mesh filter. In one embodiment, the mesh filter can be a metallic filter. In some embodiments, the mesh filter can be a membrane filter. In some embodiments, the mesh filter can be a cloth or muslin fabric filter.

The first eluate 111 can be collected in a glass or other container having a lid or other closing mechanism. In one embodiment, the glass container can be a glass jar having a jar lid. In a more specific embodiment, the glass container can be a gallon-sized glass jar. In some embodiments, the glass container can be a 2-5 L Pyrex media bottle. The glass container comprising the first eluate 111 can be closed by the lid or other closing mechanism and stored in a freezer. In one embodiment, the first eluate 111 collected in the glass container can be stored for about 24 to about 48 hours at a temperature between about 0° C. and about −20° C. After this freezing step, the first eluate 111 can undergo further filtration in step 108 below. In some embodiments, the first eluate is further subjected to solarization as described below.

Step 104 can also include using the leftover *cannabis* plant material 103 from the pouring steps above to produce the second eluate 113. Fresh portions of the solvent can be poured over *cannabis* plant material 103 in the strainer to produce the second eluate. Alternatively, the *cannabis* plant material 103 can be removed from the strainer and placed into an open container. In one embodiment, the open container can be a bucket such as a polymer-based bucket. As a more specific embodiment, the open container can be a five gallon plastic bucket. In this embodiment, fresh instances of the solvent 105 (e.g., unused solvent 105 from step 102) can be poured into the open container until the solvent 105 completely covers the *cannabis* plant material 103. The second eluate can be subjected to solarization as described below.

Step 104 can further include soaking the *cannabis* plant material 103 in the solvent 105, at or below room temperature, for about 1 to about 2 hours in the open container. In some embodiments, the plant material is left to soak without agitation. In one embodiment, the *cannabis* plant material 103 can also be macerated while soaking in the solvent 105. In this embodiment, the *cannabis* plant material 103 can be macerated by agitating the *cannabis* plant material 103 through mechanical or manual force such as by stirring the solvent 105 in the open container. The plant material can also be broken apart or ground into finer-sized particles.

The extraction solvent can be soaked with the plant material before straining or the extraction solvent can be kept separate before straining. In instances where *cannabis* plant is soaked/macerated with extraction solvent, incubation time can range from less than about 1 minute to more than about 10 hours. For example, incubation time ranges from less than 1 minute to about 10 minutes, from about 10 minutes to about 30 minutes, from about 30 minutes to about 2 hours, from about 2 hours to about 4 hours, from about 4 hours to about 7 hours, or from about 7 hours to about 10 or more hours. In some embodiments the extract and the plant material are soaked/macerated for about 2 minutes. In some embodiments, the extract and the plant material are soaked/macerated for about 2 hours. In some embodiments, the extract and the plant material are soaked/macerated for about 6 hours.

After soaking the *cannabis* plant material 103 in the solvent 105, the entire contents of the open container can be poured through a strainer, such as a ROSLE colander, and then filtered to yield the second eluate 113. The contents of the open container can be filtered using a mesh filter. In one embodiment, the mesh filter can be a metallic filter. In some embodiments, the mesh filter can be a membrane filter or a fabric (e.g., muslin) filter.

The second eluate 113 can be collected in a glass or other container (e.g., a container made of high- or low-density polyethylene) having a lid or other closing mechanism. In one embodiment, the glass container can be a glass jar having ajar lid. The second eluate 113 can be subjected to solarization in step 106 prior to further filtration in step 108 below.

Solarization is a process that includes exposing the *cannabis* extract to a light source to degrade any chlorophyll that has collected with the cannabinoids. The solarization process can be carried out for any amount of time desired. Typically, the incubation time can range from fewer than about 5 minutes to more than about 12 hours. The solarization time can depend on factors including, but not limited to, the strength of the light source used. The solarization time can be from about 5 minutes to about 30 minutes, or from about 30 minutes to about 2 hours, or from about 2 hours to about 5 hours, or from about 5 hours to about 12 hours or more. The solarization time can also depend on the desired finished product. In some embodiments, solarization is carried out for about 2 hours. In some embodiments, solarization is carried out for about 10 hours. In some embodiments, solarization is carried out until the extract changes from a nettle green color to a yellow-brown color. In some embodiments, solarization is carried out until the optical density difference (ODD) of the solution reaches a value indicating acceptable chlorophyll levels in the *cannabis* extract, as measured on a UV-vis spectrophotometer measuring the difference in absorption between wavelengths around 650 nm (red) and around 940 nm (infrared). The measurement of the ODD between these two wavelengths can be used to determine the chlorophyll content in the *cannabis* extract. One of skill in the art will recognize that there are other techniques available to determine the amount of chlorophyll remaining in extracts.

The method 100 can include solarizing the second eluate 113 in step 106. For illustrative purposes, solarizing the eluate 109 will be described with respect to the second eluate 113, although it should be understood that any type of eluate or menstruum produced from the *cannabis* plant material 103 can be solarized to remove the effects of chlorophyll from the eluate 109.

Step 106 can involve exposing the second eluate 113 to direct sunlight in order to solarize the second eluate 113. In one embodiment, the glass container comprising the second eluate 113 can be placed in direct sunlight for at least two hours. In other embodiments, a plasma light emitter can be used to direct light at the second eluate 113 at a light intensity between about 500 to about 2000 photosynthetic photon flux (PPF or µmol m$^{-2}$ s$^{-1}$) for approximately 8 to 10 hours.

Solarization can be accomplished using any source of light suitable for degrading chlorophyll. The light source can be, for example, the sun. Another source of light used can be non-natural light sources. Non-natural light sources can include those that emit a full light spectrum in an attempt to mimic natural light, or those that only provide specific wavelengths. Non-natural light sources can also include those that vary spectral outputs and temperatures as time passes, or those that keep a constant spectral output and temperature. In some embodiments the light source is sunlight. In some embodiments the light source is a plasma light (e.g., a Gavita Pro 300 light emitting plasma lamp equipped with LUXIM STA 41.02 LiFi light source). The plasma light can be a full-spectrum plasma light including UVB light.

The solarization step can be conducted at any temperature suitable for degrading, or otherwise reducing, the chlorophyll in the extract. Typically, solarization will be conducted at a temperature ranging from about −80° C. to about 30° C. The solarization step can be conducted, for example, at a temperature ranging from about −80° C. to about −20° C., or from about −20° C. to about 0° C., or from about 0° C. to about 4° C., or from about 4° C. to about 20° C. In some embodiments, the solarization step is conducted a temperature below about 0° C. In some embodiments, solarization step is conducted at about −23° C.

In all such embodiments, the solarization of the second eluate 113 can cease when the color of the second eluate 113 no longer exhibits a green hue or turns from a green color to a yellowish-brown color. It has been discovered that the solarization step allows oil producers to elute more of the cannabinoids 107 from the same batch of the *cannabis* plant material 103 through the two-step process described above. More specifically, the solarization step allows oil producers to make the *cannabis* oil extract from the second eluate 113 without leaving undesirable amounts of chlorophyll into the final product. In one embodiment, the level of cannabinoids 107 of the first eluate 111 and the second eluate 113 are assayed using high-performance liquid chromatography (HPLC) and ultraviolet (UV) detectors. In this embodiment, the second eluate 113 contains about 10% less cannabinoids 107 than the first eluate 111.

Generally, after the solarization step, the eluate is cooled to temperatures below ambient temperature (i.e., below about 25° C.). For example, the eluate can be held at a temperature ranging from about −80° C. to about 20° C. The eluate can be held at a temperatures ranging from about −80° C. to about −20° C., or from about −20° C. to about 0° C., or from about 0° C. to about 4° C., or from about 4° C. to about 20° C. In some embodiments, the eluate is held at about 0° C. In some embodiments, the eluate is held at about −20° C.

One of skill in the art will appreciate that the length of cooling time will depend in part on factors such as the targeted freezing/cooling temperature and the quantity of materials used in the methods. Accordingly, the eluate is typically held for periods of time ranging from several minutes to several hours in length. For example, eluate can be held at reduced temperatures for about 5 minutes to about 3 days or more. In some embodiments, the eluate can be held at reduced temperatures from about 5 minutes to about 1 hour, from about 1 hour to about 5 hours, from about 5 hours to about 24 hours, from about 24 hours to about 48 hours, from about 48 hours to about 96 hours or more. In some embodiments, the eluate is held at reduced temperatures for about 24 hours. In some embodiments, the eluate is held at reduced temperatures for about 48 hours.

The second eluate 113 can be stored for about 24 to about 48 hours at a temperature between about 0° C. and about −20° C. After this freezing step, the second eluate 113 can undergo further filtration in step 108 below.

The method 100 can further include filtering the eluate 109, including the first eluate 111, the second eluate 113, or a combination thereof, with a filter to produce a filtrate 115 in step 108. In one embodiment, step 108 includes filtering the eluate 109 using vacuum filtration. In a more specific embodiment, step 108 can include pouring the eluate 109 through a Büchner funnel coupled to a vacuum or side-arm flask. In these and other embodiments, the Büchner funnel can represent the filter.

In this embodiment, one or more pieces of filter paper can be placed in the Büchner funnel and a vacuum pump can be used to provide vacuum suction. In one embodiment, the filter paper can have a pore size of between 12-25 micrometers (μm). As a more specific embodiment, the filter paper can be a Whatman™ ashless Grade 589 filter paper. In this embodiment, two pieces of the filter paper can be placed in the Büchner funnel to filter the eluate 109.

Step 108 can also include freezing the Büchner funnel prior to pouring the eluate 109 into the funnel. In addition, step 108 can include wetting the filter paper with the solvent 105 prior to pouring the eluate 109 into the Büchner funnel. The filtrate 115 can be collected from the vacuum or side-arm flask and undergo evaporation in step 110.

The method 100 can further include evaporating the solvent 105 from the filtrate 115 to produce a distillate 117 in step 110. In some embodiments, the filtrate 115 can be distilled using a distiller. In some embodiments, the filtrate can be distilled using an evaporator. In some embodiments, the evaporator can be a rotary evaporator. In some embodiments, the distiller can include an essential oil distiller. As a more specific embodiment, the distiller can be a Megahome™ DA4B distiller. The filtrate 115 can be distilled by separating the solvent 105 from the remainder of the filtrate 115 through a selective evaporation and condensation procedure.

The filtrate can be distilled or evaporated for any length of time, depending on the desired concentration of distillate. For example, the filtrate can be distilled or evaporated for anytime ranging from about 30 minutes to about 10 hours or more. An ordinary skilled artisan will recognize that depending on the exact method and machinery used, the exact evaporation time required will vary. In some embodiments, the filtrate is evaporated for time intervals ranging from about 30 minutes to about 2 hours, from about 2 hours to about 4 hours, from about 4 hours to about 6 hours, from about 6 hours to about 8 hours, or from about 8 hours to about 10 hours. In some embodiments, the filtrate is distilled or evaporated for about 2 hours. In some embodiments, the filtrate is distilled or evaporated for about 8 hours. In some embodiments, step 110 can include distilling the filtrate 115 for at least 4 hours.

After evaporating the solvent from the filtrate, the distillate can be optionally heated above room temperature under controlled conditions for an additional period of time. In some embodiments, the distillate is heated at a controlled temperature for a period of time sufficient to convert acidic cannabinoids to neutral cannabinoids via decarboxylation. The distillate, after evaporation and optional heating, is transferred to an appropriate heating flask. A condenser with recirculating chilling fluid is attached on top of the appropriate heating flask to condense oil vapors during the heating process.

Accordingly, some embodiments of the invention provide a method for preparing a *cannabis* oil extract as described above, wherein the method further includes heating the distillate under conditions sufficient to form a decarboxylated distillate.

After distillation and optional heating, the distillate can be optionally filtered through a solid-phase filter medium. Examples of suitable solid-phase filter media include, but are not limited to, silica gel, activated charcoal, activated carbon, diatomaceous earth (Celite), and ion-exchange resins. In some embodiments, the solid-phase filter medium is silica gel. The distillate can be homogenized or otherwise combined with a suitable solvent prior to the optional filtration step. The homogenized distillate can then be added to a portion of silica gel that has been conditioned (pre-run) in a suitable filter apparatus with the same solvent as added to the distillate. Once the homogenized distillate is fully absorbed on the silica, additional solvent can be added on top of the settled silica. During the silica gel filtration step, the homogenized distillate and added solvent can be pulled through the filter apparatus using a light vacuum or pushed through the filter apparatus using positive pressure applied from above. Alternatively, the homogenized distillate can proceed through the apparatus via gravity filtration. The filtrate can be collected in an appropriate flask prior to removal of solvent via evaporation, as described above.

The solvent used in homogenizing the distillate can be any of the solvents discussed above, including ethanol, ethyl acetate, or heptane. The ratio of solvent added can range from about 1 mL solvent to about 1 g of distillate (1:1) to about 4:1 (mL solvent to g of distillate). For example, the ratio of solvent to distillate can be from about 1:1 to about 2:1, from about 2:1 to about 3:1, or from about 3:1 to about 4:1. In some embodiments, the ratio of solvent to distillate is about 2:1. In some embodiments, the ratio of solvent to distillate is about 3:1.

Silica gel can be added to the homogenized distillate in any amount suitable for removing unwanted components via filtration. Silica gel can be added, for example, in an amount ranging from about 1 g of added silica for every 1 g of homogenized distillate (1:1) to about 3 g of added silica for every 1 g of homogenized distillate (3:1). The amount of added silica added to homogenized distillate can range from about 1:1 to about 2:1, or from about 2:1 to about 3:1. In some embodiments the ratio of added silica to homogenized distillate is about 2:1. Additional silica gel is used as the pad or be in the filtration step. Typically, the additional silica gel is used in amounts ranging from about 3 g silica for every 1 g of homogenized distillate (3:1) to about 9:1. For example, the ratio of additional silica to homogenized distillate can range from about 3:1 to about 4:1, from about 4:1 to about 5:1, from about 5:1 to about 6:1, from about 6:1 to about 7:1, from about 7:1 to about 8:1, or form about 8:1 to about 9:1. In some embodiments, the ratio of additional silica to distillate is about 6:1. In some embodiments, the ratio of additional silica to distillate is about 4:1. In some embodiments the additional silica is loaded into the funnel alone. In some embodiments, the additional silica gel is loaded into the funnel with the same solvent used to homogenize the distillate.

Accordingly, some embodiments of the invention provide a method for preparing a *cannabis* oil extract as described above, wherein the method further includes heating the distillate under conditions sufficient to form a decarboxylated distillate and filtering the decarboxylated distillate to form a decarboxylated filtrate.

The method 100 can further include dehydrating or purging the distillate 117 (after optional filtration and heating) to further remove any further traces of the solvent 105. In doing so, the dehydration produces an extract 119 in step 112. Dehydration can be achieved using any known means in the art including the use of a food dehydrator, evaporator, or vacuum pump. In some embodiments the distillate is placed in an open container. In some embodiments the distillate is place in a sealed container where air pressure can be lowered.

In general, purging/dehydration is conducted under conditions sufficient to remove residual solvent from the *cannabis* oil extract. "Residual solvent" refers to any solvent (e.g., ethanol) used during the extraction process that remains in the extract after the elution, solarization, filtration, and evaporation steps. The removal of residual solvent can be monitored, for example, by conducting the purge/dehydration step until the weight of the extract stops decreasing (indicating that all volatile solvent has been removed). In some embodiments, removing residual solvent refers to removing at least 90% of the ethanol used in the extraction process from the *cannabis* oil extract. In some embodiments, removing residual solvent refers to removing at least 95% of the ethanol used in the extraction process from the *cannabis* oil extract. In some embodiments, removing residual solvent refers to removing at least 99% of the ethanol used in the extraction process from the *cannabis* oil extract.

In some embodiments, the dehydrator can be a food dehydrator. In a more specific embodiment, the dehydrator can be an Excalibur™ food dehydrator. Step 112 can involve placing the petri dishes comprising the distillate 117 into the dehydrator. In one embodiment, the dehydrator can be set at about 55° C. The distillate 117 can be dehydrated for at anywhere between about 1 and about 72 hours, or longer, to yield the extract 119. In other embodiments, the distillate 117 can be dehydrated for up to about 120 hours.

In some embodiments, dehydration of residual solvent can be achieved with vacuum pumps providing reduced pressure levels ranging from about 1 mbar to about 500 mbar. In some instances, solvent purging is carried about from about 1 mbar to about 10 mbar, or from about 10 mbar to about 20 mbar, or from about 20 mbar to about 50 mbar, or from about 50 mbar to about 100 mbar, or from about 100 mbar to about 200 mbar, or from about 200 mbar to about 500 mbar. In some embodiments the solvent purging pressure is about 10 mbar. In some embodiments, the solvent purging pressure is about 50 mbar. In some embodiments, the solvent purging pressure is about 100 mbar. In some embodiments, the solvent purging pressure is about 250 mbar. Reduced pressures can be obtained using any suitable apparatus including, for example, an Across International Vacuum Oven (Model VO-16050) or a Buchi Multivapor apparatus equipped with a vacuum pump. In some embodiments, the distillate is purged while being stirred and heated in a heavy-walled flask under reduced pressure.

During the purge/dehydration step, the distillate may be optionally heated to increase the efficiency of the solvent purge. The temperature used for purging/dehydration can be any temperature at or above ambient conditions. For example, heating during the purge/dehydration step can range from about 20° C. to about 200° C. or more. In some instances the purge/dehydration temperature can range from about above 20° C. to about 35° C., or from about 35° C. to about 50° C., or from about 50° C. to about 65° C., or from about 65° C. to about 90° C., or from about 90° C. to about 130° C., or from about 130° C. to about 170° C., or from about 170° C. to about 200° C. or more. In some embodiments, the purge/dehydration temperature is about 35° C. In some embodiments, the purge/dehydration temperature is about 50° C. In some embodiments, the purge/dehydration temperature is about 55° C. In some embodiments, the purge/dehydration temperature is about 70° C. In some embodiments, the purge/dehydration temperature is about 90° C. In some embodiments, the purge/dehydration temperature is about 110° C.

A person of skill in the art will recognize that the time of dehydration required to remove the remaining solvent will depend on the pressure and temperature of the purge/dehydration step as well as the solvent that is being removed. Typically, the time of the purge step will range from anywhere between about 1 hour and about 5 days. For example, the time of purging can range from about 1 hour to about 1 day, from about 1 day to about 2 days, from about 2 days to 3 days, or from about 3 days to about 5 or more days. In some embodiments, the time of purging is about 18 hours. In some embodiments, the time of purging is about 2 days. In some embodiments, the time of purging can is about 3 days. In some embodiments, the time of purging can is about 4 days. In some embodiments, the time of purging is about 5 days.

After obtaining the extract 119, the composition of the extract can be determined by a variety of the methods. For example, a portion of the extract can be analyzed by methods including, but not limited to, liquid chromatography/mass spectrometry (LC-MS), gas chromatography/mass spectrometry (GC-MS), and proton nuclear magnetic resonance spectroscopy ($^1$H-NMR). In addition, the composition of the extract 119 can be organoleptically tested to ensure consistency in taste, smell, texture, coloration, or a combination thereof.

As an example, Table 1 below shows the amount and percent yields of extract 119 from varying amounts of *cannabis* plant material 103:

TABLE 1

Yield Results from *Cannabis* Plant Material to Extract

| *Cannabis* Plant Material Strain | *Cannabis* Plant Material Amount (grams) | Amount of Solvent, Ethanol (L) | Extract Yield Amount (grams) | Extract Yield Percentage (%) |
| --- | --- | --- | --- | --- |
| AC/DC | 680.39 | 7.00 | 42.0 | 6.17 |
| Blueberry | 1315.41 | 13.0 | 79.8 | 6.07 |
| Cannatonic | 680.38 | 10.5 | 41.4 | 6.08 |

The method 100 can further include mixing a quantity of vitamin E 121 with the extract 119 to yield a *cannabis* oil composition.

The amount of vitamin E added to the extract can depend on factors including the strain of *cannabis* plant used and desired viscosity of the extract. The amount of vitamin E added to the extract will typically range from about 0% (w/w) to about 95%. The amount of vitamin E added to the extract can range, for example, from about 0.5% to about 5%, or from about 5% to about 10%, or from about 10% to about 15%, or from about 15% to about 20%, or from about 20% to about 25%, or from about 25% to about 30%, or from about 30% to about 35%, or from about 35% to about 40%, or from about 40% to about 50%, or from about 50% to about 60%, or from about 60% to about 70% or more. The amount of vitamin E added can range from about 54% to about 56%, or from about 52% to about 58%, or from about 49% to about 61%, or from about 47% to about 63%, or from about 46% to about 64%, or from about 44% to about 66%. The amount of vitamin E added can range from about 12% to about 48%, or from about 14% to about 46%, or from about 16% to about 44%, or from about 18% to about 42%, or from about 20% to about 40%, or from about 22% to about 38%, or from about 24% to about 36%, or from about 26% to about 34%, or from about 28% to about 32%. In some embodiments, the amount of vitamin E added to the extract is about 15% or more. In some embodiments, the amount of vitamin E added is about 28% or more. In some embodiments, the amount of vitamin E added is about 30% or more. In some embodiments, the amount of vitamin E added is about 44% or more. In some embodiments, the amount of vitamin E added is about 55% or more.

In certain embodiments, vitamin E is added to the *cannabis* oil in an amount sufficient to provide a desired viscosity level. For example, vitamin E can be added to the *cannabis* oil in an amount sufficient to provide a viscosity ranging from about 6000 cP to about 200 cP. Vitamin E can be added to the *cannabis* oil in an amount sufficient to provide a viscosity ranging from about 6000 cP to about 5000 cP, or from about 5000 cP to about 4000 cP, or from about 4000 cP to about 3000 cP, or from about 3000 cP to about 2000 cP, or from about 2000 cP to about 1000 cP, or from about 1000 cP to about 200 cP. In certain instances, vitamin E is added to the *cannabis* oil in an amount sufficient to provide a viscosity of less than about 3500 cP. In certain other instances, vitamin E is added to the *cannabis* oil in an amount sufficient to provide a viscosity ranging from about 1050 cP to about 950 cP, or from about 1100 cP to about 900 cP, or from about 1150 cP to about 850 cP, or from about 1200 cP to about 800 cP, or from about 1250 cP to about 750 cP, or from about 1300 cP to about 700 cP, or from about 1350 cP to about 650 cP. In some embodiments, vitamin E is added to the *cannabis* oil in an amount sufficient to provide a viscosity of about 1000 cP. In some embodiments, vitamin E is added to the *cannabis* oil in an amount sufficient to provide a viscosity of about 2500 cP.

In one preferred embodiment, the quantity of vitamin E mixed with the extract 119 is about 30 percent weight by weight (30% w/w) based on a total weight of the *cannabis* oil composition. In other embodiments, the quantity of vitamin E mixed with the extract 119 can be between about 30% w/w and about 50% w/w based on the total weight of the *cannabis* oil composition.

In these and other embodiments, the vitamin E 121 can be, but is not limited to, vitamin E derived from organic sources. For example, the vitamin E 121 can be vitamin E derived from organic sunflowers. As a more specific embodiment, the vitamin E 121 can be Deva™ non-genetically modified (non-GMO) vitamin E from sunflowers. The vitamin E 121 can include tocopherols and tocotrienols. More specifically, the vitamin E 121 can include α-tocopherol.

Step 114 can include placing a suitable vessel, such as a beaker or petri dish, comprising the extract 119 on a hotplate set at about 60-95° C. Step 114 can further include mixing the vitamin E 121 with the extract 119 by gently stirring the vitamin E 121 into the extract 119 warmed on the hotplate until the *cannabis* oil composition is homogenized. In another embodiment, mixing the vitamin E 121 with the extract 119 can involve injecting a quantity of the vitamin E 121 into the extract 119. In some embodiments, mixing the vitamin E with the extract can involve adding a quantity of the vitamin E into extract that is being mechanically or manually stirred and heated in a flask.

III. *Cannabis* Oils

In related aspects, the present invention provides *cannabis* oil extracts and compositions prepared by the methods described herein.

A. Cannabinoids

*Cannabis* oils of the invention can contain neutral cannabinoids, acidic cannabinoids, and combinations thereof. Examples of neutral cannabinoids include, but are not limited to: cannabigerol (CBG) and related compounds (e.g., cannabigerol monomethyl ether, cannabigerovarin); cannabichromene (CBC) and related compounds (e.g., (±)-cannabichromene, (±)-cannabichromevarin); (−)-cannabidiol (CBD) and related compounds (e.g., cannabidiol momomethyl ether, cannabidiol-$C_4$, (−)-cannabidivarin, cannabidiorcol); cannabinodiol (CBND) and related compounds (e.g., cannabinodivarin); $\Delta^9$-tetrahydrocannabinol (THC) and related compounds (e.g., $\Delta^9$-tetrahydrocannabinol-$C_4$, $\Delta^9$-tetrahydrocannabivarin, $\Delta^9$-tetrahydro-cannabiorcol, (−)-$\Delta^8$-trans-(6aR,10aR)-$\Delta^8$-tetrahydrocannabinol, (−)-(6aS,10aR)-$\Delta^9$-tetrahydro-cannabinol); cannabinol (CBN) and related compounds (e.g., cannabinol-$C_4$, cannabivarin, cannabinol-$C_2$, cannabiorcol, cannabinol methyl ether); (±)-cannabitriol (CBT) and related compounds (e.g., (−)-(9R,10R)-trans-10-O-ethyl-cannabitriol, (±)-(9R,10R/9S,10S)-cannabitriol-$C_3$); cannabielsoin (CBE) and related compounds (e.g., (5aS,6S,9R,9aR)-cannabielsoin, (5aS,6S, 9R,9aR)—$C_3$-cannabielsoin, cannabiglendol-$C_3$, dehydrocannabifuran, cannabifuran); isocannabinoids (e.g., (−)-$\Delta^7$-trans-(1R,3R,6R)-isotetrahydrocannabinol, (±)-$\Delta^7$-1,2-cis-(1R,3R,6S)-isotetrahydrocannabivarin, (±)-$\Delta^7$-1,2-cis-(1S, 3S,6R)-isotetrahydro-cannabivarin, (−)-$\Delta^7$-trans-(1R,3R, 6R)-isotetrahydrocannabivarin); cannabicyclol (CBL) and related compounds (e.g., (±)-(1 aS,3aR,8bR,8cR)-cannabicyclol CBL-$C_5$, (±)-(1aS,3aR,8bR,8cR)-cannabicyclovarin); cannabicitran (CBT) and related compounds; and cannabichromanone (CBCN) and related compounds (e.g., cannabichromanone-$C_3$, cannabicoumaronone). The structures of various neutral cannabinoids are set forth below.

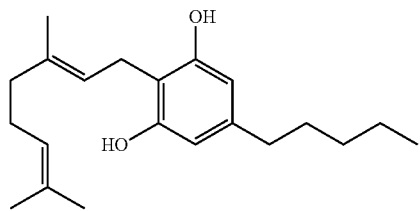

cannabigerol
[CBG]

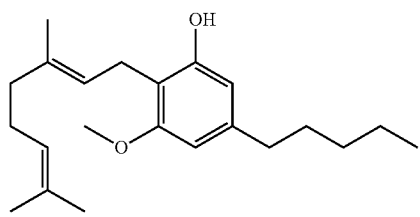

cannabigerol monomethyl ether
[CBGM]

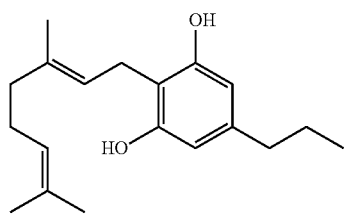

cannabigerovarin
[CBGV]

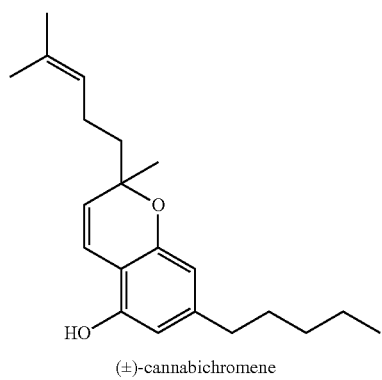

(±)-cannabichromene
[CBC]

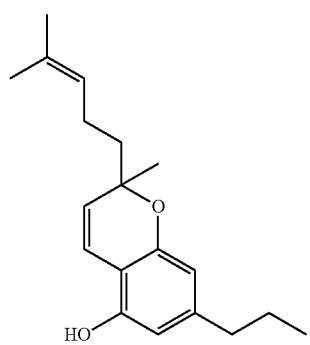

(±)-cannabichromevarin
[CBCV]

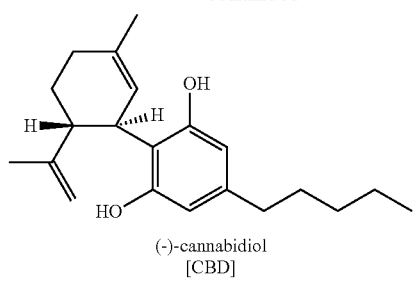

(-)-cannabidiol
[CBD]

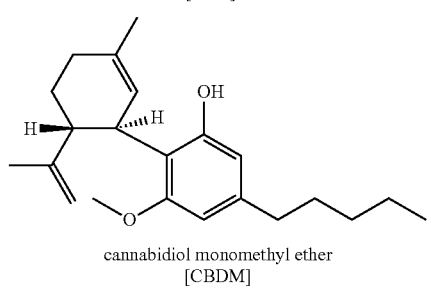

cannabidiol monomethyl ether
[CBDM]

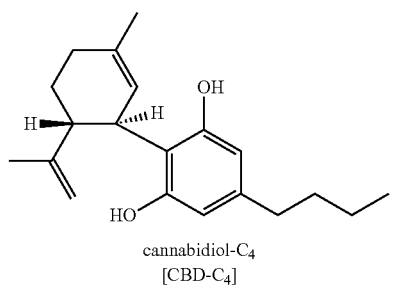

cannabidiol-$C_4$
[CBD-$C_4$]

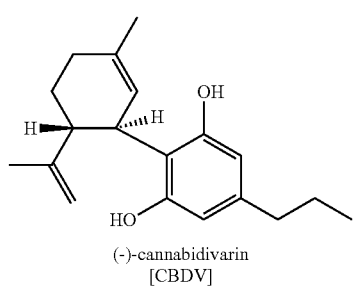

(-)-cannabidivarin
[CBDV]

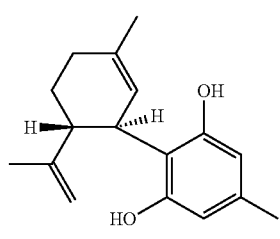

cannabidiorcol
[CBD-$D_1$]

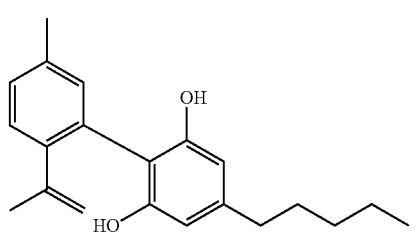

cannabinodiol
[CBND]

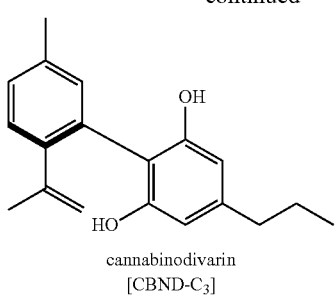
cannabinodivarin
[CBND-C$_3$]
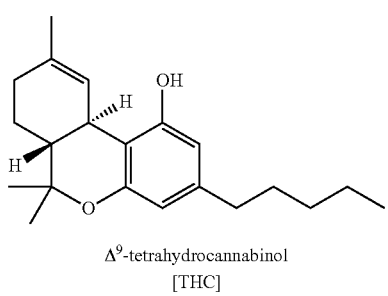
Δ$^9$-tetrahydrocannabinol
[THC]
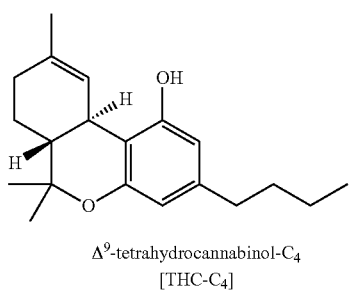
Δ$^9$-tetrahydrocannabinol-C$_4$
[THC-C$_4$]
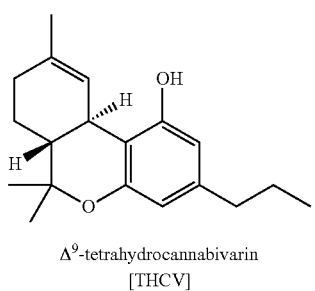
Δ$^9$-tetrahydrocannabivarin
[THCV]
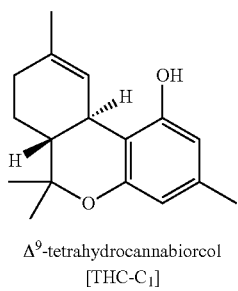
Δ$^9$-tetrahydrocannabiorcol
[THC-C$_1$]
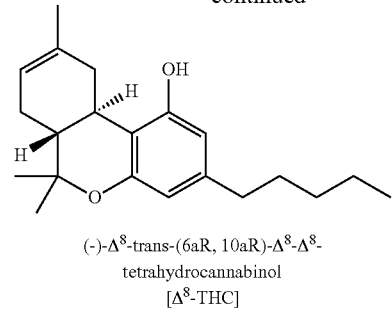
(-)-Δ$^8$-trans-(6aR, 10aR)-Δ$^8$-Δ$^8$-
tetrahydrocannabinol
[Δ$^8$-THC]
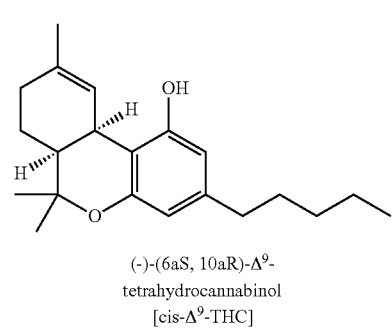
(-)-(6aS, 10aR)-Δ$^9$-
tetrahydrocannabinol
[cis-Δ$^9$-THC]
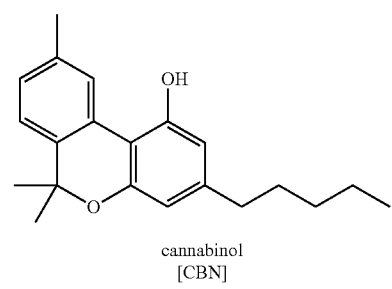
cannabinol
[CBN]
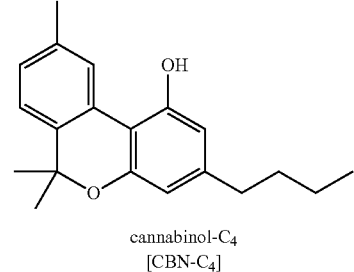
cannabinol-C$_4$
[CBN-C$_4$]
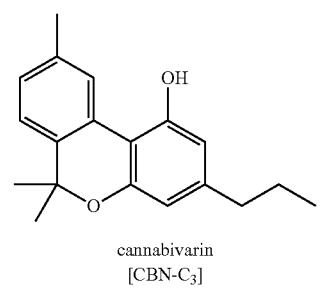
cannabivarin
[CBN-C$_3$]

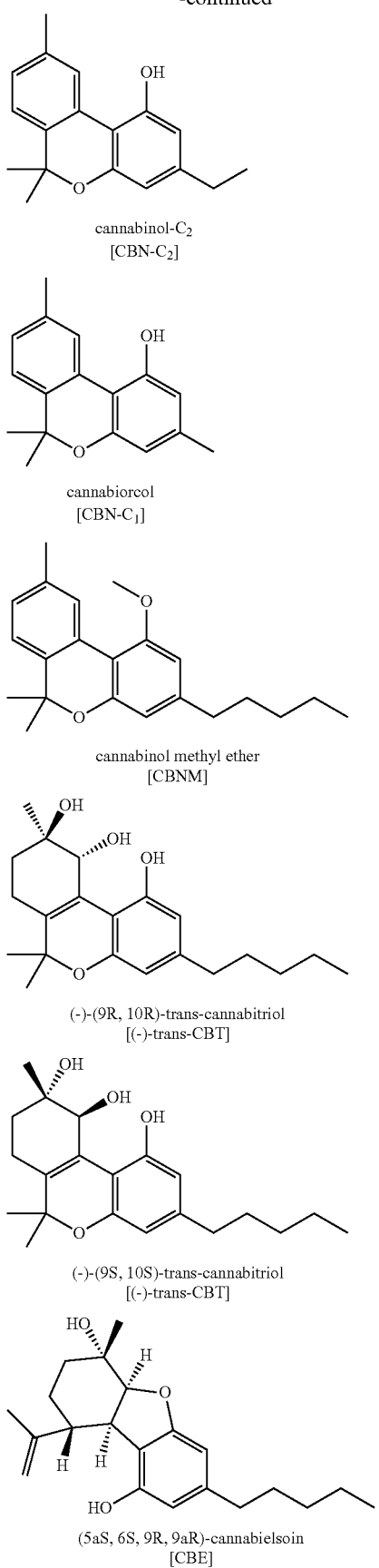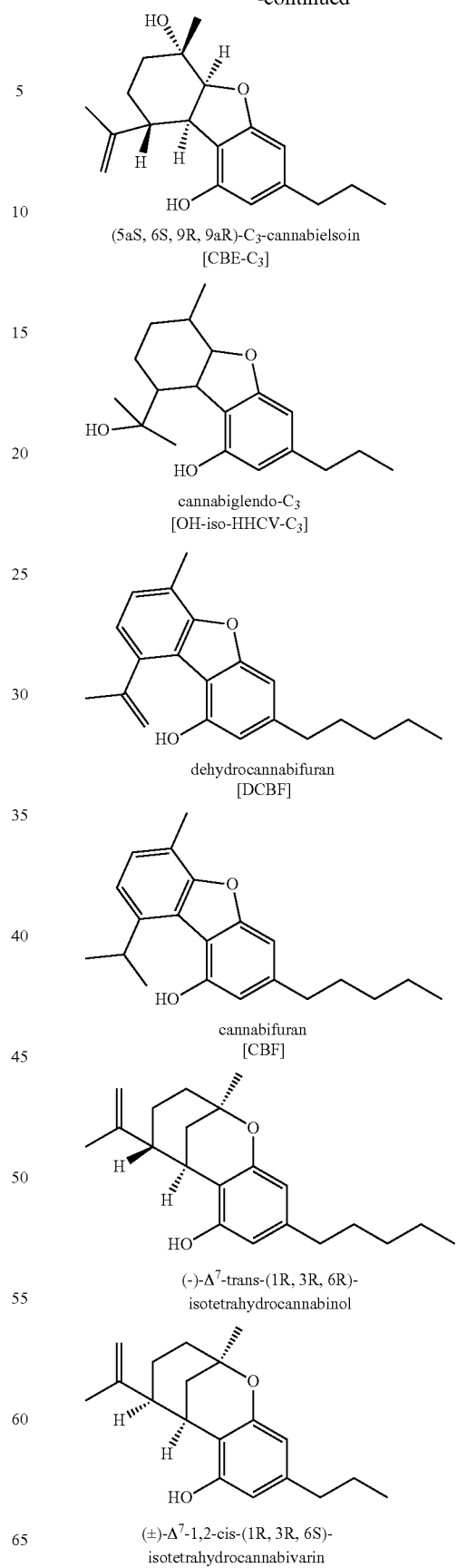

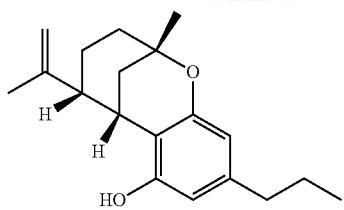

(±)-Δ⁷-1,2-cis-(1S, 3S, 6R)-
isotetrahydrocannabivarin

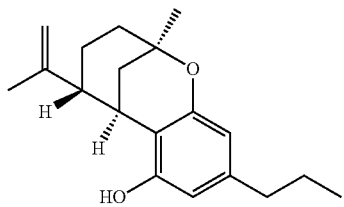

(−)-Δ⁷-1,2-trans-(1R, 3R, 6R)-
isotetrahydrocannabivarin

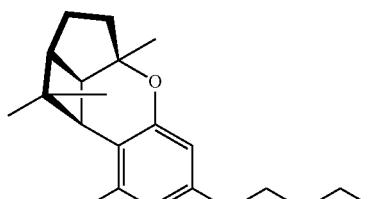

(±)-(1aS, 3aR, 8bR, 8cR)-
cannabicyclol
[CBL]

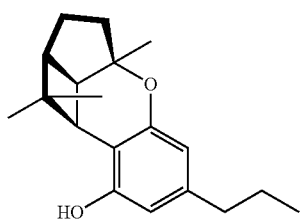

(±)-(1aS, 3aR, 8bR, 8cR)-
cannabicyclovarin
[CBLV]

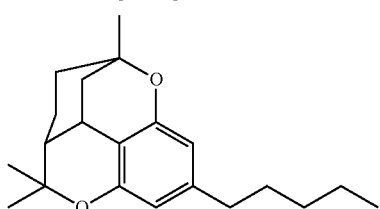

cannabicitran
[CBT]

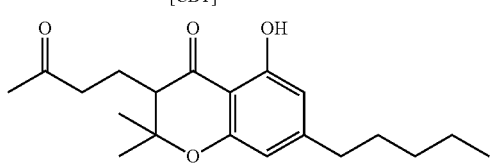

cannabichromanone
[CBCN]

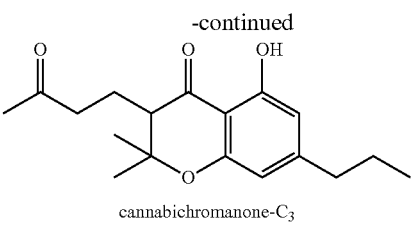

cannabichromanone-C₃
[CBCN-C₃]

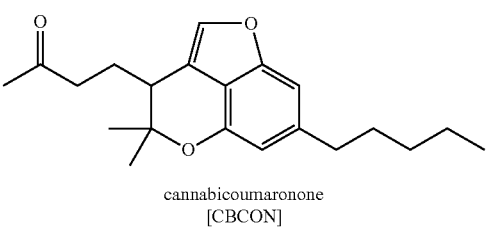

cannabicoumaronone
[CBCON]

Examples of acidic cannabinoids include, but are not limited to: cannabigerolic acid A; cannabigerolic acid A monomethyl ether; cannabigerovarinic acid A; (±)-cannabichromenic acid A; (±)-cannabichromevarinic acid A; cannabidiolic acid; cannabidivarinic acid; $\Delta^9$-tetrahydrocannabinolic acid A; $\Delta^9$-tetrahydrocannabinolic acid B; $\Delta^9$-tetrahydrocannabinolic acid-C₄ A; $\Delta^9$-tetrahydrocannabinolic acid-C₄ B; $\Delta^9$-tetrahydro-cannabivarinic acid A; $\Delta^9$-tetrahydrocannabiorcolic acid A; $\Delta^9$-tetrahydrocannabiorcolic acid B; (−)-$\Delta^8$-trans-(6aR,10aR)-tetrahydrocannabinolic acid A; cannabinolic acid A; (5aS,6S,9R,9aR)-cannabielsoic acid A; (5aS,6S,9R,9aR)-cannabielsoic acid B; (5aS,6S,9R,9aR)—C₃-cannabielsoic acid B; and (±)-(1aS,3aR,8bR,8cR)-cannabicyclolic acid A. The structures of various acidic cannabinoids are set forth below.

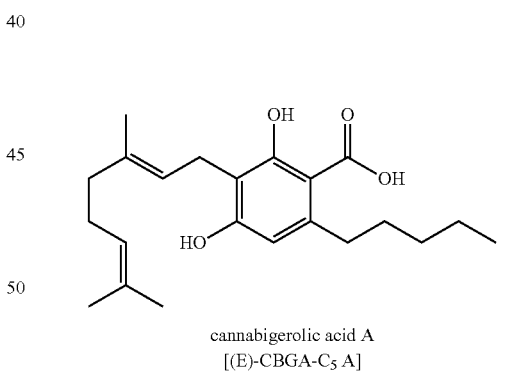

cannabigerolic acid A
[(E)-CBGA-C₅ A]

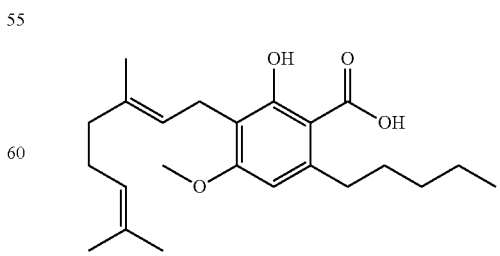

cannabigerolic acid A monomethyl ether
[(E)-CBGAM-C₅ A]

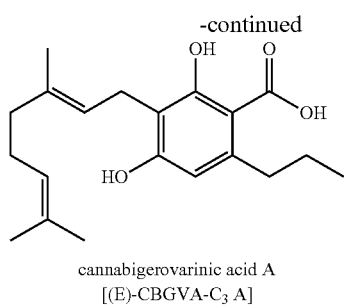

cannabigerovarinic acid A
[(E)-CBGVA-C₃ A]

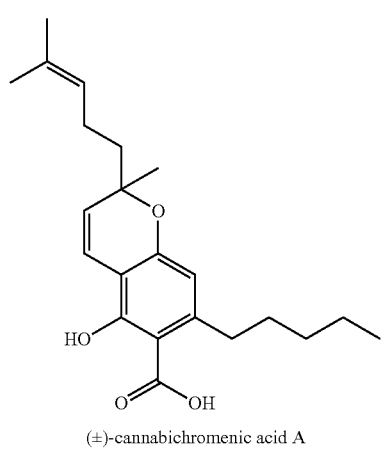

(±)-cannabichromenic acid A
[CBCA-C₅ A]

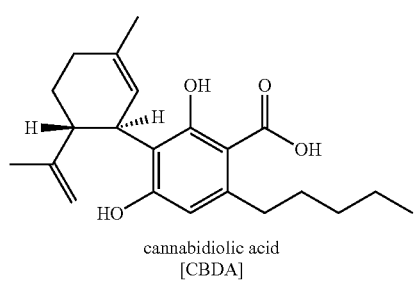

cannabidiolic acid
[CBDA]

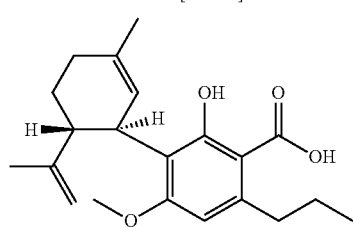

cannabidivarinic acid
[CBDVA]

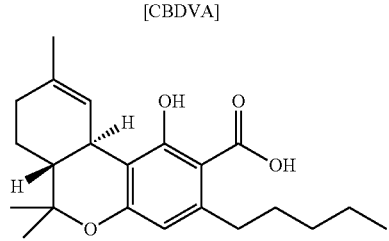

Δ⁹-tetrahydrocannabinolic acid A
[Δ⁹-THCA A]

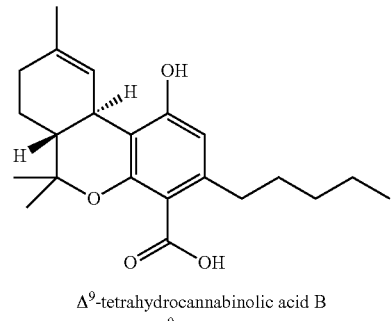

Δ⁹-tetrahydrocannabinolic acid B
[Δ⁹-THCA B]

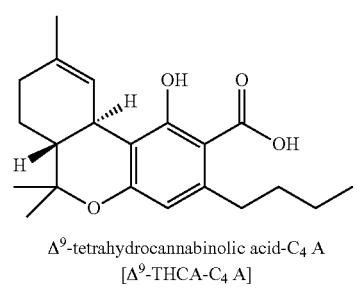

Δ⁹-tetrahydrocannabinolic acid-C₄ A
[Δ⁹-THCA-C₄ A]

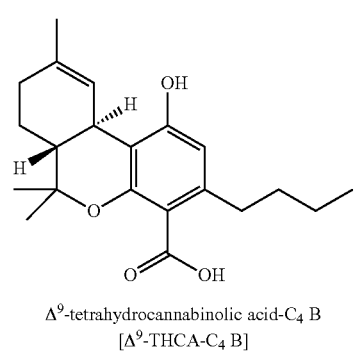

Δ⁹-tetrahydrocannabinolic acid-C₄ B
[Δ⁹-THCA-C₄ B]

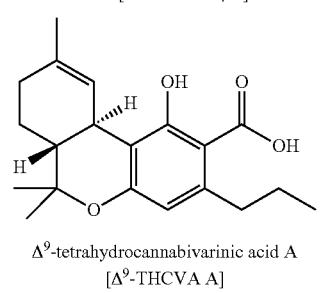

Δ⁹-tetrahydrocannabivarinic acid A
[Δ⁹-THCVA A]

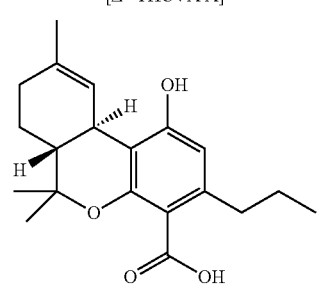

Δ⁹-tetrahydrocannabivarinic acid B
[Δ⁹-THCVA B]

-continued

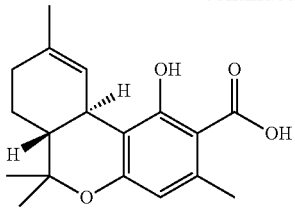

Δ⁹-tetrahydrocannabiorcolic acid A
[Δ⁹-THCOA A]

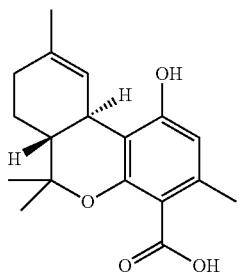

Δ⁹-tetrahydrocannabiorcolic acid B
[Δ⁹-THCOA B]

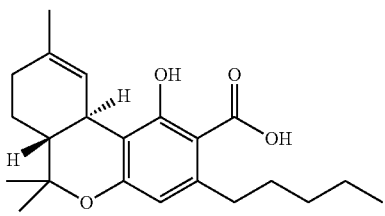

(-)-Δ⁸-trans-(6aR, 10aR)-Δ⁸-
tetrahydrocannabinolic acid A
[Δ⁸-THCA A]

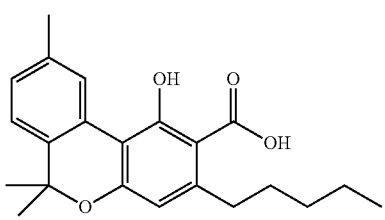

cannabinolic acid A
[CBNA A]

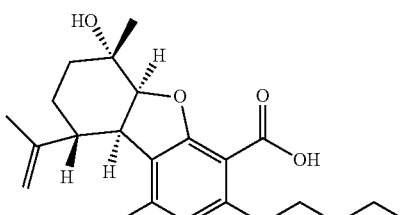

(5aS, 6S, 9R, 9aR)-cannabielsoic acid A
[CBEA A]

-continued

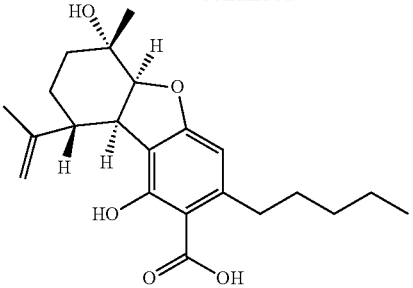

(5aS, 6S, 9R, 9aR)-cannabielsoic acid B
[CBEA B]

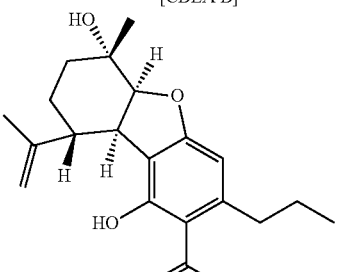

(5aS, 6S, 9R, 9aR)-C₃-cannabielsoic acid B
[CBEA-C₃ B]

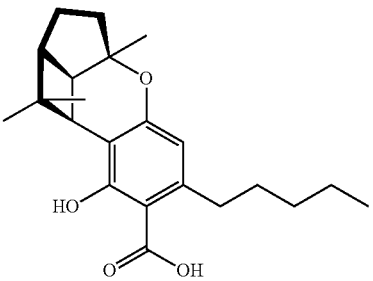

(±)-(1aS, 3aR, 8bR, 8cR)-cannabicyclolic
[CBLA A]

In general, neutral cannabinoids (such as THC, CBD, CBG, CBN, and other neutral cannabinoids) are present in the oils of the present invention (e.g., *cannabis* oil extracts or compositions comprising same) in amounts ranging from about 0.001% (w/w) to about 99% (w/w). In certain embodiments, a neutral cannabinoid (such as THC, CBD, CBG, CBN, or another neutral cannabinoid) will be present in an amount ranging from about 1% (w/w) to about 99% (w/w). A neutral cannabinoid (such as THC, CBD, CBG, CBN, or another neutral cannabinoid) can be present, for example, in an amount ranging from about 0.01% (w/w) to about 0.05% (w/w), or from about 0.05% (w/w) to about 0.1% (w/w), or from about 0.1% (w/w) to about 0.2% (w/w), or from about 0.2% (w/w) to about 0.3% (w/w), or from about 0.3% (w/w) to about 0.4% (w/w), or from about 0.4% (w/w) to about 0.5% (w/w), or from about 0.5% (w/w) to about 0.6% (w/w), or from about 0.6% (w/w) to about 0.7% (w/w), or from about 0.7% (w/w) to about 0.8% (w/w), or from about 0.8% (w/w) to about 0.9% (w/w), or from about 0.9% (w/w) to about 1% (w/w), or from about 1% (w/w) to about 5% (w/w), or from about 5% (w/w) to about 10% (w/w), or from about 10% (w/w) to about 15% (w/w), or from about 15% (w/w) to about 20% (w/w), or from about 20% (w/w) to about 25% (w/w), or from about 25% (w/w) to about 30% (w/w), or from about 30% (w/w) to about 35% (w/w), or from about 35% (w/w) to about 40% (w/w), or from about 40% (w/w) to about 45% (w/w), or from about 45% (w/w) to about 50% (w/w), or from about 50% (w/w) to about 55% (w/w), or from about 55% (w/w) to about 60% (w/w), or from about 60% (w/w) to about 65% (w/w), or from about 65% (w/w) to about 70% (w/w), or from about 70% (w/w) to about 75% (w/w), or from about 75% (w/w) to about 80% (w/w), or from about 80% (w/w) to about 85% (w/w), or from about 85% (w/w) to about 90% (w/w), or from about 90% (w/w) to about 95% (w/w), or from about 95% (w/w) to about 99% (w/w).

A neutral cannabinoid (such as THC, CBD, CBG, CBN, or another neutral cannabinoid) can be present in an amount ranging from about 0.01% (w/w) to about 1% (w/w), or from about 0.02% (w/w) to about 0.9% (w/w), or from about 0.03% (w/w) to about 0.8% (w/w), or from about 0.04% (w/w) to about 0.7% (w/w), or from about 0.05% (w/w) to about 0.6% (w/w), or from about 0.06% (w/w) to about 0.5% (w/w), or from about 0.07% (w/w) to about 0.4% (w/w), or from about 0.08% (w/w) to about 0.3% (w/w), or from about 0.09% (w/w) to about 0.2% (w/w). A neutral cannabinoid (such as THC, CBD, CBG, CBN, or another neutral cannabinoid) can be present in an amount ranging from about 1% (w/w) to about 10% (w/w), or from about 2% (w/w) to about 9% (w/w), or from about 3% (w/w) to about 8% (w/w), or from about 4% (w/w) to about 7% (w/w), or from about 5% (w/w) to about 6% (w/w). A neutral cannabinoid (such as THC, CBD, CBG, CBN, or another neutral cannabinoid) can be present in an amount ranging from about 5% (w/w) to about 99% (w/w), or from about 10% (w/w) to about 95% (w/w), or from about 15% (w/w) to about 90% (w/w), or from about 20% (w/w) to about 85% (w/w), or from about 25% (w/w) to about 80% (w/w), or from about 30% (w/w) to about 75% (w/w), or from about 35% (w/w) to about 70% (w/w), or from about 40% (w/w) to about 65% (w/w), or from about 45% (w/w) to about 60% (w/w), or from about 50% (w/w) to about 55% (w/w).

Typically, THC will be present in an oil of the invention in an amount ranging from about 1% (w/w) to about 95% (w/w). Typically, THC is present in an amount ranging from about 10% (w/w) to about 95% (w/w). THC can be present, for example, in an amount ranging from about 1% (w/w) to about 5% (w/w), or from about 5% (w/w) to about 10% (w/w), or from about 10% (w/w) to about 15% (w/w), or from about 15% (w/w) to about 20% (w/w), or from about 20% (w/w) to about 25% (w/w), or from about 25% (w/w) to about 30% (w/w), or from about 30% (w/w) to about 35% (w/w), or from about 35% (w/w) to about 40% (w/w), or from about 40% (w/w) to about 45% (w/w), or from about 45% (w/w) to about 50% (w/w), or from about 50% (w/w) to about 55% (w/w), or from about 55% (w/w) to about 60% (w/w), or from about 60% (w/w) to about 65% (w/w), or from about 65% (w/w) to about 70% (w/w), or from about 70% (w/w) to about 75% (w/w), or from about 75% (w/w) to about 80% (w/w), or from about 80% (w/w) to about 85% (w/w), or from about 85% (w/w) to about 90% (w/w), or from about 90% (w/w) to about 95% (w/w). THC can be present in an amount ranging from about 5% (w/w) to about 95% (w/w), or from about 10% (w/w) to about 90% (w/w), or from about 15% (w/w) to about 85% (w/w), or from about 20% (w/w) to about 80% (w/w), or from about 25% (w/w) to about 75% (w/w), or from about 30% (w/w) to about 70% (w/w), or from about 35% (w/w) to about 65% (w/w), or from about 40% (w/w) to about 60% (w/w), or from about 45% (w/w) to about 55% (w/w).

In some embodiments, THC is present in an amount ranging from about 2% (w/w) to about 4% (w/w). In some embodiments, THC is present in an amount of about 1, 2, 3, 4, 5, 6, or 7% (w/w). In some embodiments, oils containing about 1-7% (w/w) THC (or other ranges between about 1% and about 7%) are prepared using the AC/DC *cannabis* strain.

In some embodiments, THC is present in an amount ranging from about 15% (w/w) to about 18% (w/w), or from about 18% (w/w) to about 21% (w/w), or from about 21% (w/w) to about 24% (w/w), or from about 24% (w/w) to about 27% (w/w), or from about 27% (w/w) to about 30% (w/w), or from about 30% (w/w) to about 33% (w/w), or from about 33% (w/w) to about 36% (w/w), or from about 36% (w/w) to about 39% (w/w), or from about 39% (w/w) to about 42% (w/w), or from about 42% (w/w) to about 45% (w/w). In some embodiments, THC is present in an amount ranging from about 15% (w/w) to about 45% (w/w), or from about 18% (w/w) to about 42% (w/w), or from about 21% (w/w) to about 39% (w/w), or from about 24% (w/w) to about 36% (w/w), or from about 27% (w/w) to about 33% (w/w). In some embodiments, THC is present in an amount of about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45% (w/w). In some embodiments, oils containing about 15-45% (w/w) THC (or other ranges between about 15% and about 45%) is prepared using a *cannabis* strain selected from Buddha Passion, Cannatonic, Medihaze, Harle OG, Harle Tsu, Hopesprings, Elektra, and Harlequin. In some embodiments, oils containing about 15-45% (w/w) THC (or other ranges between about 15% and about 45%) are prepared using the Cannatonic *cannabis* strain.

In some embodiments, THC is present in an amount ranging from about 50% (w/w) to about 53% (w/w), or from about 53% (w/w) to about 56% (w/w), or from about 56% (w/w) to about 60% (w/w), or from about 60% (w/w) to about 63% (w/w), or from about 63% (w/w) to about 66% (w/w), or from about 66% (w/w) to about 69% (w/w), or from about 69% (w/w) to about 72% (w/w), or from about 72% (w/w) to about 75% (w/w), or from about 75% (w/w) to about 78% (w/w), or from about 78% (w/w) to about 81% (w/w), or from about 81% (w/w) to about 84% (w/w), or from about 84% (w/w) to about 87% (w/w), or from about 87% (w/w) to about 90% (w/w). In some embodiments, THC is present in an amount ranging from about 50% (w/w) to about 90% (w/w), or from about 55% (w/w) to about 87% (w/w), or from about 66% (w/w) to about 84% (w/w), or from about 69% (w/w) to about 81% (w/w), or from about 72% (w/w) to about 78% (w/w). In some embodiments, THC is present in an amount of about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90% (w/w). In some embodiments, oils containing about 50-90% (w/w) THC (or other ranges between about 50% and about 90%) are prepared using a *cannabis* strain selected from Blueberry, Afghan Goo, Infinite Euphoria, Snowcap, Blackberry Kush, Sour Kush, Blue Diesel, and Prize Kush. In some embodiments, oils containing about 50-90% (w/w) THC (or other ranges between about 50% and about 90%) are prepared using the Blueberry *cannabis* strain.

Typically, CBD will be present in an oil of the invention in an amount ranging from about 0.1% (w/w) to about 99% (w/w). In some embodiments, CBD is present in an amount ranging from about 0.1% (w/w) to about 80% (w/w). CBD can be present, for example, in an amount ranging from about 0.1% (w/w) to about 1% (w/w), or from about 1% (w/w) to about 5% (w/w), or from about 5% (w/w) to about 10% (w/w), or from about 10% (w/w) to about 15% (w/w), or from about 15% (w/w) to about 20% (w/w), or from about 20% (w/w) to about 25% (w/w), or from about 25% (w/w) to about 30% (w/w), or from about 30% (w/w) to about 35% (w/w), or from about 35% (w/w) to about 40% (w/w), or from about 40% (w/w) to about 45% (w/w), or from about 45% (w/w) to about 50% (w/w), or from about 50% (w/w) to about 55% (w/w), or from about 55% (w/w) to about 60% (w/w), or from about 60% (w/w) to about 65% (w/w), or from about 65% (w/w) to about 70% (w/w), or from about 70% (w/w) to about 75% (w/w), or from about 75% (w/w) to about 80% (w/w). CBD can be present, for example, in an amount ranging from about 5% (w/w) to about 80% (w/w), or from about 10% (w/w) to about 75% (w/w), or from about 15% (w/w) to about 70% (w/w), or from about 20% (w/w) to about 65% (w/w), or from about 25% (w/w) to about 60% (w/w), or from about 30% (w/w) to about 55% (w/w), or from about 35% (w/w) to about 50% (w/w).

In some embodiments, CBD is present in an amount ranging from about 0.1% (w/w) to about 0.2% (w/w), or from about 0.2% (w/w) to about 0.6% (w/w), or from about 0.6% (w/w) to about 1% (w/w), or from about 1% (w/w) to about 1.4% (w/w), or from about 1.4% (w/w) to about 1.8% (w/w), or from about 1.8% (w/w) to about 2.2% (w/w), or from about 2.2% (w/w) to about 2.6% (w/w), or from about 2.6% (w/w) to about 3% (w/w), or from about 3% (w/w) to about 3.4% (w/w), or from about 3.4% (w/w) to about 3.8% (w/w), or from about 3.8% (w/w) to about 4.2% (w/w), or from about 4.2% (w/w) to about 4.6% (w/w), or from about 4.6% (w/w) to about 5% (w/w). In some embodiments, CBD is present in an amount ranging from about 0.2% (w/w) to about 5% (w/w), or from about 0.6% (w/w) to about 4.6% (w/w), or from about 1% (w/w) to about 4.2% (w/w), or from about 1.4% (w/w) to about 3.8% (w/w), or from about 1.8% (w/w) to about 3.4% (w/w), or from about 2.2% (w/w) to about 3% (w/w). In some embodiments, CBD is present in an amount of about 0.1, 0.2, 0.4, 0.6, 0.8, 1, 1.2, 1.4, 1.6, 1.8, 2, 2.2, 2.4, 2.6, 2.8, or 3% (w/w). In some embodiments, oils containing about 0.1-5% (w/w) CBD (or other ranges between about 0.1% and about 5%) are prepared using a *cannabis* strain selected from Blueberry and Prize Cush. In some embodiments, oils containing about 0.1-5% (w/w) CBD (or other ranges between about 0.1% and about 5%) are prepared using the Blueberry *cannabis* strain.

In some embodiments, CBD is present in an amount ranging from about 25% (w/w) to about 30% (w/w), or from about 30% (w/w) to about 35% (w/w), or from about 35% (w/w) to about 40% (w/w), or from about 40% (w/w) to about 45% (w/w), or from about 45% (w/w) to about 50% (w/w), or from about 50% (w/w) to about 55% (w/w). In some embodiments, CBD is present in an amount ranging from about 25% (w/w) to about 55% (w/w), or from about 28% (w/w) to about 52% (w/w), or from about 31% (w/w) to about 49% (w/w), or from about 34% (w/w) to about 46% (w/w), or from about 37% (w/w) to about 43% (w/w). In some embodiments, CBD is present in an amount of about 30, 31, 32, 33, 34, 35, 36, 37, 38, 39, 40, 41, 42, 43, 44, 45, 46, 47, 48, 49, or 50% (w/w). In some embodiments, oils containing about 25-55% (w/w) CBD (or other ranges between about 25% and about 55%) are prepared using a *cannabis* strain selected from Cannatonic, Medihaze, and Harlequin. In some embodiments, oils containing about 25-55% (w/w) CBD (or other ranges between about 25% and about 55%) are prepared using the Cannatonic *cannabis* strain.

In some embodiments, CBD is present in an amount ranging from about from about 50% (w/w) to about 55% (w/w), or from about 55% (w/w) to about 60% (w/w), or from about 60% (w/w) to about 65% (w/w), or from about 65% (w/w) to about 70% (w/w), or from about 70% (w/w) to about 75% (w/w), or from about 75% (w/w) to about 80% (w/w). In some embodiments, CBD is present in an amount from about 50% (w/w) to about 80% (w/w), or from about 53% (w/w) to about 77% (w/w), or from about 56% (w/w) to about 74% (w/w), or from about 59% (w/w) to about 71% (w/w), or from about 62% (w/w) to about 68% (w/w). In some embodiments, CBD is present in an amount of about 51, 52, 53, 54, 55, 56, 57, 58, 59, 60, 61, 62, 63, 64, 65, 66, 67, 68, 69, or 70% (w/w). In some embodiments, oils containing about 50-80% (w/w) CBD (or other ranges between about 50% and about 80%) are prepared using a *cannabis* strain selected from Cannatonic, Harle OG, Harle Tsu, and AC/DC. In some embodiments, oils containing about 50-80% (w/w) CBD (or other ranges between about 50% and about 80%) are prepared using the AC/DC *cannabis* strain.

Typically, CBG will be present in an oil of the invention in an amount ranging from about 0.1% (w/w) to about 80% (w/w). In some embodiments, CBG is present in an amount ranging from about 0.1% (w/w) to about 0.2% (w/w), or from about 0.2% (w/w) to about 0.6% (w/w), or from about 0.6% (w/w) to about 1% (w/w), or from about 1% (w/w) to about 1.4% (w/w), or from about 1.4% (w/w) to about 1.8% (w/w), or from about 1.8% (w/w) to about 2.2% (w/w), or from about 2.2% (w/w) to about 2.6% (w/w), or from about 2.6% (w/w) to about 3% (w/w), or from about 3% (w/w) to about 3.4% (w/w), or from about 3.4% (w/w) to about 3.8% (w/w), or from about 3.8% (w/w) to about 4.2% (w/w), or from about 4.2% (w/w) to about 4.6% (w/w), or from about 4.6% (w/w) to about 5% (w/w). In some embodiments, CBG is present in an amount ranging from about 0.2% (w/w) to about 5% (w/w), or from about 0.6% (w/w) to about 4.6% (w/w), or from about 1% (w/w) to about 4.2% (w/w), or from about 1.4% (w/w) to about 3.8% (w/w), or from about 1.8% (w/w) to about 3.4% (w/w), or from about 2.2% (w/w) to about 3% (w/w). In some embodiments, CBG is present in an amount of about 0.1, 0.2, 0.4, 0.6, 0.8, 1, 1.2, 1.4, 1.6, 1.8, 2, 2.2, 2.4, 2.6, 2.8, or 3% (w/w). In some embodiments, oils containing about 0.1-5% (w/w) CBG (or other ranges between about 0.1% and about 5%) are prepared using a *cannabis* strain selected from AC/DC, Cannatonic, and Blueberry.

In general, acidic cannabinoids (such as THCA, CBDA, CBGA, and other acidic cannabinoids) are present in the oils of the present invention (e.g., *cannabis* oil extracts or compositions comprising same) in amounts ranging from about 0.001% (w/w) to about 80% (w/w). In some embodiments, an acidic cannabinoid (such as THCA, CBDA, CBGA, or another acidic cannabinoid) will be present in an amount ranging from about 0.001% (w/w) to about 50% (w/w). An acidic cannabinoid (such as THCA, CBDA, CBGA, or another acidic cannabinoid) can be present, for example, in an amount ranging from about 0.01% (w/w) to about 0.05% (w/w), or from about 0.05% (w/w) to about 0.1% (w/w), or from about 0.1% (w/w) to about 0.2% (w/w), or from about 0.2% (w/w) to about 0.3% (w/w), or from about 0.3% (w/w) to about 0.4% (w/w), or from about 0.4% (w/w) to about 0.5% (w/w), or from about 0.5% (w/w) to about 0.6% (w/w), or from about 0.6% (w/w) to about 0.7% (w/w), or from about 0.7% (w/w) to about 0.8% (w/w), or from about 0.8% (w/w) to about 0.9% (w/w), or from about 0.9% (w/w) to about 1% (w/w), or from about 1% (w/w) to about 5% (w/w), or from about 5% (w/w) to about 10% (w/w), or from about 10% (w/w) to about 15% (w/w), or from about 15% (w/w) to about 20% (w/w), or from about 20% (w/w) to about 25% (w/w), or from about 25% (w/w) to about 30% (w/w), or from about 30% (w/w) to about 35% (w/w), or from about 35% (w/w) to about 40% (w/w), or from about 40% (w/w) to about 45% (w/w), or from about 45% (w/w) to about 50% (w/w), or from about 50% (w/w) to about 55% (w/w), or from about 55% (w/w) to about 60% (w/w), or from about 60% (w/w) to about 65% (w/w), or from about 65% (w/w) to about 70% (w/w), or from about 70% (w/w) to about 75% (w/w), or from about 75% (w/w) to about 80% (w/w).

An acidic cannabinoid (such as THCA, CBDA, CBGA, or another acidic cannabinoid) can be present in an amount ranging from about 0.01% (w/w) to about 1% (w/w), or from about 0.02% (w/w) to about 0.9% (w/w), or from about 0.03% (w/w) to about 0.8% (w/w), or from about 0.04% (w/w) to about 0.7% (w/w), or from about 0.05% (w/w) to about 0.6% (w/w), or from about 0.06% (w/w) to about 0.5% (w/w), or from about 0.07% (w/w) to about 0.4% (w/w), or from about 0.08% (w/w) to about 0.3% (w/w), or from about 0.09% (w/w) to about 0.2% (w/w). An acidic cannabinoid (such as THCA, CBDA, CBGA, or another acidic cannabinoid) can be present in an amount ranging from about 1% (w/w) to about 10% (w/w), or from about 2% (w/w) to about 9% (w/w), or from about 3% (w/w) to about 8% (w/w), or from about 4% (w/w) to about 7% (w/w), or from about 5% (w/w) to about 6% (w/w).

An acidic cannabinoid (such as THCA, CBDA, CBGA, or another acidic cannabinoid) can be present in an amount ranging from about 5% (w/w) to about 50% (w/w), or from about 8% (w/w) to about 48% (w/w), or from about 10% (w/w) to about 46% (w/w), or from about 12% (w/w) to about 44% (w/w), or from about 14% (w/w) to about 42% (w/w), or from about 16% (w/w) to about 40% (w/w), or from about 18% (w/w) to about 38% (w/w), or from about 20% (w/w) to about 36% (w/w), or from about 22% (w/w) to about 34% (w/w), or from about 24% (w/w) to about 32% (w/w), or from about 26% (w/w) to about 30% (w/w). An acidic cannabinoid (such as THCA, CBDA, CBGA, or another acidic cannabinoid) can be present in an amount ranging from about 50% (w/w) to about 75% (w/w), or from about 52% (w/w) to about 74% (w/w), or from about 54% (w/w) to about 72% (w/w), or from about 56% (w/w) to about 70% (w/w), or from about 58% (w/w) to about 68% (w/w), or from about 60% (w/w) to about 66% (w/w), or from about 62% (w/w) to about 64% (w/w).

A. Terpenes

As noted above, *cannabis* oils of the present invention (e.g., *cannabis* oil extracts or compositions comprising same) generally contain at least one terpene compound. Terpenes are hydrocarbon compounds having carbon skeletons derived from isoprene (i.e., $CH_2=C(CH_3)CH=CH_2$). Carbon atoms in the terpene backbone can bear oxygen substituents such as hydroxyl, oxo, and carboxy groups. Terpenes present in the *cannabis* oils of the invention include, but are not limited to, $C_5$ hemiterpenes, $C_{10}$ monoterpenes, $C_{15}$ sesquiterpenes, $C_{20}$ diterpenes, and combinations thereof. Examples of terpenes include, but are not limited to: β-caryophyllene [(1R,4E,9S)-4,11,11-trimethyl-8-methylene-bicyclo(7.2.0)undec-4-ene]; β-caryophyllene oxide; citronellol [3,7-dimethyl-6-octen-1-ol]; α-eudesmol [2-[(2R,4aR)-4a,8-dimethyl-2,3,4,5,6,8a-hexahydro-1H-naphthalen-2-yl]propan-2-ol]; β-eudesmol [2-[(2R,4aR,8aS)-4a-methyl-8-methylidene-1,2,3,4,5,6,7,8a-octahydronaphthalen-2-yl]propan-2-ol]; γ-eudesmol [2-[(2R,4aR)-4a,8-dimethyl-2,3,4,5,6,7-hexahydro-1H-naphthalen-2-yl]propan-2-ol]; geraniol [(2E)-3,7-dimethylocta-2,6-dien-1-ol]; guaiol [2-[(3S,5R,8S)-3,8-dimethyl-1,2,3,4,5,6,7,8-octahydroazulen-5-yl]propan-2-ol]; α-humulene [(1E,4E,8E)-2,6,6,9-tetramethylcycloundeca-1,4,8-triene]; β-humulene [(1E,5E)-1,4,4-trimethyl-8-methylidenecycloundeca-1,5-diene]; γ-humulene [(1Z,6E)-1,8,8-trimethyl-5-methylidenecycloundeca-1,6-diene]; D-limonene [(4R)-1-methyl-4-prop-1-en-2-ylcyclohexene]; L-limonene [(4S)-1-methyl-4-prop-1-en-2-ylcyclohexene]; (−)-linalool [(3R)-3,7-dimethylocta-1,6-dien-3-ol]; (+)-linalool [(3S)-3,7-dimethylocta-1,6-dien-3-ol]; α-myrcene [2-methyl-6-methylideneocta-1,7-diene]; β-myrcene [7-methyl-3-methylideneocta-1,6-diene]; nerol [(2Z)-3,7-dimethylocta-2,6-dien-1-ol]; cis-nerolidol [(6Z)-3,7,11-trimethyldodeca-1,6,10-trien-3-ol]; trans-nerolidol [(6E)-3,7,11-trimethyldodeca-1,6,10-trien-3-ol]; α-ocimene [(3E)-3,7-dimethylocta-1,3,7-triene]; β-ocimene [(3E)-3,7-dimethylocta-1,3,6-triene]; p-cymene [1-methyl-4-(1-methylethyl)benzene]; α-phellandrene [2-methyl-5-propan-2-ylcyclohexa-1,3-diene]; β-phellandrene [3-methylidene-6-propan-2-ylcyclohexene]; cis-phytol [(Z,7R,11R)-3,7,11,15-tetramethylhexadec-2-en-1-ol]; trans-phytol [(E,7R,11R)-3,7,11,15-tetramethylhexadec-2-en-1-ol]; (−)-α-pinene [(1S,5S)-4,6,6-trimethylbicyclo[3.1.1]hept-3-ene]; (−)-3-pinene [(1S,5S)-6,6-dimethyl-4-methylidenebicyclo[3.1.1]heptane]; (+)-α-pinene [(1R,5R)-4,6,6-trimethylbicyclo[3.1.1]hept-3-ene]; (+)-3-pinene [(1R,5R)-6,6-dimethyl-4-methylidenebicyclo[3.1.1]heptane]; (−)-pulegone [(5S)-5-methyl-2-propan-2-ylidenecyclohexan-1-one]; (+)-pulegone [(5R)-5-methyl-2-propan-2-ylidenecyclohexan-1-one]; α-terpinene [1-methyl-4-propan-2-ylcyclohexa-1,3-diene]; δ-terpinene [5-methyl-2-propan-2-ylcyclohexa-1,3-diene]; γ-terpinene [1-methyl-4-propan-2-ylcyclohexa-1,4-diene]; α-terpineol [2-(4-methylcyclohex-3-en-1-yl)propan-2-ol]; γ-terpineol [1-methyl-4-propan-2-ylidenecyclohexan-1-ol]; (+)-valencene [(3R,4aS,5R)-4a,5-dimethyl-3-prop-1-en-2-yl-2,3,4,5,6,7-hexahydro-1H-naphthalene]; and combinations thereof.

In some embodiments, the invention provides an oil containing one more terpenes selected from β-myrcene, linalool, α-terpineol, β-caryophyllene, β-caryophyllene oxide, α-humulene, valencene, cis-nerolidol, guaiol, α-eudesmol, β-eudesmol, γ-eudesmol, and α-bisabolol. In some embodiments, the oil contains one or more terpenes selected from linalool, β-caryophyllene, β-caryophyllene oxide, α-humulene, cis-nerolidol, guaiol, α-eudesmol, and α-bisabolol.

In general, terpenes are present in the oils of the invention in total amounts ranging from about 0.1% (w/w) to about 15% (w/w). For example, the total terpene content can range from about 0.1% (w/w) to about 0.2% (w/w), or from about 0.2% (w/w) to about 0.3% (w/w), or from about 0.3% (w/w) to about 0.4% (w/w), or from about 0.4% (w/w) to about 0.5% (w/w), or from about 0.5% (w/w) to about 0.6% (w/w), or from about 0.6% (w/w) to about 0.7% (w/w), or from about 0.7% (w/w) to about 0.8% (w/w), or from about 0.8% (w/w) to about 0.9% (w/w), or from about 0.9% (w/w) to about 1% (w/w). The total terpene content can range from about 1% (w/w) to about 2% (w/w), or from about 2% (w/w) to about 3% (w/w), or from about 3% (w/w) to about 4% (w/w), or from about 4% (w/w) to about 5% (w/w), or from about 5% (w/w) to about 6% (w/w), or from about 6% (w/w) to about 7% (w/w), or from about 7% (w/w) to about 8% (w/w), or from about 8% (w/w) to about 9% (w/w), or from about 9% (w/w) to about 10% (w/w), or from about 10% (w/w) to about 11% (w/w), or from about 11% (w/w) to about 12% (w/w), or from about 12% (w/w) to about 13% (w/w), or from about 13% (w/w) to about 14% (w/w), or from about 14% (w/w) to about 15% (w/w).

In some embodiments, the invention provides oils with total terpene content ranging from about 0.1% (w/w) to about 1% (w/w), or from about 0.2% (w/w) to about 0.9% (w/w), or from about 0.3% (w/w) to about 0.8% (w/w), or from about 0.4% (w/w) to about 0.7% (w/w), or from about 0.5% (w/w) to about 0.6% (w/w). In some embodiments, the total terpene content ranges from about 1% (w/w) to about 15% (w/w), or from about 2% (w/w) to about 13% (w/w), or from about 3% (w/w) to about 11% (w/w), or from about 4% (w/w) to about 9% (w/w), or from about 5% (w/w) to about 7% (w/w).

In some embodiments, the invention provides oils wherein linalool is present in an amount ranging from about 0% (w/w) to about 0.1% (w/w), or from about 0.1% (w/w) to about 0.2% (w/w), or from about 0.2% (w/w) to about 0.3% (w/w), or from about 0.3% (w/w) to about 0.4% (w/w). In some embodiments, the invention provides oils wherein linalool is present in an amount ranging from about 0.4% (w/w) to about 0.6% (w/w), or from about 0.6% (w/w) to about 0.9% (w/w), or from about 0.9% (w/w) to about 1.2% (w/w), or from about 1.2% (w/w) to about 1.5% (w/w), or from about 1.5% (w/w) to about 1.8% (w/w), or from about 1.8% (w/w) to about 2.1% (w/w), or from about 2.1% (w/w) to about 2.4% (w/w), or from about 2.4% (w/w) to about 2.7% (w/w), or from about 2.7% (w/w) to about 3% (w/w).

In some embodiments, the invention provides oils wherein β-caryophyllene is present in an amount ranging from about 0.2% (w/w) to about 0.3% (w/w), or from about 0.3% (w/w) to about 0.4% (w/w), or from about 0.4% (w/w) to about 0.5% (w/w), or from about 0.5% (w/w) to about 0.6% (w/w), or from about 0.6% (w/w) to about 0.7% (w/w), or from about 0.7% (w/w) to about 0.8% (w/w), or from about 0.8% (w/w) to about 0.9% (w/w), or from about 0.9% (w/w) to about 1.0% (w/w), or from about 1.0% (w/w) to about 1.1% (w/w). In some embodiments, the invention provides oils wherein β-caryophyllene is present in an amount ranging from about 1.1% (w/w) to about 1.5% (w/w), or from about 1.5% (w/w) to about 1.8% (w/w), or from about 1.8% (w/w) to about 2.1% (w/w), or from about 2.1% (w/w) to about 2.4% (w/w), or from about 2.4% (w/w) to about 2.7% (w/w), or from about 2.7% (w/w) to about 3% (w/w).

In some embodiments, the invention provides oils wherein α-humulene is present in an amount ranging from about 0.1% (w/w) to about 0.2% (w/w), or from about 0.2% (w/w) to about 0.3% (w/w), or from about 0.3% (w/w) to about 0.4% (w/w), or from about 0.4% (w/w) to about 0.5% (w/w), or from about 0.5% (w/w) to about 0.6% (w/w). In some embodiments, the invention provides oils wherein α-humulene is present in an amount ranging from about 0.6% (w/w) to about 0.9% (w/w), or from about 0.9% (w/w) to about 1.2% (w/w), or from about 1.2% (w/w) to about 1.5% (w/w), or from about 1.5% (w/w) to about 1.8% (w/w), or from about 1.8% (w/w) to about 2.1% (w/w), or from about 2.1% (w/w) to about 2.4% (w/w), or from about 2.4% (w/w) to about 2.7% (w/w), or from about 2.7% (w/w) to about 3% (w/w).

In some embodiments, the invention provides oils wherein cis-nerolidol is present in an amount ranging from about 0.1% (w/w) to about 0.2% (w/w), or from about 0.2% (w/w) to about 0.3% (w/w), or from about 0.3% (w/w) to about 0.4% (w/w), or from about 0.4% (w/w) to about 0.5% (w/w), or from about 0.5% (w/w) to about 0.6% (w/w), or from about 0.6% (w/w) to about 0.7% (w/w), or from about 0.7% (w/w) to about 0.8% (w/w), or from about 0.8% (w/w) to about 0.9% (w/w). In some embodiments, the invention provides oils wherein cis-nerolidol is present in an amount ranging from about 0.9% (w/w) to about 1.2% (w/w), or from about 1.2% (w/w) to about 1.5% (w/w), or from about 1.5% (w/w) to about 1.8% (w/w), or from about 1.8% (w/w) to about 2.1% (w/w), or from about 2.1% (w/w) to about 2.4% (w/w), or from about 2.4% (w/w) to about 2.7% (w/w), or from about 2.7% (w/w) to about 3% (w/w).

In some embodiments, the invention provides oils wherein β-caryophyllene oxide is present in an amount ranging from about 0.1% (w/w) to about 0.2% (w/w), or from about 0.2% (w/w) to about 0.3% (w/w), or from about 0.3% (w/w) to about 0.4% (w/w). In some embodiments, the invention provides oils wherein β-caryophyllene oxide is present in an amount ranging from about 0.4% (w/w) to about 0.6% (w/w), or from about 0.6% (w/w) to about 0.9% (w/w), or from about 0.9% (w/w) to about 1.2% (w/w), or from about 1.2% (w/w) to about 1.5% (w/w), or from about 1.5% (w/w) to about 1.8% (w/w), or from about 1.8% (w/w) to about 2.1% (w/w), or from about 2.1% (w/w) to about 2.4% (w/w), or from about 2.4% (w/w) to about 2.7% (w/w), or from about 2.7% (w/w) to about 3% (w/w).

In some embodiments, the invention provides oils wherein guaiol is present in an amount ranging from about 0.0% (w/w) to about 0.1% (w/w), or from about 0.1% (w/w) to about 0.2% (w/w), or from about 0.2% (w/w) to about 0.3% (w/w), or from about 0.3% (w/w) to about 0.4% (w/w), or from about 0.4% (w/w) to about 0.5% (w/w), or from about 0.5% (w/w) to about 0.6% (w/w), or from about 0.6% (w/w) to about 0.7% (w/w). In some embodiments, the invention provides oils wherein guaiol is present in an amount ranging from about 0.7% (w/w) to about 0.9% (w/w), or from about 0.9% (w/w) to about 1.2% (w/w), or from about 1.2% (w/w) to about 1.5% (w/w), or from about 1.5% (w/w) to about 1.8% (w/w), or from about 1.8% (w/w) to about 2.1% (w/w), or from about 2.1% (w/w) to about 2.4% (w/w), or from about 2.4% (w/w) to about 2.7% (w/w), or from about 2.7% (w/w) to about 3% (w/w).

In some embodiments, the invention provides oils wherein β-eudesmol is present in an amount ranging from about 0.0% (w/w) to about 0.1% (w/w), or from about 0.1% (w/w) to about 0.2% (w/w), or from about 0.2% (w/w) to about 0.3% (w/w), or from about 0.3% (w/w) to about 0.4% (w/w), or from about 0.4% (w/w) to about 0.6% (w/w). In some embodiments, the invention provides oils wherein β-eudesmol is present in an amount ranging from about 0.6% (w/w) to about 0.9% (w/w), or from about 0.9% (w/w) to about 1.2% (w/w), or from about 1.2% (w/w) to about 1.5% (w/w), or from about 1.5% (w/w) to about 1.8% (w/w), or from about 1.8% (w/w) to about 2.1% (w/w), or from about 2.1% (w/w) to about 2.4% (w/w), or from about 2.4% (w/w) to about 2.7% (w/w), or from about 2.7% (w/w) to about 3% (w/w).

In some embodiments, the invention provides oils wherein α-bisalobol is present in an amount ranging from about 0.0% (w/w) to about 0.1% (w/w), or from about 0.1% (w/w) to about 0.2% (w/w), or from about 0.2% (w/w) to about 0.3% (w/w), or from about 0.3% (w/w) to about 0.4% (w/w), or from about 0.4% (w/w) to about 0.5% (w/w), or from about 0.5% (w/w) to about 0.6% (w/w), or from about 0.6% (w/w) to about 0.7% (w/w), or from about 0.7% (w/w) to about 0.8% (w/w), or from about 0.8% (w/w) to about 0.9% (w/w), or from about 0.9% (w/w) to about 1.0% (w/w), or from about 1.0% (w/w) to about 1.1% (w/w). In some embodiments, the invention provides oils wherein α-bisalobol is present in an amount ranging from about 1.1% (w/w) to about 1.5% (w/w), or from about 1.5% (w/w) to about 1.8% (w/w), or from about 1.8% (w/w) to about 2.1% (w/w), or from about 2.1% (w/w) to about 2.4% (w/w), or from about 2.4% (w/w) to about 2.7% (w/w), or from about 2.7% (w/w) to about 3% (w/w).

In some embodiments the invention provides a *cannabis* oil prepared from the AC/DC *cannabis* strain, wherein the oil contains: THC in an amount ranging from about 1% (w/w) to about 3% (w/w); CBD in an amount ranging from about 58% (w/w) to about 66% (w/w); CBG in an amount ranging from 2% (w/w) to about 4% (w/w); and CBN in an amount ranging from about 0.05% (w/w) to about 0.15% (w/w). In some embodiments, the *cannabis* oil prepared from the AC/DC *cannabis* strain further contains CBDA in an amount ranging from about 0.2% (w/w) to about 0.9% (w/w).

In some embodiments, the *cannabis* oil prepared from the AC/DC *cannabis* strain further contains linalool in an amount ranging from about 0.1% (w/w) to about 0.3% (w/w). In some embodiments, the *cannabis* oil prepared from the AC/DC *cannabis* strain further contains β-caryophyllene in an amount ranging from about 0.5% (w/w) to about 0.9% (w/w). In some embodiments, the *cannabis* oil prepared from the AC/DC *cannabis* strain further contains β-caryophyllene oxide in an amount ranging from about 0.01% (w/w) to about 0.3% (w/w). In some embodiments, the *cannabis* oil prepared from the AC/DC *cannabis* strain further contains α-humulene in an amount ranging from about 0.2% (w/w) to about 0.5% (w/w). In some embodiments, the *cannabis* oil prepared from the AC/DC *cannabis* strain further contains cis-nerolidol in an amount ranging from about 0.1% (w/w) to about 0.3% (w/w). In some embodiments, the *cannabis* oil prepared from the AC/DC *cannabis* strain further contains guaiol in an amount ranging from about 0.3% (w/w) to about 0.7% (w/w). In some embodiments, the *cannabis* oil prepared from the AC/DC *cannabis* strain further contains α-eudesmol in an amount ranging from about 0.4% (w/w) to about 0.5% (w/w). In some embodiments, the *cannabis* oil prepared from the AC/DC *cannabis* strain further contains β-eudesmol in an amount ranging from about 0.3% (w/w) to about 0.4% (w/w). In some embodiments, the *cannabis* oil prepared from the AC/DC *cannabis* strain further contains γ-eudesmol in an amount ranging from about 0.1% (w/w) to about 0.2% (w/w). In some embodiments, the *cannabis* oil prepared from the AC/DC *cannabis* strain further contains α-bisabolol in an amount ranging from about 0.8% (w/w) to about 1.1% (w/w). In some such embodiments, the *cannabis* oil prepared from the AC/DC *cannabis* strain contains terpenes in a total amount ranging from about 4% (w/w) to about 7% (w/w).

In some embodiments the invention provides a *cannabis* oil prepared from the Cannatonic *cannabis* strain, wherein the oil contains: THC in an amount ranging from about 2% (w/w) to about 40% (w/w); CBD in an amount ranging from about 30% (w/w) to about 70% (w/w); CBG in an amount ranging from 1% (w/w) to about 4% (w/w); and CBN in an amount ranging from about 0.01% (w/w) to about 2% (w/w). In some embodiments, the *cannabis* oil prepared from the Cannatonic *cannabis* strain further contains CBDA in an amount ranging from about 0.01% (w/w) to about 0.3% (w/w). In some embodiments, the *cannabis* oil prepared from the Cannatonic *cannabis* strain further contains CBGA in an amount ranging from about 0.07% (w/w) to about 0.3% (w/w).

In some embodiments, the *cannabis* oil prepared from the Cannatonic *cannabis* strain further contains linalool in an amount ranging from about 0.1% (w/w) to about 0.3% (w/w). In some embodiments, the *cannabis* oil prepared from the Cannatonic *cannabis* strain further contains β-caryophyllene in an amount ranging from about 0.5% (w/w) to about 0.7% (w/w). In some embodiments, the *cannabis* oil prepared from the Cannatonic *cannabis* strain further contains α-humulene in an amount ranging from about 0.3% (w/w) to about 0.4% (w/w). In some embodiments, the *cannabis* oil prepared from the Cannatonic *cannabis* strain further contains cis-nerolidol in an amount ranging from about 0.1% (w/w) to about 0.3% (w/w). In some embodiments, the *cannabis* oil prepared from the Cannatonic *cannabis* strain further contains guaiol in an amount ranging from about 0.2% (w/w) to about 0.4% (w/w). In some embodiments, the *cannabis* oil prepared from the Cannatonic *cannabis* strain further contains α-eudesmol in an amount ranging from about 0.1% (w/w) to about 0.3% (w/w). In some embodiments, the *cannabis* oil prepared from the Cannatonic *cannabis* strain further contains β-eudesmol in an amount ranging from about 0.1% (w/w) to about 0.2% (w/w). In some embodiments, the *cannabis* oil prepared from the Cannatonic *cannabis* strain further contains α-bisabolol in an amount ranging from about 0.1% (w/w) to about 0.3% (w/w). In some such embodiments, the *cannabis* oil prepared from the Cannatonic *cannabis* strain contains terpenes in a total amount ranging from about 0.5% (w/w) to about 3.5% (w/w).

In some embodiments the invention provides a *cannabis* oil prepared from the Blueberry *cannabis* strain, wherein the oil contains: THC in an amount ranging from about 60% (w/w) to about 80% (w/w); CBD in an amount ranging from about 0.5% (w/w) to about 2.5% (w/w); CBG in an amount ranging from 1% (w/w) to about 2% (w/w); and CBN in an amount ranging from about 0.5% (w/w) to about 1.5% (w/w). In some embodiments, the *cannabis* oil prepared from the Blueberry *cannabis* strain further contains THCA in an amount ranging from about 0.1% (w/w) to about 0.5% (w/w). In some embodiments, the *cannabis* oil prepared from the Blueberry *cannabis* strain further contains CBDA in an amount ranging from about 0.01% (w/w) to about 0.3% (w/w). In some embodiments, the *cannabis* oil prepared from the Blueberry *cannabis* strain further contains CBGA in an amount ranging from about 0.1% (w/w) to about 0.5% (w/w).

In some embodiments, the *cannabis* oil prepared from the Blueberry *cannabis* strain further contains linalool in an amount ranging from about 0.3% (w/w) to about 0.4% (w/w). In some embodiments, the *cannabis* oil prepared from the Blueberry *cannabis* strain further contains α-terpineol in an amount ranging from about 0.1% (w/w) to about 0.2% (w/w). In some embodiments, the *cannabis* oil prepared from the Blueberry *cannabis* strain further contains β-caryophyllene in an amount ranging from about 0.7% (w/w) to about 1.0% (w/w). In some embodiments, the *cannabis* oil prepared from the Blueberry *cannabis* strain further contains β-caryophyllene oxide in an amount ranging from about 0.1% (w/w) to about 0.2% (w/w). In some embodiments, the *cannabis* oil prepared from the Blueberry *cannabis* strain further contains α-humulene in an amount ranging from about 0.4% (w/w) to about 0.6% (w/w). In some embodiments, the *cannabis* oil prepared from the Blueberry *cannabis* strain further contains valencene in an amount ranging from about 0.1% (w/w) to about 0.2% (w/w). In some embodiments, the *cannabis* oil prepared from the Blueberry *cannabis* strain further contains cis-nerolidol in an amount ranging from about 0.4% (w/w) to about 0.6% (w/w). In some embodiments, the *cannabis* oil prepared from the Blueberry *cannabis* strain further contains α-eudesmol in an amount ranging from about 0.1% (w/w) to about 0.2% (w/w). In some such embodiments, the *cannabis* oil prepared from the Blueberry *cannabis* strain contains terpenes in a total amount ranging from about 3% (w/w) to about 5% (w/w).

Experimental procedures for determining the cannabinoid and terpene composition of the strains of *cannabis* used in the disclosure herein can be performed using known techniques in the art. The extract, any aliquot taken during the extraction procedure, or the plant material itself can be used in any of the quantitative analysis techniques used. Those techniques include, but are not limited to, liquid chromatography, mass spectrometry, and gas chromatography. A person of skill in the art will recognize that there are many other techniques available to determine cannabinoid and terpene composition of the *cannabis* strains used herein.

B. Essential Oils and Other Additives

In certain embodiments, one or more essential oils are added to the extracted *cannabis* oil to provide properties such as improved palatability. Essential oils can also provide antioxidant and preservative properties in the *cannabis* oil compositions. The identity and amount of the essential oil(s) added can depend in part on factors including the strain of *cannabis* that has been extracted and the desired organoleptic properties. In general, the amount of total essential oils added to a *cannabis* extract will range from about 0.01% (w/w) to about 10% (w/w) or more. The total amount of essential oils added can range, for example, from about 0.01% (w/w) to about 0.5% (w/w), or from about 0.5% (w/w) to about 1% (w/w), or from about 1% (w/w) to about 2% (w/w), or from about 2% (w/w) to about 3% (w/w), or from about 3% (w/w) to about 4% (w/w), or from about 4% (w/w) to about 5% (w/w), or from about 5% (w/w) to about 6% (w/w), or from about 6% (w/w) to about 7% (w/w), or from about 7% (w/w) to about 8% (w/w), or from about 8% (w/w) to about 9% (w/w), or from about 9% (w/w) to about 10% (w/w). In some embodiments, the amount of total essential oils added is about 0.05% (w/w). In some embodiments, the total amount of essential oils added is about 1.7% (w/w). In some embodiments, the total amount of essential oils added is about 2.5% (w/w). The % (w/w) values indicated are based on the amount of essential oil added to the amount of total *cannabis* extract (including vitamin E or additives other than the essential oil, if applicable).

In some embodiments, the *cannabis* oil extract includes one or more added essential oils selected from bergamot essential oil, blood orange essential oil, neroli essential oil, peppermint essential oil, and spearmint essential oil. In some embodiments, the *cannabis* oil extract includes Vitamin E and one or more essential oils selected from bergamot essential oil, blood orange essential oil, neroli essential oil, peppermint essential oil, and spearmint essential oil.

In some embodiments, the *cannabis* oil extract includes one or more added essential oils selected from bergamot essential oil, blood orange essential oil, and neroli essential oil. In some embodiments, the *cannabis* oil extract includes Vitamin E and one or more added essential oils selected from bergamot essential oil, blood orange essential oil, and neroli essential oil.

In some embodiments, the *cannabis* oil extract includes one or more added essential oils selected from peppermint essential oil and spearmint essential oil. In some embodiments, the *cannabis* oil extract includes Vitamin E and one or more added essential oils selected from peppermint essential oil and spearmint essential oil.

In some embodiments, the *cannabis* oil extract includes one or more added essential oils selected from a lavender essential oil and lemongrass essential oil. In some embodiments, the *cannabis* oil extract includes Vitamin E and one or more added essential oils selected from a lavender essential oil and a lemongrass essential oil.

In some embodiments, the *cannabis* oil extract includes one or more added essential oils selected from Sweet Orange (*Citrus sinensis* spp), Peppermint (*Mentha piperita* spp), Lemon (*Citrus limon* spp), Lavender (*Lavendula angustifolia* spp) and *Vanilla* (*Vanilla planifolia* spp). In some embodiments, the *cannabis* oil extract includes Vitamin E and one or more essential oils selected from Sweet Orange (*Citrus sinensis* spp), Peppermint (*Mentha piperita* spp), Lemon (*Citrus limon* spp), Lavender (*Lavendula angustifolia* spp) and *Vanilla* (*Vanilla planifolia* spp).

Other essential oils that can be used in the compositions of the invention include, but are not limited to: Agarwood; Agarwood Attar; Ahibero; Allspice; Almond, bitter; Amber Oil; Ambrette Seed; Amyris; *Angelica* Root; *Angelica* Seed; Aniseed; Anise; Anise (star); Armoise (Mugwort); *Artemisia vestita*; Asafoetida; Bakul; Balsam of Peru Oil; Balsam of Peru Resin; Balsamite; Baobab Oil; Basil, Sweet ct Linalool; Basil, Sweet ct Linalool—Organic; Basil, Sweet ct Methyl Chavicol—Organic; Bay; Beeswax; Bergamot; Birch; Boldo; *Boronia*; Black Cumin; Black Currant Bud; Blue Lotus Attar; Broom; Buchu; *Bupleurum* (*Bupleurum fruticosum*); Buddha wood; Butter; Cabreuva; Cade; Cajuput; *Calamus*; *Calendula*; Camomile (or Chamomile); Camphor; *Cananga*; Cangerana; Cape Chamomile (*Ericephalus punctulatus*) S. Africa, Wild Harvest; Cape May; Caraway; Caraway; Cardamom; Carnation; Carrot Seed; Cascarilla; *Cassia*; Cassie; Catnip; Cedar (*Cedrus*) India; Cedarwood; Cedarwood, Atlas—Organic; Cedarwood, Himalayan; Cedarwood, Texas; Cedarwood, Virginia; Celery leaf, Celery Seed; Chamomile, Blue; Chamomile; Chamomile, Roman (*Anthemis nobilis*); Champa Attar (*Michelia champaca*) India; Champaca; Chaste tree; Cilantro; Cinnamon; Cinnamon Bark; *Cistus*; *Cistus* (*Cistus ladaniferus*) Corsica; Citronella; Clary Sage Absolute; Clary Sage, Bulgaria; Clary Sage, Russia; Clary Sage, USA; Clementine; Clove; Clove Bud; Cacao; Coconut Pulp; Coffee Bean Oil; Cognac, Green; *Coleus*; Combava (fruit or leaf); Copaiba; Coriander; Coriander Seed; Cucumber Hydrosol; Cumin; Cumin Seed; Cypress Leaf, Cypress, Blue; Davana; Dill; Elemi; *Eucalyptus*, Blue Gum; *Eucalyptus*, Blue Mallee; *Eucalyptus*, Lemon; Fennel (*Foeniculum vulgare*) Bulgaria; Fennel, Sweet; Fenugreek; Fern (sweet); Fleabane; Fir Needle; Fir, Balsam; Fir, Douglas; Fir, Silver; Fragonia; Frankincense, India; Frankincense, Somalia; Frankincense Frereana; Frankincense, Oman; Frankincense, Oman; Frankincense, Somalia; Galangal; *Galbanum*; Geranium; Geranium, Egypt; Geranium, Rose; Geranium, South Africa; Ghandi root; Ginger; Ginger Lily; Ginger, Fresh; Gingergrass (*Cymbopogon martinii*); Goldenrod; Grapefruit, Pink; Grapefruit, Ruby Red; Grapefruit, White; Hay; Helichrysum, Albania; Helichrysum, Croatia; Hina Attar, India; Hop; Hyssop *Decumbens*; Hyssop; Immortelle; Jasmine Absolute, Egypt; Jasmine Absolute, India; Jasmine Concrete; Jasmine; Jasmine Sambac; Jatamansi, (*Nardostachs jatamansi*); Juniper; Juniper Berry (*Juniperus communis*); Juniper Leaf/Berry; Kaffir Lime; Kava Kava; Labdanum; Larch needle; Laurel (*Laurus nobilis*) Corsica; Laurel Leaf, Lavandin, Grosso; Lavender—High Elevation; Lavender—Wild; Lavender Absolute; Lavender Hydrosol; Lavender, Bulgaria; Lavender, France; Lavender, Maillette; Leleshwa; Lemon; Lemon Tea Tree; Lemon *verbena*; Lemongrass; Lentisque (*Pistacia lentiscus*) Corsica; Lime; Lime Essence Oil; Lime, Distilled; *Liquidambar* (*Styrax*); Longoza; Lotus Absolute, Pink; Lotus Absolute, White; Lovage leaf, Lovage root; *Magnolia* flower; Mandarin; Mandarin, Green; Mandarin, Red; Mandarin, Yellow; Mango ginger; Marjoram; Marula oil; *Melissa*; Mint; Mint, Himalayan (*Mentha arvensis*); Mitti Attar; Motia Attar (Jasmine sambac) India; Mugwort; Mustard; Myrrh; Myrtle, Green; Myrtle (*Myrtus Communis*); Nagarmotha (Cypriol); Neem (*Azadirachta indica*) India; Neroli; Niaouli; Nutmeg; Nut grass; Oakmoss Absolute; Oakwood; Opopanax, Sweet Myrrh (*Commiphora guidotti*); Orange, Blood; Orange, Sweet; Orange, Wild; Orange Blossom; Orange Essence Oil; Orange, Bitter Green; Orange, Bitter Red; Oregano; Orris Butter; Osmanthus Absolute; Palmarosa; Palmarosa, Nepal; Palmarosa, Sri Lanka; Palo Santo (*Bursera graveolens*); Palo Santo; Patchouli; Absolute; Patchouli, Dark; Patchouli, Light; Patchouli, Sri Lanka; Pennyroyal; Pepper, Black; Peppercorn, Pink; Peppermint, Chocolate; Peppermint, France; Peppermint, India; Peppermint, USA; Petitgrain Absolute; Petitgrain Bigarade; Petitgrain sur Fleurs; Petitgrain, Mandarin; Pimento; Pine; Pinion Juniper Co-distillation, Colorado, Wild Harvest; Pinon Pine (*Pinus edulis*) Colorado, Wild Harvest; Pitta blend (Lavender, Rose Geranium, Ruh Khus); Plai; Pomegranate Seed; *Rhododendron* (*Rhododendron anthopogon*); Rhododendron Leaf; Rosalina; Rose; Rose Attar; Rose de Mai Absolute; Rose de Mai Concrete; Rose de Mai Organic Extract; Rose geranium; Rose Hip Seed; Rose Otto, Bulgaria; Rose Otto, Turkey; Rose Otto, White—Organic; Rose vetiver; Rosemary Antioxidant; Rosemary ct Cineole; Rosemary ct Verbenone; Rosewood; Rue; Ruh Khus (*Vetiveria zizaniodes*); Saffron Attar, India; Sage; Samphire (*Cristhmum maritimum*) *Corsica*; Sandalwood; Sandalwood, New Caledonia; Sandalwood, Australian—Premium; Sandalwood (*Santalum spicatum*), Australia; Sandalwood Oil, Royal Hawaiian (*Santalum paniculatum*); Sandalwood, Royal Hawaiian; *Sassafras*; Savitri Rose Perfume; Sea Buckthorn; Seaweed; Sierra Juniper (*Juniperus occidentalis*); Spearmint; Spearmint (*Mentha Spicata*) Israel; Spikenard; Spikenard, Green; Spruce, Black; Spruce (*Picea mariana*) Canada; St. John's Wort 2; St. John's Wort (*Hypericum perforatum*) Bulgaria; *Tagetes*; Tamanu (Foraha) Oil; Tangelo; Tangerine; Tangerine Murcott; Tansy; Tansy, Blue; Tarragon; Tea Tree; Tea Tree (*Leptospermum citratum*), Lemon Scented; Tea Tree (*Melaleuca alternifolia*) South Africa; *Thuja*; Thyme; Thyme ct Linalool; Tobacco; Tonka Bean; Tuberose; Tulsi, Holy Basic Oil (*Ocimum sanctum*); Turmeric; Vanilla; Vanilla Bourbon; *Verbena*; Vetiver—Double Distilled; Vetiver, El Salvador; Vetiver, Haiti; Vetiver, Sri Lanka; Violet Leaf; White Fir (*Abies concolor*); White Lotus Attar; White Sage (*Salvia apiana*); Wild Carrot, *Corsica*; Wintergreen; Wintergreen; Yarrow; Yarrow, Blue; Ylang Ylang; Yuzu; and combinations thereof.

The compositions of the invention can also include one or more herbal extracts of Abas, Abele, *Abies balsamea*, Absinthe, *Absinthium, Acacia, Acacia* spp., Acai Berries, Acerola, *Achillea Millefolium*, Achiote, Aconite, Aconitum Napellus, Acorus, *Acorus calamus*, Acorus gramineus, *Adansonia digitata*, Adder's Mouth, Adderwort, Adiantum capillus-veneris, *Aesculus Hippocastanum*, Aframomum melegueta, African Geranium, African Ginger, *Agastache foeniculum*, Agave, Agnus Castus, Agrimonia *Eupatoria*, Agrimony, *Agropyron Repens*, Ague Grass, Ague Root, Ague Tree, Agueweed, Ajamoda, Ajave Seeds, Ajenjo, Ajowan, *Ajuga Reptans*, Ajvain, Ajwan, Ajwain, Akebia, Akebia quinata, Alaskan *Ginseng*, Alchemilla Vulgaris, Alchomea Species, Alder, Alder Buckthorn, Alder Dogwood, Alecost, Alehoof, Aletris, Aletris *Farinosa*, Alexandrian Laurel, Alexandrian *Senna*, Alfalfa, Algarroba, Alkanet, Allheal, Alligator Pepper, *Allium cepa, Allium porrum, Allium sativum, Allium schoenoprasum, Allium tuberosum,* Allspice, Almond, *Alnus glutinosa, Alnus rubra, Aloe ferox,* Aloeroot, Aloes, *Aloe Vera,* Aloysia *triphylla,* Alpine Strawberry, Alpinia *Officinarum,* Althaea, Althaea *Officinalis,* Aluka, Alumroot, *Amara Aromatica,* Amaracus, Amaranth, *Amaranthus* Hypocondriacus, Amber Touch-and-heal, Ambroise, Ambrose, Amburana, America-Hodoimo, American *Aloe,* American *Angelica,* American Ash, American Aspen, American Basswood, American Bayberry, American Bee Balm, American Beech, American Bugleweed, American Carob, American Cranesbill, American Cress, American Dill, American Dogwood, American *Ginseng,* American Ground Lily, American Groundnut, American Linden, American Mandrake, American *Melissa,* American Saffron, American Sanicle, American Sarsaparilla, American Sloe, American Spikenard, American Upland Cotton, American Valerian, American Winter Cress, American Wormroot, American Wormseed, Amla, Ammi Visnaga, *Anacardium Occidentale, Ananas Comosus, Anchusa Officinalis,* Andiroba, *Andrographis, Andrographis paniculata, Anemone, Anemone Pulsatilla, Anemopsis californica, Anethum Graveolens, Angelica, Angelica Archangelica, Angelica Sinensis, Angelica* Tree, Angostura, Angostura *trifoliata,* Anise, Aniseed, Aniseed Stars, Anise Fern, Anise Hyssop, Anise Plant, Annatto, *Annona muricata, Annona reticulata,* Annual Marjoram, *Anthemis Nobilis, Anthoxanthum nitens, Anthriscus cerefolium,* Antilles Cherry, Apios americana, *Apium Graveolens,* Apple, Apple Mint, Apple-of-Peru, Apricot Vine, Apsidium, *Aralia Racemosa,* Arbe a suif, Arberry, Arboloco, Arbor Vitae, *Arbutus, Arbutus menziesii, Arbutus Uva Ursi, Archangel, Archangelica, Archangelica officinalis, Arctium Lappa, Arctostaphylos Uva Ursi,* Ardraka, Argan, Argania, Argania *spinosa, Argemone Mexicana,* Argentine, Aristolochia serpentaria, Aristotelia *chilensis,* Aritha, Arjaka, Arjuna, *Armoracia Rusticana,* Armstrong, *Arnica, Arnica* Flowers, *Arnica Montana,* Amica Root, Aromatic Sumac, Aromatic Wintergreen, Arrowroot, *Artemisia, Artemisia Abrotanum, Artemisia Absinthium, Artemisia capillaris, Artemisia Dracunculus, Artemisia Tridentata, Artemisia Vulgaris, Artocarpus altilis, Artocarpus heterophyllus,* Arugula, Asafoetida, Asclepias *Tuberosa,* Ascophyllum nodosum, Ash, Ashwaganda, Asian *Ginseng,* Aspalathus *Linearis, Asparagus Cochinchinensis, Asparagus racemosus, Asparagus* Root, *Asperula Odorata,* Aspilia, Aspilia Mossambicensis, Ass-ear, Asthma Plant, Asthma Weed, *Astragalus, Astragalus Membranaceus, Atropa belladonna,* Auld Wife's Huid, Autumn *Crocus, Avena Sativa,* Avens, Averrhoa carambola, Avocado, Ayak Chichira, Ayuk Willku, Azadirachta Indica, Azafran, Babchi Seeds, Bacc, Bachelor's-button, Bacopa Monniera, Bahama Berry, Baical Skullcap, Bai Guo, Bai Mu Erh, Ba Ji Tian, Baldina, Balinghoy, Ballota nigra, Balm Mint, Balm of Gilead, Balmony, Balsam Copaiba, Balsam Fir, Balsam of Gilead, Balsam of Peru, Balsam Tree, Bank Cress, Banisteriopsis caapi vine, Baobab, Baptisia, Baptisia *Tinctoria,* Barbados *Aloe,* Barbados Cherry, *Barbarea verna,* Barberry, Barbary Fig, Bardana, Barley, Barosma Betulina, Barren Strawberry, Barun, Basil, Basil Thyme, Basin Sagebrush, Basketbush, Basswood, Bastard Cardamom, Bastard Saffron, Bast Tree, Bauple Nut, Bayawas, Bayberry, Bayberry Bush, Bayberry Wax Tree, Bay Laurel, Beaked Parsley, Bean of India, Bean Trefoil, Bearberry, Bearbind, Beard Lichen, Bear's Foot, Bear's-grape, Bear's-paw, Bear's Weed, Beaumont Root, Beauty Leaf, Bee Balm, Bee Bread, Beech, Beechdrops, Beech Wheat, Bee Plant, Bee Sage, Bee's Nest, Beggar's Buttons, *Belladonna,* Belle Isle Cress, Bellyache Root, Benjamin Bush, Benzoin Gum, Benzoin Tree, Berberidis,

*Berberis Aquifolium, Berberis Vulgaris*, Berberry, Bergamot Mint, Bergamot Orange, Bertholletia *Excelsa, Betel*, Bethroot, Betony, *Betula alba, Betula pendula*, Bhang, Bian Xu, Bible Hyssop, Bible-leaf, Big Sagebrush, Bilberry, Billy-goat Clover, Biltmore Ash, Bindweed, Bird's-foot, Bird's Nest, Birthroot, Birthwort, Biscuits, Bishop's Weed, Bistort, Bitter *Aloe*, Bitter Ash, Bitter Bark, Bitter Dock, Bitter Leaf, Bitter Melon, Bitter Nightshade, Bitter Orange, Bitter Orange Peel, Bitter Quassia, Bittersweet, Bitter Trefoil, Bitter Wood, Bitterworm, *Bixa orellana*, Black Alder, Black Alder Tree, Blackberry, Black Cherry, Black Choke, Black Chokeberry, Black Cohosh, Black Cohush, Blackcurrant, Black Dogwood, Black Ginger, Black Haw, Black Henbane, Black Horehound, Black Locust, Black Mustard, Black Pepper, Black Root, Black Sampson, Black Sanicle, Black Snakeroot, Black Stinking Horehound, Black Tany, Blackthorn, Black Thyme, Black Walnut, Black Whortleberry, Blackwort, Bladder Cherry, Bladder Fucus, Bladderpod, Bladderwrack, Blazing Star, Blessed Herb, Blessed Thistle, Blind Nettle, Bloodroot, Blood Vine, Bloodwort, Blooming Sally, Blow Ball, Blue Balm, Blueberry, Bluebottle, Blue Cohosh, Blue Curls, Blue Dandelion, Blue Flag, Blue Giant Hyssop, Blue *Ginseng*, Blue Gum, Blue Gum Tree, Blue Iris, Blue Mountain Tea, Blue Pimpemel, Blue Rocket, Blue-Sailors, Blue Skullcap, Blue Violet, Blunt-leaved Dock, Bodhi Tree, Bofareira, Bogbean, Bo He, Bola, Boldina, Boldo, Boldoa, Boldu, Boldus, Boneset, Bookoo, Borage, *Borago Officinalis*, Boswellia carteri, Bo-Tree, Bottlebrush, Bouncing Bet, Bourtree, Bowman's Root, Boxberry, Boxwood, Brahmi, Bramble, Brandy Mint, *Brassica alba, Brassica juncea, Brassica nigra, Brassica oleracea, Brassica rapa Pekinensis*, Brazilian *Ginseng*, Brazil Nut, Breadfruit, Bread Wheat, Bride's Button, Bridewort, Brigham Tea, Brindall Berry, Brindle Berry, Brinton Root, British Myrrh, Broad-leaved Dock, Bromelain, Brook Bean, Brooklime, Broom, Broom Flowers, Broom Tops, Broom Tea-Tree, Brown Mustard, Brownwort, Bruisewort, Bryonia Alba, Bryony, Buchu, Buckbean, Buckeye, Buckler-leaved Sorrel, Buckthorn, Buckwheat, Bucku, Buddha Fruit, Buffalo Herb, Bugbane, Bugbane Squawroot, Bugle, Bugleweed, Bugloss, Bu Gu Zhi, Bugwort, Bull Flower, Bullock's Heart, Bull's Heart, Bunny's Ears, *Bupleurum, Bupleurum Chinese*, Bur, Burage, Burdock, Burdock Burrs, Burren Myrtle, Burr Marigoldt, Burrs, Burr Seed, Bush Nut, Butcher's Broom, Butterbur, Butterfly Weed, Butternut, Butter Winter, Butterwort, Butterweed, Buttons, Caban Cherry, Cabbage, Cabbage Palm, Cabbage Rose, Cacao, Cacari, Cajeput Tree, Cajueiro, Calabar Bean, Calamint, Calamintha *Nepeta, Calamus, Calendula, Calendula Officinalis*, California Poppy, *Calluna Vulgaris, Calophyllum inophyllum*, Caltrop, Calumba, Cambodian Mint, Camel Grass, *Cammellia sinensis*, Camocamo, Camphor, Camphor Tree, Camptotheca *Acuminata*, Camu Camu, Canabis, Canada Balsam, Canada Root, Canada Tea, Canadian Fleabane, Canaigre, *Cananga odorata*, Cancerosa, Caner Root, Cancer Tree, Candle Berry, Cane Ash, Canistel Fruit, Cankerwort, *Cannabis Sativa*, Cape *Aloe*, Cape Gooseberry, Caperberry, Caperbush, Capers, Capon's Tail, *Capparis spinosa*, Capsaicin, *Capsella Bursa-Pastoris, Capsicum, Capsicum Annuum, Capsicum chinense*, Carambola, *Carapa guianensis*, Caraway, Caraway Seed, Cardamom, Cardamom Seeds, Cardamon, *Carduus* Marianus, *Carica Papaya*, Carob, Carolina Jasmine, Carom, Carony Bark, Carpenter's-herb, Carpenter's-square, Carpenter's Weed, Carrageen, Carrot, *Carthamus tinctorius, Carum Carvi*, Cascara, Cascara Buckthorn, Cascara Sagrada, Caseweed, Cashew Nut Shells, Cassava, *Cassia Senna, Castanea Sativa*, Castor Bean Plant, Castor Oil Plant, Catalonian Jasmine, Catchweed, *Catha, Catha edulis*, Catmint, Catnep, Catnip, Catrup, Cat's Claw, Cat's-foot, Cat's-play, Catswort, Cat Thyme, Catuaba, Caulophyllum *Thalictroides*, Cayenne, Ceanothus *Americanus*, Cedar Nut, Celandine, Celery, *Centaurea Cyanus, Centaurium* Erythraea, Centaury, Centella *Asiatica*, Century Plant, Cephaelis Ipecacuanha, Cerasee, *Ceratonia Siliqua*, Cereso, Cetraria *Islandica*, Chaga Mushroom, Chai Hu, Chamaelirium *Luteum*, Chamomile, *Chanca piedra*, Chandan, Chang Pu, Chaparral, Charapilla, Chaste Berry, Chaste Tree, Chat, Chaulmoogra, Checkerberry, Cheeseflower, Cheese Rennet, *Cheiranthus cheiri, Chelidonium majus, Chelone glabra, Chenopodium Ambrosioides*, Chen-Pi, Cherry Birch, Chervil, Chia, Chian, Chien, Chiang, Chickweed, Chicory, Chihma, Chi-hsueh-ts'ao, Chilean Wineberry, Chilgoza, Chili Pepper, *Chimaphila umbellata*, China Root, Chin-ch'iaomai, Chinese *Angelica*, Chinese Cabbage, Chinese Chives, Chinese Foxglove, Chinese *Ginseng*, Chinese Gold Thread, Chinese Lantern, Chinese Licorice, Chinese Mustard, Chinese Nettle, Chinese Star Anise, Chinese Wolfberry, Chink, *Chionanthus Virginicus*, Chirayata, Chiretta, Chittembark, Chives, Chocolate, Chocolate Root, Chocolate Vine, Choke Cherry, Chondrus *Crispus*, Christmas Tree, *Chrysanthemum, Chrysanthemum Balsamita, Chrysanthemum Cinerariifolium, Chrysanthemum Morifolium*, Chuan Xin Liang, Chuchupate, Church Steeples, Cicely, *Cichorium Intybus*, Cilantro, Cimicifuga, Cimicifuga *Racemosa*, Cinchona, Cinchona Bark, Cinchona spp, Cingulum Sancti Johannis, Cinnabar Root, *Cinnamomum camphora, Cinnamomum zeylanicum*, Cinnamon, Cinnamonwood, Cinquefoil, *Cirsium Vulgare*, Citroengrass, *Citrus aurantium, Citrus bergamia, Citrus ichangensis x Citrus reticulata* var. *austera, Citrus limon, Citrus reticulata, Citrus thyme*, City Avens, Clary, Clary Sage, Clear Eye, Cleavers, *Clematis* Stem, Clove, Clove Garlic, Clover, Clover Broom, Clove Root, Clown's Woundwort, Clubfoot Moss, Club Moss, *Cnicus benedictus*, Coca, Coca Shrub, Cocashweed, *Cochlearia officinalis*, Cocklebur, Cockle Buttons, Cocoa, *Codonopsis, Codonopsis pilosula, Coffea arabica*, Coffee, Coffeeweed, Coicis, Coix, Coix Lachryma-jobi, *Cola nitida, Colchicum, Colchicum autumnale, Coleus, Coleus forkolil, Coleus Forskohlii*, Colewort, Colicroot, Colla, *Collinsonia canadensis*, Colorado Cough Root, Coltsfoot, Colt's-tail, Comfrey, *Commiphora molmol, Commiphora mukul, Commiphora opobalsamum*, Common Alder, Common Alkanet, Common Anise, Common Amica, Common Ash, Common Balm, Common Barberry, Common Basil, Common Blue Violet, Common Broom, Common Buckthorn, Common Buckwheat, Common Bugle, Common Burnet, Common Caraway, Common Centaury, Common Chamomile, Common Club Moss, Common Cotton, Common Dock, Common Dill, Common Fennel, Common Fenugrec, Common Flax, Common Foxglove, Common Hazel, Common Holly, Common Hop, Common Horehound, Common Hyssop, Common Jasmine, Common Juniper, Common Lavender, Common Lime, Common Madder, Common Mallow, Common Marjoram, Common Nettle, Common Oats, Common Onion, Common Parsley, Common Periwinkle, Common Privet, Common Rue, Common Sage, Common Sagebrush, Common Sea-Buckthom, Common Stinging Nettle, Common Strawberry, Common Sundew, Common Thistle, Common Thyme, Common Wheat, Common White Jasmine, Common Willow, Common Wormwood, Compass Plant, Compass Weed, Compositae, *Conium Maculatum*, Consormol, Consumptive's Weed, *Convallaria majalis, Convolvulus sepium*, Cool Tankard, Copaiba, Copal, Copaifera Species, Coptidis, *Coptis, Coptis chinensis, Coptis* Rhizome, *Cordyceps,*

*Cordyceps sinensis*, Coriander, *Coriandrum sativum*, Corn, Cornelian Tree, Cornflower, Cornish Lovage, Corn Mint, Corn Poppy, Corn Rose, Cornsilk, *Cornus Florida*, Corsican Mint, Corsican Pepper, Corydalis, Corydalis Rhizome, Corydalis Yanhusuo, *Corylus avellana*, Costmary, Cotton, Cotton Thistle, Couch Grass, Coughroot, Coughweed, Coughwort, Countryman's-treacle, Cowbloom, Cow Chervil, Cow Clover, Cow Cress, Cowgrass, Cowplant, Cowslip, Crampbark, Crampweed, Cranberry, Cranberry Bush, Cranberry Tree, Cranesbill, *Crataegus* Monogyna, *Crataegus Oxyacantha*, Crataeva, Crataeva nurvula, Cream Of Tartar Tree, Creathnach, Creeping Charlie, Creeping Thyme, Creosote Bush, *Crocus sativus*, Crosswort, Croton Lechleri, Crowberry, Crow Corn, Cuban Oregano, Cubeb Pepper, Cuckoo's Cap, *Cucurbita Pepo*, Culantrillo, Culver's Physic, Culver's Root, Cumaru, Cumaruzeiro, Cumin, *Cuminum cyminum*, Curacao *Aloe*, Curare, *Curcuma longa, Curcuma zedoaria*, Cure-all, Curled Dock, Curled Mint, Curly Parsley, Curry-leaf tree, Curry Tree, Cuscus, Cuscuta Epithymum, Cusparia Bark, Custard Apple, Cutleaf Bugleweed, Cutweed, *Cydonia Oblonga, Cymbopogon Citratus, Cypripedium Pubescens*, Da Huang, Dalcini, Dalmatian Iris, Dalmation Insect Flower, Dalmation Pellitory, Dalmatian Sage, Damiana, Dandelion, Dang Gui, Danish Dill, Dan Shen, Daruharidra, Da suan, *Datura Stramonium, Daucus carota*, Deadly Nightshade, Deadmen's Bells, Dead Nettle, Dead-Rat Tree, Death-flower, Deerberry, Desert Cactus, Desert Oregano, Desert Tea, Devil's-apple, Devil's Bit, Devil's-bones, Devil's Cherries, Devil's Claw, Devil's Club, Devil's Dung, Devil's-eye, Devil's Guts, Devil's Herb, Devil's Plague, Dew of the Sea, Dhup, *Digitalis Purpurea*, Di Huang, Dill, Dillisk, Dillseed, Dillweed, Dilly, Dilsk, Dilo Oil Tree, *Dioscorea Villosa*, Diosma Betulina, Dipsacus *Sylvestris*, Dipteryx *Odorata*, Divale, Djamboe, Doda, Dodan, Doadni, Dodder, Dog Brier, Dog Grass, Dog Rose, Dog's Mercury, Dog Tree, Dogwood, Dong Chong Xia Cao, Dong Quai, Dovefoot, Drago, Dragon's Blood, Dragon's mugwort, Dragonwort, Dropsy Plant, Drosera *Rotundifolia*, Dryopteris filix-mas, Ducks Foot, Dulse, Dutch Clover, Dwale, Dwarf Juniper, Dwarf Nasturtium, Dwayberry, Dyeberry, Dyer's Broom, Dyer's Greenweed, Dyer's Madder, Dyer's-saffron, Dysphania *ambrosioides*, Early Winter Cress, Earth-smoke, Easter Flower, Easter Giant, Eau-de-cologne Mint, *Echinacea, Echinacea Angustifolia*, Egg Fruit, Egg Wrack, Egyptian Privet, Eight-homed Anise, Eight-horns, Ela, Elaci, Elder, Elder-berry, Elderflower, Elecampane, Eletteria Cardamomum, Eleuthero, Eleutherococcus Senticosus, Elk Mint, Emetic Herb, Enandi, Endive, English Alder, English Balm, English Catnip, English Chamomile, English Hawthorn, English Holly, English Hop, English Mandrake, English Serpentary, English Thyme, English Valerian, English Violet, English Wallflower, Epazote, Ephedra, Ephedra *Nevadensis*, Ephedra *Sinica*, Epifagus *virginiana*, Epilobium *Angustifolium*, Epimedium, Epimedium *grandiflorum*, Equisetum *Arvense*, Erigeron *canadensis*, Eriodictyon Califomicum, *Eruca vesicaria sativa*, Erythraea *Centaurium*, Erythroxylum Catuaba, Erythroxylum Coca, *Eschscholzia Califórnica*, Espinheira Santa, Estragon, Ethiopian Cumin, *Eucalyptus, Eucalyptus Globulus*, Eugenia Carophyllata, Eupatorium, Eupatorium *Perfoliatum*, Eupatorium *Purpureum, Euphorbia Hirta*, Euphrasia *Officinalis*, European Alder, European *Angelica*, European Ash, European Barberry, European Black Alder, European Buckthom, European Centaury, European Chestnut, European Cowslip, European Dill, European Elder, European Holly, European Hop, European White Water lily, European Willow, *Euterpe Oleracea*, Evening Primrose, Evening Star, Evergreen, Eye Balm, Eyebright, Eyeroot, *Fagopyrum Esculentum, Fagus* Grandifalia, Fah Tolai, Fairy Cup, Fairy's Glove, False *Acacia*, False Box, False Chamomile, False Jasmine, False Saffron, False Unicorn, False Valerian, False White Cedar, Featherfew, Featherfoil, Feather Geranium, Febrifuge Plant, Felon Herb, Felonwort, Female Fern, Fennel, Fenugreek, Ferula Asafoetida, Fetid Horehound, Fever Bush, Feverfew, Fever Grass, Fever Tree, Feverwort, Fiber, *Ficus* religiosa, Field Balm, Field Pansy, Field Poppy, Field Pumpkin, Field Sorrel, Figwort, Filipendula Ulmaria, Fir, Fir Balsam, Fireweed, Fir Pine, Fishfuddle, Five-fingers, Five-leaf, Flag Lily, Flagroot, Flanders Poppy, Flannelleaf, Flat-leaved Parsley, Flax, Flax Seed, Flax Weed, Fleabane, Flea Seed, Flesh and Blood, Fleur-de-lis, Flinders Rose, Florentine Iris, Florida Dogwood, Florida Fishpoison Tree, Flower de-luce, Flowering Dogwood, Flowering Willow, Flowery Knotweed, *Foeniculum Vulgare*, Folk's Glove, Food Of The Gods, Forsythia, Forsythia suspensa, Fo Ti, Foxberry, Fox Geranium, Foxglove, Fox Grape, Foxtail, Fragaria *ananassa*, Fragaria *Vesca*, Fragrant Balm, Fragrant Giant Hyssop, Fragrant Sumac, Frankincense, *Fraxinus Americana, Fraxinus Excelsior*, French Basil, French Lilac, French Parsley, French Rose, French Sorrel, French Tarragon, French Thyme, Friar's Cap, Fringe Tree, *Fritillaria, Fritillaria Thunbergii*, Frog Plant, Fucus Vesiculosus, Fu-ling, Fuller's-herb, *Fumaria officinalis*, Fumitory, Gagroot, Galangal, *Galega officinalis, Galipea officinalis, Galium Aparine, Galium Odoratum, Galium verum*, Gambooge, Gan cao, Gandana, Ganja, Gan-jiang, *Ganoderma Lucidum*, Gao Liang, Garabato, Garcinia, Garcinia cambogia, Garcinia gummi-gutta, Garcinia Kola, Garden Angelica, Garden Balm, Garden Basil, Garden Burnet, Garden Chamomile, Garden Chervil, Garden Chicory, Garden Dill, Garden Heliotrope, Garden Hyssop, Garden Lavender, Garden Loosestrife, Garden Marigold, Garden Mint, Garden Myrrh, Garden or Green Purslane, Garden Patience, Garden Rosemary, Garden Rue, Garden Sage, Garden Thyme, Garden Violet, Garlic, Garlic Chives, Garlic Sage, *Gaultheria Procumbens*, Ge-gen, *Gelsemium Sempervirens, Genista, Genista Tinctoria, Gentian, Gentiana Lutea*, Geranium *Maculatum*, Geranium *Robertianum*, Geraniums, German Chamomile, Germander, German Mustard, German Rue, German Tarragon, German Thyme, German Valerian, *Geum urbanum*, Ghaap, Gill Run Over, Ginger, *Ginkgo, Ginkgo biloba, Ginkgo* Nut, Ginny Grains, Ginny Papper, Ginseng, *Glechoma Hederacea*, Glossy Buckthom, *Glycine max, Glycyrrhiza Glabra*, Goathead, Goat's Rue, Goatweed, Goat Wort, Gold Coin Grass, Golden Aspen, Goldenberry, Golden Flower of Mary, Golden Loosestrife, Golden Ragwort, Golden Root, Goldenrod, Goldenseal, Golden *Senecio*, Gold *Melissa*, Goldy Star, Goosefoot, Goose Grass, Goosewort, Gorikapuli, Gospel Tree, *Gossypium Hirsutum*, Gotu Kola, Gourmet Parsley, Goutweed, Gow Choy, Graines, Grains Of Paradise, Gramineus, Grape, Grape Vine, Grass, Grass Burdock, Gravelroot, Graviola, Graybeard, Greasewood, Great Burdock, Greater Burnet, Greater Cardamom, Great Morel, Great Nettle, Great Stinging Nettle, Great Wild Valerian, Greek Hayseed, Green Ginger, Green Ozier, Green Tea, *Grifola frondosa*, Grindelia, Grindelia Camporum, Groats, Ground Berry, Ground Cherry, Ground Holly, Ground Ivy, Ground Juniper, Ground Lemon, Ground Lily, Groundnut, Ground Pine, Ground Raspberry, Grouse Berry, Guaiac, *Guaiacum*, Guajacum, *Guaiacum officinale, Gualtheria procumbens*, Guarana, Guasai, Guava Tree, Guelder Rose, Guggul, Gui, Guinea Grains, Guinea Pepper, Guinea Seeds, Gum Bush, Gum Guggulu, Gum Myrrh Tree, Gumplant, Gurmabooti, Gurmar, *Gymnema, Gymnema syl-*

*vestre*, Gynostemma, Gynostemma pentaphyllum, Gypsyweed, Gypsywort, Habanero Pepper, Hackmatack, Hai-ts'ao, *Hamamelis Virginiana*, Handflower, Happy Tree, Hapusha, Hardock, Hareburr, Hare's Ear Root, *Harpagophytum procumbens*, Hartshorn Plant, Harvest Lice, Hasabis, Hashish, Hatomugi, Haw, Hawaii Nut, Hawkweed, Hawthorn, Haymaids, Hazelnut Tree, Heal-All, Heart Of The Earth, Heartsease, Heather, Hebanthe *Paniculata*, Hedge Bind Weed, Hedge Fumitory, Hedge Maid, Hediondilla, *Helianthus Annuus*, Heliotrope, Hellweed, Helmet Flower, Helonias Root, Hemlock, Hemp, Henbane, Henna, Herb Bennet, Herb-of-Grace, Herb of St. Barbara, Herb of The Angels, Herb-of-the-cross, Herb Robert, Hercules Woundwort, He Shou Wu, *Hibiscus, Hibiscus Sabdariffa, Hieracium* Pilosella, Hierochloe *odorata*, High *Angelica*, High Mallow, Hill Berry, Hina, Hind Heal, Hineheel, Hing, Hini, Hippophae rhamnoides, Hip Rose, Hoarhound, Hockheal, Hodoimo, Hoelen, Hog Apple, Hog Bean, Hog Cranberry, Hogweed, Holigold, Holly, Holy Basil, Holy Ghost Plant, Holy Herb, Holy Grass, Holy Thistle, Honey Plant, Honeysuckle, Hoodia, Hoodia *pilifera*, Hood Weed, Hoodwort, Hook-heal, Hopniss, Hops, Hops Vine, Horehound, Horny Goatweed, Horse Balm, Horse Chestnut, Horsefly Weed, Horseheal, Horse Mint, Horseradish, Horse Savin, Horsetail, Horse Thistle, Horseweed, Ho She Wu, Ho Shou Wu, Hot Mint, Hsia-ku-ts'ao, Hsiao-hui-hsiang, Hsieh-tzu-ts'ao, Hua-Hsian, Huang Qi, Huang Quin, Huarango, Hu-chin-ts'ao, Huckleberry, Hu-lu-ba, Hu-lu-pa, *Humulus Lupulus*, Hungarian Chamomile, Huo Ma Ren, Hurrburr, Hurtleberry, Hurtsickle, Husk Cherry, Hydnocarpus, Hydnocarpus *kurzii, Hydrangea, Hydrangea Arborescens*, Hydrastis *Canadensis, Hyoscyamus Niger, Hypericum, Hypericum* Perforatum, Hyssop, *Hyssopus Officinalis*, Iceland Lichen, Iceland Moss, I-chi-kao, Ignatia *Amara*, Ignatius Bean, Ilang-Ilang, *Ilex Aquifolium, Ilex Paraguariensis*, Illicium *verum*, Ill-scented Sumac, Imburana De Cheiro, Incensier, Indian Apple, Indian Arrowroot, Indian Balm, Indian Balmony, Indian Bedellium, Indian Borage, Indian Bread, Indian Chickweed, Indian Corn, Indian Dye, Indian Elm, Indian Gentian, Indian *Ginseng*, Indian Gooseberry, Indian Lotus, Indian Mustard, Indian Nettle, Indian Nut, Indian Olibanum, Indian Paint, Indian Pennywort, Indian Pink, Indian Plant, Indian Plume, Indian Potato, Indian Red Paint, Indian Root, Indian Sage, Indian Shamrock, Indian Snakeroot, Indian Tobacco, Indian Tree, Indigo Broom, Inonotus obliquus, Inula Helenium, Ipecac, Ipecac Shrub, Ipio, Iporoni, Iporuru, *Iris, Iris Florentina, Iris Germanica*, Irish Broom, *Iris pallida*, Irish Moss, *Iris Versicolor*, Italian Burnet, Italian Cress, Italian Jasmine, Italian Lovage, Italian Pimpernel, Ivory Plum, Jaborandi, Jackfruit, Jack Tree, Jak, Jacob's Chariot, Jacob's-staff, Jacón, Jamaican Dogwood, Jamaica Pepper, Jamaica Sorrel, Jambu, Jambul, Jamestown Weed, Japanese Catnip, Japanese Grapefruit, Japanese Horseradish, Japanese Mint, Japanese Mushroom, Japanese Seaweed, Jasmin, Jasmine, Jasmini Flos, *Jasminum* spp., Jateorhiza *Palmata*, Jaundice Berry, Jaundice Root, Java Pepper, Java Plum, Jersey Tea, Jerusalem Oak, Jessamine, Jesuit's Balsam, Jesuit Tea, Jew's-harp Plant, Jiaogulan, Jicara, Jimsonweed, Jing Jie, Jin Qian Cao, Jin Yin Hua, Job's Tears, Joe Pye Weed, *Juglans cinerea, Juglans Nigra, Juglans Regia*, Johnny-jump-up, Johnswort, Joint Fir, Ju Hua, Juniper, Juniper Bark, Juniper Berry, Juniper Bush, Jupiter's Bean, *Juniperus Communis*, Kachur, Kalmegh, Kamoteng Kahoy, Kanma, Kan-ts'ao, Kappa, Katphala, Kava Kava, Kelp, Kelpware, Kemangen, Keyflower, Key of Heaven, Khas Khas, Khat, Khella, Kiawe, Kidney Stone Tree, King Of Bitters, King's-clover, King's Crown, King's Cure, King's-cure-all, Kinnikinnick, Kiryat, Klamath Weed, Knitback, Knitbone, Knotgrass, Knotted Kelp, Knotted Marjoram, Knotted Wrack, Knotty Brake, Knotweed, Kola Nut, Korean *Ginseng*, Kua-lou, Kuawa, Kudzu, Kuei, Kumari, Kumaru, Kuo-lao, K'u-tou, Ku Ts'ai, Lactucarium, *Lactuca Virosa*, Ladder-to-heaven, Ladies'-delight, Ladies' Seal, Lady Bleeding, Lady's Bedstraw, Lady's Slipper, Lady's Mantle, Lady's-washbowl, Lai-ei-ts'ao, Lamb Mint, *Lamium Album*, Lammint, Lang-tu, Langue de Boeuf, Lapacho, *Lappa, Lappa* Minor, Large Fennel, Large-leaved Germander, Larrea *Tridentata*, Latherwort, *Laurus Nobilis*, Lavender, Lavender Giant Hyssop, *Lavandula officinalis*, Lawn Chamomile, Lawsonia *inermis*, Leafcup, Lebanese Oregano, Leeks, Lemon, Lemon Balm, Lemon Thyme, Lemon *Verbena*, Lemongrass, Lentinus *Edodes, Leonurus Cardiaca*, Leopard's Bane, *Lepidium meyenii*, Leptandra, Leptandra *Virginica, Leptospermum scoparium*, Lesser Indian Cress, Lesser Periwinkle, Le-ts'ao, Lettuce Opium, *Levisticum Officinale*, Lian Qiao, Licorice, Licorice Mint, Licorice Root, Life Root, Lignum Vitae, *Ligusticum Porteri, Ligustrum Vulgare*, Lily Convalle, Lily of the Valley, Limaosinho, Limeblossom, Lime Flowers, Lime Mint, Lime Tree, Linden, Linden Flower, *Lindera benzoin*, Ling Chi, Ling-t'ung, Ling Zhi, Link, Linseed, Lint Bells, *Linum Usitatissimum*, Lion's Ear, Lion's Foot, Lion's Tail, Lion's Tart, Lion's Tooth, Lippia *graveolens*, Lipstick Tree, Liquorice, Live-Forever, Live-Long, Liver Lily, Liverwort, Lizard's Tail, *Lobelia, Lobelia Inflata*, Longevity Herb, *Lonicera* Caprifolium, *Lonicera Japonica, Lonicera* Spp, Loodroot, Loosestrife, Lophophora williamsii, Lotus, Lotus Comiculatus, Lousewort, Lovage, Love Apples, Love in Winter, Love-lies-bleeding, Love Persley, Love Vine, Luceme, Lu Hui, Lungwort, Luole, Lychee, Litchi *chinensis, Lycium, Lycium Chinense, Lycium* Fruit, Lycopodium, Lycopodium *clavatum, Lycopus americanus, Lysimachia christinae, Lysimachia vulgaris, Lythrum salicaria*, Ma Bian Cao, Macadamia Nut, Macadamia spp., Maca, Maca-Maca, Mace, Macochihua, Madagascar Periwinkle, Mad Apple, Madder, Madder Root, Madderwort, Mad Dog, Madweed, Madrone Tree, Ma huang, Maidenhair Fern, Maidenhair Tree, Maid's-hair, Maino, Maitake, Maize, Maka, Malabar Cardamom, Malabar Plum, Malabar Tamarind, Mal-dos-sete-dias, Male Fern, Mallow, Malpighia species, *Malus Communis*, Malva *Sylvestris*, Mamey Sapote, Manac, Mandioc, Mandragora, Mandragora *Officinarum*, Mandrake, Mangosteen Oil Tree, *Manihot esculenta*, Manioc, Manioc Root, Manna Grass, Man-t'ien-hsing, Manuka, Manuka Myrtle, Manuka Tree, Manzanilla, Maqui, Maramar, Maranta Arundinaceae, Maranta Starch, Marapuama, Mare's Tail, Marigold, Maroochi Nut, *Marrubium, Marrubium Vulgare*, Marshmallow, Marsh Marigold, Marsh Parsley, Marsh Trefoil, Marsh Woundwort, *Marum*, Marvel, Mary Bud, Mary Golde, Mary Gowles, Mary Jane, Maryland Pink, Mary's Grass, Mary's Mantle, Mary's Thistle, Master of the Woods, Masterwort, Mastic, Mate, *Matricaria Chamomilla*, May, Mayapple, May Blossom, Maybush, May Lily, Maypop, *Maytenus, Maytenus* Species, May Tree, Meadow Clover, Meadow Eyebright, Meadow Saffron, Meadow Sage, Meadowsweet, Mealberry, *Medicago Sativa*, Mei-ts'ao, *Melaleuca, Melaleuca* Altemifolia, Melegueta Pepper, Melilot, Melilotus *Officinalis, Melissa, Melissa Officinalis*, Melmot Berry, *Mentha haplocalyx, Mentha piperita, Mentha pulegium, Mentha requienii, Mentha suaveolens, Mentha spicata*, Menthol Mint, *Mentha x piperita citrata, Menyanthes Trifoliata, Mercurialis Perennis*, Mescal, Meshasringi, Mesquite, Methi, Mexican Mint, Mexican Oregano, Mexican Poppy, Mexican Potato, Mexican Tea, Mexican Thyme, Mexican Wild Yam, Mexico Seed, Middle Comfrey, Mignonette Tree, Mi-kan, Milfoil, Milk Ipecac, Milk Thistle, Milkwort, Millefoil, Mint, Mints, Miracle Herb, Miracle Tea, Mistletoe, *Mitchella Repens*, Mi-tieh-hsiang, Mi-ts'ao, Moccasin Flower, Mogo, Molina, Mo Li Hua, *Momordica Charantia*, Monarda Didyma, Monkey-Bread Tree, Monkshood, Monk's Pepper, Moonflower, Moon Grass, Moose Elm, *Morinda, Morinda citrifolia, Morinda officinalis*, Mormon Tea, Moroccan Ironwood, Mortification Root, *Morus Nigra*, Mother-of-thyme, Mother's-heart, Motherwort, Moujean Tea, Mountain Amica, Mountain Ash, Mountain Aspen, Mountain Balm, Mountain Berry, Mountain Box, Mountain Cranberry, Mountain Daisy, Mountain Grape, Mountain Holly, Mountain Mint, Mountain Savory, Mountain Strawberry, Mountain Tobacco, Mountain Tea, Mouse-ear, Mugwort, Muira Puama, Mujonso, Mulberry, Mullein, Murraya koenigii, Muscatel Sage, Mu-Su, Mu Tong, Mu-yao, Myrciaria *dubia, Myrica, Myrica* Cerifera, Myricae Cortex, *Myristica Fragrans*, Myroxylon Balsamum, Myroxylon *Pereirae*, Myrrh, Myrrhis *odorata*, Myrtle, Myrtle Pepper, *Myrtus communis*, Nagara, Naidi, Naked Ladies, Napa Cabbage, Nappa, Narrow Dock, Narthex, Nashia *inaguensis*, Nasturtium *Officinale*, Naughty Man's Cherries, Neem, *Nelumbo nucifera*, Nenuphar, Nep, *Nepeta Cataria*, Nerveroot, Nettle, Nettle Flowers, New England Pine, New Jersey Tea, New Zealand Tea Tree, Niando, *Nicotiana Rustica*, Nightshade, Night Willow Herb, Nine Hooks, Nine Joints, Nip, Nira, Niu Bang, Noble Chamomile, Noble Yarrow, Nodding Wakerobin, Noni, Normandy Cress, Northern Pine, Northern Spicebush, Northern White Cedar, Norwegian Kelp, Nosebleed, Nutmeg, Nux Vomica, *Nymphaea Alba*, Oak, Oats, *Ocimum basilicum, Ocimum tenuiflorum, Oenothera Biennis*, Ohio Curcuma, Oil plant, Oilnut, Oil Nut Tree, Old English Lovage, Old-maid's-nightcap, Old-maid's-pink, Old Man, Old-man's-beard, Old Man's Nightcap, Old Man's Pepper, Old woman, *Olea Europaea*, Olibanum, Olive, Omam, Omum, One-berry, Onion, Opium Poppy, Oplopanax *horridus*, Orange, Orange Mint, Orange Root, Ordeal Bean, Oregano, Oregano Brujo, Oregon Grape, Oriental Garlic, Oriental Mustard, Oriental Poppy, *Origanum majorana, Origanum syriacum, Origanum vulgare*, Orpine, Orris Root, Osha, Osterick, Oswego Tea, Our-Lady's-bedstraw, Our-Lady's-tears, Oval Buchu, Owler, Oxadoddy, Ox Balm, Ox Heart, Ox-tongue, Pacific Madrone, Pacific Yew, Padmaka, *Paeonia Officinalis*, Paico, Paigle, Palisade Pine, Palma Christi, Palmaria *Palmata*, Palmetto, *Panax Ginseng, Panax* Quinquefolium, Panay, Pansy, *Papaver orientale, Papaver Rhoeas, Papaver Somniferum, Papaya*, Paper Birch, Papoose Root, Paracress, Paraguay Tea, Pareira, Parell, *Parietaria Officinalis*, Pariswort, Parsley, Parsnip, Partridgeberry, Pasque Flower, *Passiflora, Passiflora* Incamata, Passion Flower, Passions, Passion Vine, *Pastinaca sativa*, Patchouli, Patience Dock, Patience Herb, Pau d'Arco, Paullinia Cupana, Pausinystalia Yohimbe, Pauson, Peepal Tree, Pei-ma, Peking Cabbage, *Pelargonium, Pelargonium* sidoides, *Pelargonium* species, Pellitory, Pellitory Of The Wall, Pembina, Pennyroyal, Peony, Pepperidge Bush, Peppermint, Pepperweed, Perfume Tree, Periploca Of The Woods, *Persea Americana*, Persian Berries, *Persicaria odorata, Personata*, Peruvian Balsam, Peruvian Bark, Peruvian *Ginseng*, Peruvian Ground Cherry, Petasites *Hybridus*, Petokal, Petroselinum Crispum, Peumus Boldus, Peyote, Pfaffia *paniculata*, Philanthropos, Phudina, Phyllanthus, Phyllanthus emblica, Phyllanthus niruri, Physalis Alkekengi, Physalis *Peruviana* L., Physic Root, *Physostigma venenosum, Phytolacca Americana*, Picrasma *Excelsa*, Pigeon's Grass, Pignoli, Pigweed, Pikake, Pill-Bearing Spurge, Pilocarpus Microphyllus, Pilosella, Pimbina, Pimenta *Dioica*, Pimenta *Officinalis*, Pimpinella Anisum, Pine, Pine Nut, Pineapple, Pineapple Strawberry, Pineapple *Verbena*, Pinkroot, Pink Rose, Pinon Nut, *Pinus* spp., *Pinus Strobus, Pinus Sylvestris*, Pinyon Pinenut, *Piper betle, Piper cubeba, Piper Methysticum, Piper Nigrum*, Pipe Tree, Pipsissewa, Pistachio, *Pistacia vera*, Piscidia piscipula, Pissabed, Pistachio, *Plantago Major, Plantago Psyllium, Plantago* Seed, Plantain, Plectranthus *amboinicus*, Pleurisy Root, Plum Rose, *Podophyllum Peltatum*, Poet's Jasmine, Pogostemon cablin, Poha Berry, Poison Ash, Poison Flag, Poison Parsley, Poison Tobacco, Pokeroot, Pokeweed, Polar Plant, Polygala Senega, *Polygonatum Multiflorum, Polygonum* Aviculare, *Polygonum* Bistorta, *Polygonum Multiflorum, Polygonum odoratum*, Polypodium *Vulgare*, Polypody, Poor Man's *Ginseng*, Poor-man's-treacle, Poplar, Popotillo, *Populus alba, Populus Tremuloides*, Poria, Poria *cocos, Portulaca Oleracea*, Pot, Potato Bean, Potency Wood, Potentilla *Anserina*, Potentilla *Erecta*, Potentilla *Reptans*, Potenzholz, Pot Marigold, Pouteria sapota, Pouteria campechiana, Prairie Smoke, Prickly Ash, Prickly Lettuce, Prickly Pear Cactus, Prickly Poppy, Priest's-crown, Prim, Primrose, *Primula* Veris, Prince's Feather, Prince's-pine, Privet, *Prosopis pallida* syn. *Prosopis limensis*, Provence Rose, Prunella, Prunella Vulgaris, *Prunus* Amygdalus, *Prunus Dulcis, Prunus Serotina, Prunus Spinosa, Psidium Guajava*, Psoralea, Psoralea corylifolia, Psoralea Fruit, *Psyllium*, Ptychopetalum *ovata, Pueraria Lobata*, Puff Ball, Pu gong ying, Pukeweed, Pu-kung-ying, Pulmonaria *Officinalis, Pulsatilla*, Pumpkin, Pumpkin Pine, Puncture Vine, Purging Buckthorn, Purple *Angelica*, Purple Betony, Purple Clover, Purple Coneflower, Purple Foxglove, Purple Leptandra, Purple Loosestrife, Purple Medic, Purple Passionflower, Purple Rocket, Purplestem *Angelica*, Purslane, Pygeum, Pygeum *Africanum*, Pyrethrum, Pyrola *Umbellata*, Quack Grass, Quaking Aspen, Quassia, Quassia Bark, Quassia Wood, Quebra Pedra, Queen Annes Lace, Queen Of The Meadow, Queensland Nut, Queen's Delight, Queen's-root, *Quercus alba*, Queue de Lezard, Quickbeam, Quick-set, Quince, Quinine Tree, Quinsy Berries, Quiverleaf, Race Ginger, Racoon Berry, Rainbowweed, Rashona, Raspberry, Raspberry Leaf, Rat's Tail, Rattlebush, Rattleroot, Rattlesnake Root, Rattleweed, Rau Ram, Rauwolfia, Rauwolfia *Serpentina*, Red Alder, Red Balm, Red Bearberry, Red-bearded, Red Bergamot, Redberry Tea, Red Bush Tea, Red Clover, Redcole, Red Dulse, Red Eyebright, Red Legs, Red Paint Root, Red Pollom, Red Poppy, Red Puccoon, Red Raspberry, Red Robin, Red Root, Red Root Sage, Red Rose, Red Sage, Red Sorrel, Red Sunflower, Red Tea, Red *Trillium*, Red-veined Dock, Reefer, Rehmannia, Rehmannia *Glutinosa*, Reishi, *Rhamnus Cathartica, Rhamnus* Frangula, *Rhamnus Purshiana*, Rheumatism Root, Rheumatism Weed, Rheum *Palmatum, Rhodiola, Rhodiola* sacra, Rhubarb, *Rhus trilobata, Ribes Nigrum*, Ribwort, Richweed, *Ricinus Communis*, Rimed *scutatus*, Ritha, *Robinia Pseudoacacia*, Rock Brake, Rock Fern, Rockweed, Roman Chamomile, Roman Cumin, Roman Fennel, Rooibos, Root Of The Holy Ghost, Roquette, *Rosa Canina, Rosa Centifolia, Rosa Gallica*, Rose, Rose Apple, Roselle, Rosemary, Rosemary Plant, Rose-noble, Rose Root, Rosin Rose, *Rosmarinus Officinalis*, Rosy Periwinkle, Rou Dou Kou, Round Buchu, Round-leaved Dock, Round-leafed Mint, Round-leaved Sorrel, Rowan Tree, Royal Herb, Royal Jasmine, Rub Cherry, *Rubia tinctoria, Rubus* Fructicosus, *Rubus Idaeus*, Rucola, Rue, Rugula, Rumara, *Rumex Acetosella, Rumex Crispus, Rumex Hymenosepalus, Rumex Obtusifolius*, Running Club Moss, Ruscus *Aculeatus*, Russian Chamomile, Russian Mustard, Rustic's Treacle, *Ruta Graveolens, Sabal, Saccharum officinarum*, Sacred Bark, Sacred Basil, Sacred Fig, Sacred Lotus, Sacred Plant, Sacred Sage, Sacred Tree, Sacred Water Lotus, Safflower, Saffron, Sagackhomi, Sage, Sage-leaved Germander, Sage Of Bethlehem, Sake, Salad Burnet, Salad Chervil, Salad Rocket, Salai Gugal, *Salix Alba*, Saloip, *Salvia, Salvia apiana, Salvia hispanica, Salvia* Miltiorrhiza, *Salvia Officinalis, Salvia Sclarea, Sambucus Nigra*, Sampson Root, Sandalwood, Sandberry, Sangre de Drago, Sangue de Drago, *Sanguinaria, Sanguinaria Canadensis*, Sanguisorba Minor, Sanguisorba *Officinalis*, Sanicle, Sanicula *Europaea*, Sanicula *Marilandica, Santalum* Album, Sapin, Sapindus mukorossi, *Saponaria Officinalis*, Sapote, Sarapia, Sarepta Mustard, Sarothamnus *Scoparius*, Sarpagandha, Sarsaparilla, *Sassafras, Sassafras Albidum*, Satan's Apple, Satavar, Satinflower, *Satureja hortensis, Satureja montana*, Saventaro, Savory, Saw Palmetto, Saxifrax, Scabish, Scabwort, Scarlet Bergamot, Scarlet Monarda, Scarlet Sage, Scarweed, Scented Fern, Scented Sumac, Schisandra, Schisandra *Chinensis*, Schizonepeta, Schizonepeta *tenuifolia*, Scopolia, Scopolia camiolica, Scotch Broom, Scotch Fir, Scotch Heather, Scotch Pine, Scots Pine, Scouring Rush, Scrofula Plant, Scrophularia *Nodosa*, Scurfy Pea, Scurvy Grass, Scurvy Weed, Scutellaria *Baicalensis*, Scutellaria Lateriflora, Sea Buckthom, Sea Lettuce Flakes, Sea Oak, Sea Onion, Sea Parsley, Seaweed, Seawrack, Sedum Telephium, Self-Heal, Seneca Snakeroot, *Senecio Aureus*, Seneca Grass, Senega, Senega Root, *Senna*, Sereh, Serenoa *Repens, Serpentary, Serpyllum*, Setwall, Shameface, Shancha, Sha-ren, Shan-yao, Shatamull, Shatapushpa, Shatavari, Shave Grass, Shea Tree, Sheepberry, Sheep Sorrel, Sheng Di, Sheng Di Huang, Sheng Ti Huang, Shen-jiang, Shepherd's Knot, Shepherd's Needle, Shepherd's Purse, Shi Chang Pu, Shield Fern, Shih-lo, Shihuahuaco, Shiitake, Shiny *Asparagus*, Shirokikurage, Shoofly, Short Buchu, Short-leaved Buchu, Shovelweed, Shu Di Huang, Shu Ti Huang, Siberian *Ginseng*, Sicklewort, Silkweed, Silver Birch, Silver Fir, Silver Leaf, Silver-leaf Poplar, Silver Mint, Silver Pine, Silver Poplar, Silver Tree-ear Fungus, Silverweed, *Silybum*, Silymarin, Simply Jack, *Sinapis alba*, Skullcap, Skunkbush, Skunkbush Sumac, Skunk Cabbage, Slippery Elm, Sloe, Smallage, Smallanthus sonchifolius, Small Nasturtium, Smelling-stick, *Smilax* Uti Lis, Smooth Cicely, Smooth Strophanthus, Snakebite, Snake Lily, Snake Root, Snakeweed, Snapping Hazelnut, Snap-Wood, Snowball Tree, Snowdrop Tree, Snowflake, Snowflower, Snow Fungus, Soap Berry, Soapnut, Soapwort, Soft Pine, *Solanum Dulcamara*, Soldier's Cap, Soldier's Woundwort, Solidago *Canadensis*, Solidago Virgaurea, Solis Sponsa, Solomon's Seal, Solsequia, Son-before-the-father, *Sorbus Aucuparia*, Sour Dock, Sour Grass, Soursop, Sour Weed, Southern *Ginseng*, Southemwood, Sowberry, Soy, Soya, Soybean, Spanish Chamomile, Spanish Chestnut, Spanish Jasmine, Spanish Thyme, Spearmint, Speedwell, Spiceberry, Spicebush, Spicewood, Spicy Wintergreen, Spigelia *Marilandica*, Spike Lavender, Spiked Loosestrife, Spikenard, Spilanthes *acmella*, Spoonwood, Spoonwort, Spotted Alder, Spotted Thistle, Spring Cress, Spring Wintergreen, Square Stalk, Squawbush, Squaw Root, Squaw Tea, Squaw Vine, Squill, Stachys *Officinalis*, Stachys *Palustris*, Stagbush, Staghom, Stanchgrass, Star Anise, Starbloom, Star Flower, Star Fruit, Star Grass, Starweed, Starwort, *Stellaria, Stellaria Media*, Stickwort, St. Ignatius Bean, Stillingia *Sylvatica*, Stingnose, Stinking Benjamin, Stinking Christopher, Stinging Nettle, Stingless Nettle, Stinking Nightshade, Stinking Roger, Stinking Rose, Stinking Weed, Stinking Willie, Stinkweed, Stitchwort, St. John's Bread, St. John's Grass, St. John's Plant, St. John's Wort, St. Josephwort, Stonecrop, Stone Root, Strawberry, Stork's Bill, Strawberry Tomato, Strawberry Tree, Striped Alder, Strophanthus, Strophanthus Gratus, Strychnine, Strychnine Tree, Strychnos nux-vomica, *Styrax Benzoin*, Succory, Sudanese Tea, Sugar Cane, *Sui Hoi*, Suma, Su Nanesi, Sundew, Sunflower, Sunkfield, Sunthi, Surasa, Suterberry, Swallowwort, Swamp Cedar, Swamp Root, Sweating Plant, Sweet Almond, Sweet Balm, Sweet Basil, Sweet Bay, Sweet Birch, Sweet Bracken, Sweet Brake, Sweet Bugle, Sweet Cane, Sweet Chervil, Sweet Chestnut, Sweet Cicely, Sweet Clover, Sweet Coltsfoot, Sweet Cumin, Sweet Dock, Sweet Elm, Sweet Fennel, Sweet Fern, Sweet Flag, Sweet Flag Rhizome, Sweet Goldenrod, Sweet Grass, Sweet Iris, Sweet Lavender, Sweet Licorice, Sweet Luceme, Sweet Marjoram, Sweet Myrrh, Sweet Root, Sweet Rush, Sweet-scented Geranium, Sweet Tea Vine, Sweet Tongue, Sweet Violet, Sweetweed, Sweet Wood, Sweet Woodruff, Swertia, Swertia chirayita, Swine Snout, Symphytum *Officinale*, Symplocarpus *Foetidus*, Syrian Oregano, Syzygium cumini, Syzygium jambos, *Tabebuia* Spp., Tagara, Taheebo, Ta-huang, Tailed Cubebs, Tailed Pepper, Tailwort, Tall Nasturtium, Tallow Shrub, Tall Speedwell, Tall *Veronica*, Tamanu Nut Tree, Tamarind, Tamarindus Indica, Tamus, *Tanacetum Parthenium, Tanacetum Vulgare*, Tang Kuei, Tanners Bark, Tanner's-dock, Tan Shen, Tansy, Tap *Aloe*, Tapioca-root, *Taraxacum Officinale*, Tarragon, Tartar Root, Tarweed, *Taxus Brevifolia*, Teaberry, Teasel, Tea Tree, Te *Limon, Telltime, Tenuifolia*, Terminalia Arjuna, Tetterberry, Tetterwort, *Teucrium marum, Teucrium scorodonia*, Thali, *Theobroma Cacao*, Thom Apple, Thorn Poppy, Thomtree, Thorny Burr, Thoroughwort, Thousandleaf, Thousand-seal, Three-leaved Caper, Three-leaved Nightshade, Throatwort, *Thuja, Thuja Occidentalis*, Thumb, Thunberg *Fritillaria* Bulb, Thyme, *Thymus citriodorus, Thymus Serpyllum, Thymus Vulgaris*, Tian Men Dong, Tibetan *Rhodiola*, T'ien-shih-li, Ti Huang, Ti Huang Chiu, *Tilia Americana, Tilia Cordata, Tilia* Europea, Tipton Weed, Toad Flax, Tobacco Wood, Tokal, Tomillo, Tom Thumb Nasturtium, Tongue Grass, Tonka, Tonka Bean, Tonka Bean Tree, Tonquin Bean, Toothache Plant, Toothache Tree, Trachyspermum ammi, Treacle Mustard, Tree Moss, Tree of Joy, Tree of Life, Tree's Dandruff, Trefoil, Trembling Aspen, Trembling Poplar, Tremella fuciformis, Tribulus, Tribulus *terrestris*, Tricolor Garlic, *Trifolium pratense, Trifolium repens, Trigonella, Trigonella* Foenum-Graecum, *Trillium, Trillium Erectum, Triticum aestivum, Tropaeolum minus*, Tormentil, True Angostura, True Chamomile, True Lavender, True Oregano, True Sage, True Taragon, True Unicorn Root, Tse-lan, Tuber Root, Tuckahoe, Tulasi, Tulsi, Tumeric Root, Tuna Cactus, Turkey Burrseed, Turkish Oregano, Turmeric, Turnera *Diffusa*, Turtlebloom, Turtlehead, Tussilago Farfara, Twak, Twinflower, Tzu-mo-lo, Uassi, *Ulmus Rubra*, Uma, Umbrella Plant, Umcka, Umckaloabo, Una De Gato, Uncaria *Tomentosa*, Undaria *pinnatifida*, Upland Cotton, Upland Cress, Upland Cranberry, Uppagi, Upside-Down Tree, Urginea *Maritima, Urtica Dioica*, Usnea, Usnea spp., Uva *Ursi, Vaccinium Macrocarpon, Vaccinium Myrtillus*, Valerian, Valeriana *Officinalis*, Vandalroot, *Vanilla, Vanilla fragrans*, Vanilla Grass, *Vanilla planifolia*, Varuna, Vegetable Antimony, Vegetable Marrow, Vegetable Sulfur, Vegetable Tallow, Vegetable Wax, Venus' Basin, Venus'-hair Fern, *Verbascum Thapsus*, Verbena, *Verbena Officinalis*, Vermont Valerian, Vemonia *Amygdalina, Veronica Beccabunga, Veronica Officinalis*, Vervain, Vetiver, *Vetiveria zizanioides*, Vetivert, Vibumum *Opulus, Viburnum* Prunifolium, Vietnamese Cilantro, Vietnamese Coriander, Vietnamese Mint, *Vinca Minor, Vinca Rosea*, Vine, *Viola Odorata, Viola* Tricolor, Violet-bloom, Virginia Bugleweed, Virginia Dogwood, Virginia Prune, Virginia Skullcap, Virginia Snakeroot, Virginia Water Horehound, Viscum Album, Visnaga, Vitellaria *paradoxa*, Vitex, Vitex Agnus-Castus, *Vitis Vinifera*, Vomitroot, Wachsgagl, Wakame, Wake Robin, Waldmeister, Wallflower, Walnut, Wasabi, Wasabia *japonica*, Wasei, Water Bugle, Watercress, Water Dragon, Water Flag, Water Horehound, Water Hyssop, Water Lily, Water Mint, Water Pimpernel, Water Shamrock, Water Thistle, Wattle, Wax Cluster, Wax Dolls, Wax Myrtle, Way Bennet, Weeping Ash, Weeping Forsythia, Wheatgrass, Whinberry, Whippoorwill's-shoe, Whistling Thorn, White Archangel, White Ash, White Birch, White Bird's-eye, White Bryony, White Cedar, White Ceremonial Sage, White Chamomile, White Clover, White Deadnettle, White Endive, White Flower De Luce, White Horehound, White Jelly-leaf, White Muer, White Lotus, White Mustard, White Nettle, White Pine, White Poplar, White Sage, White Tansy, Whitethom, White Tree-ear, White Turmeric, White Walnut, White Willow, Whitten Tree, Whorlywort, Whortleberry, Whorts, Wild Allspice, Wild *Angelica*, Wild Black Cherry, Wild Brier, Wild Bryony, Wild Carrot, Wild Celery, Wild Chamomile, Wild Chicory, Wild Cotton, Wild *Crocus*, Wild Endive, Wild Fennel, Wild Geranium, Wild Hops, Wild Indigo, Wild Iris, Wild Lemon, Wild Lettuce, Wild Mandrake, Wild Marjoram, Wild Oats, Wild Opium, Wild Pansy, Wild Parsnip, Wild Passionflower, Wild Pieplant, Wild Rhubarb, Wild Rye, Wild Snakeroot, Wild Strawberries, Wild Succory, Wild Sunflower, Wild Sweetsop, Wild Tansy, Wild Teasel, Wild Thyme, Wild Tobacco, Wild Valerian, Wild Vine, Wild Yam, Willow, Willow Herb, Windflower, Wind Root, Wineberry, Winter Berry, Winterbloom, Winter Cherry, Winter Clover, Wintergreen, Winterlien, Winter Marjoram, Winter Savory, Winter Thyme, Winterweed, Witches'-moneybags, Witchgrass, Witch Hazel, Witch's Bells, Withania, Withania Somnifera, Wolfsbane, Wolfs Claw, Woman's Long Hair, Wood Betony, Woodbine, Wood Boneset, Wood Ear Fungus, Woodland Germander, Woodland Strawberry, Wood Licorice, Woodruff, Wood Sage, Wood Strawberry, Wood Turmeric, Wood Vine, Woodward, Woody Nightshade, Woolly Mint, Woolly Thistle, Worm Grass, Wormseed, Wormweed, Wormwood, Woundwort, Wu-pa-ho, Wu-wei-zi, Wycopy, Xiao-hue-xiang, Xi Shu, Xu Ku Cao, Yacon, Yacuma, Yang-Mei, Yape, Yarrow, Yasmin, Yasti Madhu, Yawroot, Yellow Bedstraw, Yellow Cedar, Yellow Dock, Yellow Eye, Yellow *Ginseng*, Yellow Indian Paint, Yellow Indian Shoe, Yellow Indigo, Yellow Jasmine, Yellow Jessamine, Yellow Lark's Heels, Yellow Locust, Yellow Loosestrife, Yellow Melilot, Yellow Mustard, Yellow Paint Root, Yellow Poppy, Yellow Puccoon, Yellow Rocket, Yellowroot, Yellow Thistle, Yellow Vine, Yerba, Yerba Buena, Yerba Mansa, Yerba Manza, Yerba Santa, Yin-hsing, Yin Yang Huo, Ylang Ylang Tree, Yohimbe, Yohimbine, *Yucca, Yucca* spp., Yueh-kuei, Yuma, Yu Mi Shu, Yuzu, Yuyu Chonta, Zaatar, Zacate *Limon*, Zanthoxylum *Americanum*, Zea Mays, Zedoary, or *Zingiber Officinale*.

Probiotics can also be included in *cannabis* oil compositions prepared according to the invention. Examples of suitable probiotics include, but are not limited to, *Acinetobacter calcoaceticus, Arthrobacter agilis, Arthrobacter citreus, Arthrobacter globiformis, Arthrobacter luteus, Arthrobacter simplex, Azotobacter chroococcum, Azotobacter paspali, Azospirillum brasiliense, Azospirillum lipoferum, Bacillus* ssp. (e.g., *Bacillus brevis, Bacillus coagulans, Bacillus laterosporus, Bacillus marcerans, Bacillus pumilus, Bacillus polymyxa, Bacillus sphaericus, Bacillus subtilis*), *Bacteroides lipolyticum, Bacteroides succinogenes, Bifidobacterium* ssp. (e.g., *Bifidobacterium animalis lactis, Bifidobacterium bifidum, Bifidobacterium infantis, Bifidobacterium lactis, Bifidobacterium longum, Bifidobacterium animalis, Bifidobacterium breve), Brevibacterium lipolyticum, Brevibacterium stationis, Enterococcus faecium, Kurthia zopfii, Lactobacillus* ssp. (e.g., *Lactobacillus acidophilus, Lactobacillus brevis, Lactobacillus bulgaricus, Lactobacillus casei, Lactobacillus delbrueckii LE, Lactobacillus gasseri, Lactobacillus helveticus, Lactobacillus lacris, Lactobacillus paracasei, Lactobacillus plantarumtarum, Lactobacillus reuteri, Lactobacillus rhamnosus, Lactobacillus salivarius, Lactobacillus sporogenes), Myrothecium verrucaria, Pseudomonas calcis, Pseudomonas dentrificans, Pseudomonas fluorescens, Pseudomonas glathei, Phanerochaete chrysosporium, Saccharomyces boulardii, Saccharomyces cerevisiae, Streptococcus thermophilus, Streptomyces fradiae, Streptomyces cellulosae, Streptomyces griseoflavus*, and combinations thereof.

Homeopathic remedies can also be included in *cannabis* oil compositions prepared according to the invention. Examples of suitable homeopathic remedies and indications that can be treated with homeopathic remedies include, but are not limited to, adrenocorticotropic hormone (ATCH), *Abies Canadensis, Abies* Nigra, *Abrotanum, Absinthium, Acacia Arabica,* Acalypha Indica, Acetaldehyde, Acetanilidum, *Aceticum* Acidum, Acetylsalicylicum Acidum, Achyranthis Calea, Aconite, or Aconitum Nap, Aconitum *Ferox*, Aconitum Lycoctonum, Aconitum Napellus, Aconitum, Radix, Acorus *Calamus*, or *Calamus, Actaea Spicata* Acrylate, *Actaea* Rac, or Cimicifuga, *Actaea* Spic, Adamas, Adelheidsquelle, Adenosinum Cyclophosphoricum, Adeps Suillus, Adipose Tissue, *Adonis* Vemalis, Adrenal Cortex, Adrenal Gland, Adrenalinum, or Epinephrine, Adrenocorticotrophin, Aesculinum, *Aesculus* Camea, Flos, *Aesculus Glabra, Aesculus Hippocastanum, Aesculus Hippocastanum* Flos, *Aethiops* Antimonialis, *Aethiops Mercurialis*-Mineralis, Aethusa Cynapium, Agaricinum, *Agaricus* Campanulatus, *Agaricus Campestris, Agaricus Citrinus, Agaricus* Emeticus, *Agaricus* Muscarius, *Agaricus* Pantherinus, *Agaricus Phalloides, Agaricus* Procerus, *Agaricus* Semiglobatus, *Agaricus* Stercorarius, Agave Americana, Agave Tequilana, Agnus Castus, Agraphis *Nutans*, Agrimonia *Eupatoria*, Agrimonia *Eupatoria*, Flos, Agrimonia *Odorata*, Flos, *Agrostemma Githago, Ailanthus* Glandulosus, Aletris *Farinosa*, Alfalfa, Alisma *Plantago, Allium Cepa, Allium Sativum*, Alloxanum, *Alnus Glutinosa, Alnus Serrulata, Aloe Socotrina*, Alstonia *Constricta*, Alstonia Scholaris, Althaea *Officinalis*, Alumen, or Alum, Alumina, Alumina Silicata, Aluminum Metallicum, Aluminum Muriaticum, Ambra *Grisea, Ambrosia* Artemisiaefolia, Ammi Visnaga, Ammoniacum Gummi, Ammonium *Aceticum*, Ammonium Benzoicum, Ammonium Bromatum, Ammonium Carbonicum, Ammonium Causticum, Ammonium Citricum, Ammonium Iodatum, Ammonium Muriaticum, Ammonium Nitricum, Ammonium Phosphoricum, Ammonium Picricum, Ammonium Tartaricum, Ammonium Valerianicum, Ammonium Vanadium, Amorphophallus Rivieri, Ampelopsis *Quinquefolia*, Amygdala *Amara*, Amygdalae *Amarae* Aqua, Amygdalae *Amarae* Oleum, Amygdalus *Persica*, Amyl Nitrosum, *Anacardium Occidentale, Anacardium Orientale*, Anagallis *Arvensis, Ananassa*, Anas Barbariae Hepatis Et Cordis Extractum, Anatherum *Muricatum*, Anchusa *Officinalis, Anemone Nemorosa, Anemopsis Califomica, Anethum Graveolens, Angelica Archangelica, Angelica Atropurpurea, Angelica sinensis*, Radix, Angophora *Lanceolata*, Angustura Vera, Anhalonium Lewinii, Anilinum, Anilinum Sulphuricum, Anisum, *Anthemis Nobilis, Anthemis* Pyrethrum, *Anthoxanthum Odoratum*, Anthracinum (anthrax), Antimonium Arsenicicum, Antimonium Crudum, Antimonium Iodatum, Antimonium Muriaticum, Antimonium Oxydatum, Antimonium Sulphuratum *Aureum*, Antimonium Tartaricum, Antipyrinum, Apatite, Apiolum, Apis Mellifica, Apis Venenum Purum, *Apium Graveolens*, Apocynum Androsaemifolium, Apocynum Cannabinum, Apomorphinum, Apomorphinum Muriaticum, Aqua Marina, Aquilegia Vulgaris, *Aralia Hispida, Aralia Quinquefolia, Aralia Racemosa*, Aranea Diadema, Arbutinum, *Arbutus Andrachne, Areca Catechu, Argemone Mexicana*, Argentum Cyanatum, Argentum Iodatum, Argentum Metallicum, Argentum Muriaticum, Argentum Nitricum, Argentum Oxydatum, Argentum Phosphoricum, Aristolochia Clematitis, Aristolochia Milhomens, Aristolochia Serpentaria, Amica Montana, Amica Montana, Radix, Arsenicum Album, Arsenicum Bromatum, Arsenicum Iodatum, Arsenicum Metallicum, Arsenicum Sulphuratum Flavum, Arsenicum Sulphuratum *Rubrum, Artemisia Vulgaris, Arum* Dracontium, *Arum Italicum, Arum Maculatum, Arum Triphyllum, Arundo* Mauritanica, Asafoetida, *Asarum Canadense, Asarum Europaeum*, Asclepias Curassavica, Asclepias Incamata, Asclepias *Syriaca*, Asclepias *Tuberosa*, Asclepias Vincetoxicum, Asclepias Vincetoxicum Folia, *Asimina Triloba, Asparagus Officinalis, Asperula Odorata*, Astacus *Fluviatilis*, Asterias *Rubens, Astragalus Menziesii*, Atropinum, Atropinum Sulphuricum, *Aurum* Bromatum, *Aurum* Iodatum, *Aurum* Met, *Arum* Mur, *Aurum* Muriaticum Kalinatum, *Aurum* Muriaticum Natronatum, *Aurum* Sulphuratum, *Avena Sativa*, Aviaire, Azadirachta Indica, Bacillinum of Burnet, Badiaga, Baja, Balsamum Peru, Baptisia *Tinctoria*, Barosma Cren, Baryta Acetica, Baryta Carbonica, Baryta Iodata, Baryta Muriatica, BCG, *Belladonna, Belladonna*, Radix, *Bellis Perennis*, Benzinum, Benzinum Dinitricum, Benzoicum Acidum, Benzoinum, Berberinum, *Berberis Aquifolium, Berberis Vulgaris, Berberis Vulgaris*, Fructus, Beryllium Metallicum, *Beta Vulgaris*, Betainum Muriaticum, *Betula Pendula*, Cortex, *Betula Pendula*, Folia, Bismuthum Metallicum, Bismuthum Oxydatum, Bismuthum Subnitricum, *Bixa Orellana, Blatta* Americana, *Blatta Orientalis*, Boldo, *Boletus Luridus, Boletus Satanas, Bombyx* Processionea, *Borago Officinalis*, Borax, Boricum Acidum, Botulinum, Bovista, *Brassica Napus*, Bromelain, Bromium, *Bromus Ramosus*, Flos, Brucinum, Bryonia Alba, *Bufo* Rana, Bunias *Orientalis*, Buthus *Australis, Butyricum* Acidum, *Buxus Sempervirens*, Cacao, Cactus *Grandiflorus*, Cadmium Bromatum, Cadmium Iodatum, Cadmium Metallicum, Cadmium Muriaticum, Cadmium Sulphuratum, Cadmium Sulphuricum, Caffeinum, Cahinca, Cajuputum, *Caladium* Seguinum, *Calcarea* Acetica, *Calcarea* Arsenicica, *Calcarea* Carbonica, *Calcarea* Caustica, *Calcarea* Fluorica, *Calcarea* Hypochlorata, *Calcarea* Hypophosphorosa, *Calcarea* Iodata, *Calcarea* Lactica, *Calcarea* Muriatica, *Calcarea* Oxalica, *Calcarea* Phosphorica, *Calcarea* Picrata, *Calcarea* Silicata, *Calcarea* Sulphurica, *Calendula Officinalis, Calluna Vulgaris*, Flos, Calotropis *Gigantea*, Caltha *Palustris, Camphora, Camphora* Monobromata, Camphoricum Acidum, Canchalagua, *Candida Albicans, Candida Parapsilosis*, Canine Dapp, Cantharidinum, Cantharis, *Capsicum, Capsicum Annuum*, Carbo *Animalis*, Carbo Vegetabilis, Carbolicum Acidum, Carboneum, Carboneum Chloratum, Carboneum Hydrogenisatum, Carboneum Oxygenisatum, Carboneum Sulphuratum, Carcinosinum, Cardiospermum, *Carduus Benedictus, Carduus* Marianus, *Carpinus Betulus*, Flos, Cartilago Suis, *Carum Carvi*, Cascarilla, Cassada, *Castanea Sativa*, Flos, *Castanea Vesca*, Castor Equi, Castoreum, *Catalpa* Bignonioides, Caulophyllum *Thalictroides*, Causticum, Ceanothus *Americanus*, Cedron, *Celtis Occidentalis*, Cenchris Contortrix, *Centaurea* Tagana, *Centaurium Umbellatum*, Flos, Cephalanthus *Occidentalis, Cerasus Virginiana*, Ceratostigma Willmottianum, Flos, *Cereus Bonplandii, Cereus* Serpentinus, Cerium *Oxalicum*, Cetraria *Islandica, Chamomilla, Cheiranthus Cheiri, Chelidonium Majus, Chelidonium Majus*, Radix, *Chelone Glabra, Chenopodii Glauci Aphis, Chenopodium* Anthelminticum, *Chenopodium Vulvaria, Chimaphila Maculata, Chimaphila Umbellata*, Chininum Arsenicicum, Chininum Arsenicosum, Chininum Muriaticum, Chininum Purum, Chininum Salicylicum, Chininum Sulphuricum, *Chionanthus Virginica*, Chloralum, Chloramphenicolum, Chlorinum, Chloroforum, Chlorpromazinum, Cholera, Cholesterinum, Cholinum, Chromicum Acidum, Chromium *Kali* Sulphuricum, Chromium Oxydatum, Chromium Sulphuricum, *Chrysanthemum Leucanthemum*, Chrysarobinum, *Cicer Arietinum, Cichorium Intybus, Cichorium Intybus*, Flos, *Cicuta Maculata, Cicuta Virosa, Cimex Lectularius*, Cimicifuga *Racemosa, Cina*, Cinchona *Officinalis*, Cinchonium Sulphuricum, *Cineraria Maritima, Cineraria Maritima*, Succus, *Cinnamomum, Cistus Canadensis*, Citricum Acidum, *Citrus Decumana, Citrus Limonum, Citrus Vulgaris, Clematis Erecta, Clematis Virginiana, Clematis Vitalba*, Flos, *Clematis Vitalba*, Folia, Cobaltum Metallicum, Cobaltum Muriaticum, Cobaltum Nitricum, Coccinella Septempunctata, Cocculus *Indicus*, Coccus Cacti, *Cochlearia Armoracia, Cochlearia Officinalis*, Coenzyme A, *Coffea* Cruda, *Coffea* Tosta, Colchicinum, *Colchicum Autumnale*, Colibacillinum, *Collinsonia Canadensis*, Colocynthinum, Colocynthis, Colostrum, Comocladia *Dentata*, Conchiolinum, Condurango, Coniinum, Coniinum Bromatum, *Conium Maculatum, Convallaria Majalis, Convolvulus Arvensis*, Copaiva *Officinalis*, Corallium *Rubrum*, Corallorhiza Odontorhiza, *Coriaria* Ruscifolia, *Cornus* Altemifolia, *Cornus* Circinata, Comus Florida, Cortisone *Aceticum*, Corydalis *Canadensis*, Cotyledon Umbilicus, Coumarinum, *Crataegus Oxyacantha*, Cresolum, Crocus Sativus, Crotalus Cascavella, *Crotalus Horridus*, Croton Tiglium, Crotonchloralum, *Cubeba Officinalis, Cucurbita Citrullus, Cucurbita Pepo*. Flos, *Cucurbita Pepo*, Semen, *Culex Musca, Cuphea Petiolata, Cupressus Australis, Cupressus Lawsoniana*, Cuprum *Aceticum*, Cuprum Ammonio-Sulphuricum, Cuprum Arsenicosum, Cuprum Carbonicum, Cuprum Metallicum, Cuprum Muriaticum, Cuprum Nitricum, Cuprum Oxydatum *Nigrum*, Cuprum Sulphuricum, Curare, Cyclamen *Europaeum, Cydonia* Vulgaris, Cynara Scolymus, *Cynodon Dactylon, Cypripedium Pubescens*, Cysteinum, *Cytisus Scoparius*, Damiana, Daphne Indica, *Datura Arborea, Datura Metel*, DDT, Delphininum, Derris *Pinnata, Dichapetalum*, Dictamnus *Albus*, Digitalinum, *Digitalis Purpurea*, Digitoxinum, *Dioscorea Villosa*, Dioscoreinum, Diphtherinum, Diphtherotozinum, Diptherinum, Diptherotoxinum, Dirca *Palustris*, DNA, *Dolichos Pruriens*, Doryphora *Decemlineata*, Draba Vema, Drosera *Rotundifolia*, DTTAB (Diptheria), *Duboisia Myoporoides, Dulcamara, Dulcamara*, Flos, Dysentery, *E. Coli*, Ear, Labyrinth of (inner ear), Ear, Middle, Eberthinum, *Echinacea Angustifolia, Echinacea Purpurea, Elaeis Guineensis*, Elaps Corallinus, Elaterium, Embryo Suis, Emetinum, Enterotoccinum, Eosinum Natrum, Ephedra Vulgaris, *Epigaea Repens*, Epilobium *Palustre*, Epiphegus *Virginiana*, Equisetum *Arvense*, Equisetum Hyemale, Eranthis *Hyemalis*, Erechtites Hieracifolia, Erigeron *Canadensis*, Eriodictyon Califomicum, Erodium, Eryngium *Aquaticum*, Eryngium *Maritimum*, Erythraea *Centaurium*, Eschscholtzia Califomica, Eserinum, Etherum, Ethylicum, Ethylum Nitricum, Eucalyptol, *Eucalyptus Globulus*, Eugenia Caryophyllata, Eugenia Jambosa, *Euonymus* Atropurpureus, *Euonymus Europaeus*, Eupatorium *Aromaticum*, Eupatorium Cannabinum, Eupatorium *Perfoliatum*, Eupatorium *Purpureum*, *Euphorbia Amygdaloides*, *Euphorbia Corollata*, *Euphorbia Cyparissias*, *Euphorbia Hypericifolia*, *Euphorbia Lathyris*, *Euphorbia* Pilulifera, Euphorbium *Officinarum*, Euphrasia *Officinalis*, Eupion, Eyebright herb, *Fagopyrum Esculentum, Fagus Sylvatica, Fagus Sylvatica*, Flos, Fel Tauri, Ferrum *Aceticum*, Ferrum Arsenicicum, Ferrum Bromatum, Ferrum Carbonicum, Ferrum Citricum, Ferrum Cyanatum, Ferrum Iodatum, Ferrum Lacticum, Ferrum Metallicum, Ferrum Muriaticum, Ferrum Pemitricum, Ferrum Phosphoricum, Ferrum Picricum, Ferrum Sulphuricum, Ferrum Tartaricum, Ferula *Glauca*, *Ficus* Religiosa, Filix Mas, *Foeniculum Vulgare*, Folliculinum, Formalinum, Formica *Rufa*, Formicum Acidum, Fragaria *Vesca*, Franciscea *Uniflora*, *Fraxinus Americana*, *Fraxinus Excelsior*, Fuchsinum, Fucus Vesiculosus, *Fumaria Officinalis*, Fumaricum Acidum, *Funiculus* Umbilicalis Suis, *Galanthus Nivalis, Galega Officinalis, Galium Aparine, Gallicum* Acidum, Galphimia *Glauca*, Gambogia, Garlic, *Gaultheria Procumbens, Gelsemium Sempervirens, Genista Tinctoria, Gentiana* Cruciata, *Gentiana Lutea, Gentiana Quinqueflora*, Gentianella Amarella, Flos, Geranium *Maculatum*, Geranium *Robertianum, Geum Rivale, Geum Urbanum, Ginkgo biloba*, Glandula Suprarenalis Suis, *Glechoma Hederacea*, Glonoinum, Glycerinum, Glycogenum, *Glycyrrhiza Glabra*, Gnaphalium Leontopodium, Gnaphalium Polycephalum, Gnaphalium *Uliginosum*, Gonotoxinum, *Gossypium Herbaceum*, Granatum, Graphites, Gratiola *Officinalis*, Grindelia, Guaco, *Guaiacum*, Guarea Trichilioides, Guatteria *Gaumeri, Gunpowder, Gymnocladus Canadensis*, Haematoxylon Campechianum, *Haemophilus* Infl. B, Hair Bulb, Pilo Sebaceous Zone, HamamelisVirginiana, Haronga Madagas-*cariensis*, Hedeoma Pulegioides, *Hedera Helix*, Hekla Lava, *Helianthemum* Nummularium, Flos, *Helianthus Annuus, Heliotropium Peruvianum*, Helix Tosta, *Helleborus Foetidus, Helleborus Niger, Helleborus Viridis*, Heloderma, Helonias *Dioica*, Hepar Suis, Hepar Sulphuris Calcareum, Hepar Sulphuris Kalinum, *Hepatica Triloba*, Hepatitis A, Hepatitis B, Hepatitis C, *Heracleum* Sphondylium, Herpes Zoster, Hippozaeninum, Hippuricum Acidum, Hirudinum, Histaminum Hydrochloricum, Hoang-Nan, Hoitzia *Coccinea*, Holarrhena Antidysenterica, *Homarus*, Hottonia *Palustris*, Flos, *Humulus Lupulus*, Hura *Brasiliensis*, Hura Crepitans, *Hydrangea Arborescens*, Hydrastininum Muriaticum, Hydrastis *Canadensis*, Hydrocotyle *Asiatica*, Hydrocyanicum Acidum, Hydrofluoricum Acidum, Hydrophis Cyanocinctus, Hydrophyllum *Virginianum*, Hyoscyaminum, Hyoscyaminum, Hydrobromatum, *Hyoscyamus Niger, Hypericum* Perforatum, Hypothalamus, *Iberis Amara*, Ichthyolum, Ignatia *Amara, Ilex Aquifolium, Ilex Aquifolium*, Flos, *Ilex Paraguariensis*, Illicium Anisatum, *Impatiens Glandulifera*, Flos, Imperatoria Ostruthium, Indigo, Indium Metallicum, Indolum, Influenzinum, Inula Helenium, Iodium, Iodoformum, Ipecacuanha, *Ipomoea Stans*, Iridium Metallicum, *Iris Florentina, Iris Foetidissima, Iris Germanica, Iris Tenax, Iris Versicolor, Jacaranda* Caroba, *Jalapa, Jasminum Officinale*, Jasper, Jatropha Curcas, Jatropha *Urens*, Jequirity, Jonesia Asoca, *Juglans Cinerea, Juglans Regia, Juglans Regia*, Flos, Juncus Effusus, *Juniperus Communis, Juniperus Virginiana*, Justicia Adhatoda, *Kali* Aceticum, *Kali* Arsenicosum, *Kali* Bichromicum, *Kali* Bromatum, *Kali* Carbonicum, *Kali* Causticum, *Kali* Chloricum, *Kali* Chromicum, *Kali* Cyanatum, *Kali* Ferrocyanatum, *Kali* Iodatum, *Kali* Muriaticum, *Kali* Nitricum, *Kali* Oxalicum, *Kali* Permanganicum, *Kali* Phosphoricum, *Kali* Picricum, *Kali* Silicatum, *Kali* Sulphuricum, *Kali* Tartaricum, *Kali* Telluricum, *Kalmia Latifolia*, Kamala, Karaka, Karwinskia Humboldtiana, Kino *Australiensis*, Kousso, Kreosotum, *Laburnum Anagyroides*, Lac *Caninum*, Lac Defloratum, Lac *Felinum*, Lac Matemum, Lac Vaccinum, Lacerta *Agilis*, Lachesis Mutus, Lachnanthes *Tinctoria*, Lacticum Acidum, *Lactuca Virosa, Lamium Album*, Lapis *Albus, Lappa* Major, *Larix Decidua*, Flos, *Lathyrus* Cicera, *Lathyrus Sativus, Latrodectus* Katipo, *Latrodectus Mactans, Laurocerasus*, Lecithin granules, Lecithin potenized, Ledum *Palustre, Lemna Minor, Leonurus Cardiaca, Lepidium* Bonariense, Leptandra *Virginica, Lespedeza Capitata*, Levico, *Levisticum Officinale*, Levomepromazinum, Liatris *Spicata, Lilium* Tigrinum, Limulus, Linaria Vulgaris, *Linum Catharticum, Linum Usitatissimum*, Lithium Benzoicum, Lithium Bromatum, Lithium Carbonicum, Lithium Muriaticum, *Lobelia Cardinalis, Lobelia* Erinus, *Lobelia Inflata, Lobelia Purpurescens, Lobelia* Syphilitica, Lobelinum, *Lolium Temulentum, Lonicera* Caprifolium, Flos, *Lonicera* Periclymenum, *Lonicera* Xylosteum, Lophophytum Leandri, Luesinum, Luffa Operculata, Lupulinum, *Lycopersicum Esculentum*, Lycopodium *Clavatum, Lycopus Virginicus, Lysimachia Nummularia*, Lyssin, Lyssinum, Macrotinum, Magnesia Carbonica, Magnesia Muriatica, Magnesia Oxydata, Magnesia Phosphorica, Magnesia Sulphurica, Magnesium Metallicum, *Magnolia Glauca, Magnolia Grandiflora*, Malaria Off., *Malus Pumila*, Flos, *Mancinella*, Mandragora *Officinarum*, Manganum *Aceticum*, Manganum Carbonicum, Manganum Metallicum, Manganum Muriaticum, Manganum Oxydatum Nativum, Manganum Oxydatum *Nigrum*, Manganum Phosphoricum, Manganum Sulphuricum, *Mangifera Indica, Marrubium Vulgare*, Matico, *Matthiola Graeca*, Medorrhinum (Gonorrheal virus), Medulla Ossis Suis, Medusa, Melastoma Ackermani, Melilotus Alba, Melilotus *Officinalis, Melissa Officinalis*, Menispermum *Canadense, Mentha Piperita, Mentha Pulegium, Mentha Viridis*, Mentholum, Menyanthes *Trifoliata, Mephitis* Mephitica, *Mercurialis Perennis*, Mercurius Aceticus, Mercurius Auratus, Mercurius Bromatus, Mercurius Corrosivus, Mercurius Cum *Kali* Iodatus, Mercurius Cyanatus, Mercurius *Dulcis*, Mercurius Iodatus *Flavus*, Mercurius Iodatus *Ruber*, Mercurius Methylenus, Mercurius Nitricus, Mercurius Praecipitatus *Albus*, Mercurius Praecipitatus *Ruber*, Mercurius Solubilis, Mercurius Sulphocyanatus, Mercurius Sulphuratus *Ruber*, Mercurius Sulphuricus, Mercurius Vivus, Methylene Blue, Mezereum, *Millefolium, Mimosa Pudica*, Mimulus Guttatus, Flos, *Mitchella Repens, Momordica Balsamina*, Mononucleosis, Monotropa *Uniflora*, Morbillinum (Measles), Moschus, Mucosa Nasalis Suis, Mullein Essence, Murex *Purpurea*, Muriaticum Acidum, Musa Sapientum, Mygale, *Myosotis Arvensis, Myrica* Cerifera, *Myristica Sebifera*, Myrrha, *Myrtus Communis*, Nabalus Serpentarius, Nadidum, Naja Tripudians, Naphthalinum, Narceinum, *Narcissus*, Pseudo-, *Narcissus*, Narcotinum, Nasturtium *Aquaticum*, Natrum Arsenicicum, Natrum Bicarbonicum, Natrum Bromatum, Natrum Carbonicum, Natrum Fluoratum, Natrum Hypochlorosum, Natrum Lacticum, Natrum Muriaticum, Natrum Nitricum, Natrum Nitrosum, Natrum Oxalaceticum, Natrum Phosphoricum, Natrum Pyruvicum, Natrum Salicylicum, Natrum Silicofluoricum, Natrum Sulphuratum, Natrum Sulphuricum, Natrum Sulphurosum, *Negundo*, Nepenthes, *Nepeta Cataria*, Niccolum Carbonicum, Niccolum Metallicum, Niccolum Sulphuricum, Nicotinamidum, Nicotinum, Nitri Spiritus *Dulcis*, Nitricum Acidum, Nitrogenum Oxygenatum, Nitromuriaticum Acidum, Nosode Kit, Nosode-Select your own, Nuclear Radiation, *Nuphar Luteum*, Nux Moschata, Nux Vomica, *Nymphaea Odorata*, *Ocimum Basilicum*, *Ocimum Canum*, *Ocimum* Sanctum, *Oenanthe Crocata*, *Oenothera Biennis*, *Olea Europaea*, Flos, *Oleander*, Oleum Animale, Oleum *Carvi*, Oleum Morrhuae, Oleum Ricini, Oleum Santali, Olibanum, Oniscus, Ononis *Spinosa*, *Onopordum*, Onosmodium *Virginianum*, Oophorinum, Opuntia Vulgaris, Orchitinum, Oreodaphne Califomica, *Origanum Majorana*, Omithogalum *Umbellatum*, Omithogalum *Umbellatum, Flos, Oroticum* Acidum, Oscillococcinum, Osmium Metallicum, *Ostrya*, Ova Tosta, Ovi *Gallinae* Pellicula, *Oxalicum* Acidum, Oxalis *Acetosella*, *Oxydendrum Arboreum*, Oxytropis Lambertii, *Paeonia Officinalis*, Palladium Metallicum, Paloondo, Pancreas Suis, Pancreatinum, Paraffinum, Parathormonum, Parathyroid, Paratyphoidinum B, Pareira Brava, *Parietaria Officinalis*, Paris Quadrifolia, Paronichia Illecebrum, Parotidinum (Mumps), *Parthenium, Passiflora* Incamata, *Pastinaca Sativa*, Paullinia *Pinnata*, Paullinia Sorbilis, *Pecten, Pediculus* Capitis, Penicillinum, Penthorum Sedoides, Pepsinum, Perhexilinum, *Persea Americana*, Pertussinum (Whooping Cough), Petiveria *Tetrandra*, Petroleum, Petroselinum *Sativum*, Phallus Impudicus, *Phaseolus*, Phellandrium *Aquaticum*, Phenacetinum, Phenobarbitalum, Phloridzinum, Phosphoricum Acidum, Phosphorus, Physalis Alkekenge, Physotigma *Venenosum, Phytolacca* Decandra, Pichi, Picricum Acidum, Picrotoxinum, Pilocarpinum, Pilocarpinum Muriaticum, Pilocarpinum Nitricum, Pilocarpus, Pimenta *Officinalis*, Pimpinella Saxifraga, *Pinus Lambertiana, Pinus Sylvestris, Pinus Sylvestris*, Flos, *Piper Methysticum, Piper Nigrum*, Piperazinum, Piscidia *Erythrina*, Pituitarum Posterium, Pix Liquida, Placenta Totalis Suis, Plague, *Plantago Major, Platanus*, Platinum Metallicum, Platinum Muriaticum, Plectranthus *Fruticosus*, Plumbago *Littoralis*, Plumbum *Aceticum*, Plumbum Carbonicum, Plumbum Chromicum, Plumbum Iodatum, Plumbum Metallicum, Pneumococcinum, Podophyllinum, *Podophyllum Peltatum*, Polio, *Polygonum* Punctatum, *Polygonum* Sagittatum, Polyporus *Officinalis*, Polyporus Pinicola, *Populus Candicans, Populus Tremula*, Flos, *Populus Tremuloides*, Potentilla *Anserina*, Pothos *Foetidus*, *Primula Obconica*, *Primula* Veris, *Primula* Vulgaris, *Proteus* Bulgaris, *Proteus Vulgaris, Prunus Cerasifera*, Flos, *Prunus Padus, Prunus Spinosa, Prunus Virginiana*, Psorinum, Ptelea *Trifoliata, Pulex Irritans, Pulsatilla Niger, Pulsatilla* Nuttalliana, Pyrethrum *Parthenium*, Pyridoxinum Hydrochloricum, Pyrogeniumsepsis, *Pyrus* Americana, Quassia *Amara, Quebracho, Quercus* Glandium Spiritus, *Quercus Robur, Quercus Robur*, Flos, Quillaja *Saponaria*, Radium Bromatum, *Ranunculus Acris, Ranunculus Bulbosus, Ranunculus Ficaria, Ranunculus Glacialis, Ranunculus Repens, Ranunculus Sceleratus, Raphanus Sativus*, Ratanhia, Rauwolfia *Serpentina*, Reserpinum, Resina *Laricis, Resorcinum, Rhamnus* Califomica, *Rhamnus Cathartica, Rhamnus* Frangula, *Rhamnus Purshiana*, Rheum *Officinale*, Rhodium Metallicum, *Rhododendron* Chrysanthum, *Rhus Aromatica, Rhus* Diversiloba, *Rhus Glabra, Rhus Toxicodendron, Rhus Venenata*, Riboflavinum, *Ricinus Communis*, RNA, *Robinia Pseudoacacia*, Rock Water, *Rosa Canina, Rosa Canina*, Flos, *Rosa Damascena, Rosmarinus Officinalis*, Rubella (German Measles), Rubeola (Measles), *Rubia Tinctorum, Rumex Acetosa, Rumex Crispus, Rumex Obtusifolius, Russula* Foetens, *Ruta Graveolens*, Sabidilla, *Sabal Serrulata, Sabina, Saccharinum, Saccharum Lactis, Saccharum Officinale*, Salicinum, Salicylicum Acidum, *Salix Alba, Salix Nigra, Salix Purpurea, Salix* Vitellina, Flos, *Salmonella*, Salol, *Salvia Officinalis*, Samarskite, *Sambucus Canadensis*, *Sambucus Nigra, Sanguinaria Canadensis*, Sanguinarinum Nitricum, Sanicula, Santoninum, *Saponaria Officinalis*, Saponinum, Sarcode-Select your own organ remedy, Sarcolacticum Acidum, *Sarracenia Purpurea*, Sarsaparilla, *Sassafras Officinale*, Scammonium, Scarlatinum, *Secale*-Ergot *Schinus Molle*, Scilla *Maritima*, Scleranthus *Annuus*, Flos, Scolopendra, Scolopendrium *Vulgare*, Scopolaminum Hydrobromidum, Scrophularia *Nodosa*, Scutellaria Lateriflora, *Secale* Comutum, *Secale*-Ergot, Sedum Acre, Selenium Metallicum, Sempervivum *Tectorum*, *Senecio Aureus*, *Senecio Jacobaea*, Senega *Officinalis*, *Senna*, Sepia, Serum *Anguillae*, Serum Anticolibacillaire, Serum De Yersin, Serum Equi, *Shigella*, Silica Marina, Silicea, Silphium *Laciniatum, Sinapis Alba, Sinapis Arvensis*, Flos, *Sinapis* Nigra, Sinusitisinum, Sium *Latifolium*, Skatolum, Skookum Chuck, Slag, Solaninum, *Solanum* Arrebenta, *Solanum* Carolinense, *Solanum* Mammosum, *Solanum Nigrum*, *Solanum Oleraceum, Solanum Tuberosum*, Solidago Virgaurea, Sparteinum Sulphuricum, Spigelia Anthelmia, Spigelia *Marilandica*, Spilanthes *Oleracea, Spinacia, Spiraea* Ulmaria, Spiranthes *Autumnalis*, Spongia Encephalitis, Spongia Tosta, Stachys Betonica, Stannum Iodatum, Stannum Metallicum, Staphyloccoccus *Aureus*, Staphylococcinum, Staphylotoxinum, Staphysagria, *Stellaria Media*, Sterculia *Acuminata*, Stibium Metallicum, Sticta Pulmonaria, *Stigmata Maidis*, Stillingia *Sylvatica, Stramonium*, Streptococcinum, Strontium Bromatum, Strontium Carbonicum, Strontium Nitricum, Strophanthus *Hispidus*, Strophanthus Sarmentosus, Strychninum, Strychinum Arsenicicum, Strychinum Nitricum, Strychninum Phosphoricum, Strychninum Sulphuricum, Succinicum Acidum, Succinum, Sulphanilamidum, Sulphonalum, Sulphur, Sulphur Hydrogenisatum, Sulphur Iodatum, Sulphuricum Acidum, Sulphurosum Acidum, Sumbul, Symphoricarpus *Racemosus*, Symphytum *Officinale*, Syphilinum (Luesinum), Syzygium Jambolanum, *Tabacum*, Tamus *Communis, Tanacetum Vulgare*, Tanghinia Venenifera, Tannicum Acidum, *Taraxacum Officinale, Taraxacum Officinale*, Radix, Tarentula *Cubensis*, Tarentula Hispana, Tartaricum Acidum, *Taxus Baccata*, Tellurium Metallicum, Teplitz, Terebinthina, Tetanotoxinum, Tetradymite, *Teucrium Marum, Teucrium Scorodonia*, Thallium Metallicum, Thaspium *Aureum, Thea sinensis*, Theobrominum, Theridion, Thiaminum Hydrochloricum, Thioproperazinum, Thiosinaminum, *Thlaspi Bursa-Pastoris, Thuja* Lobbi, *Thuja Occidentalis*, Thymolum, *Thymus Serpyllum*, Thyroidinum, *Tilia Europaea*, Titanium Metallicum, *Tongo*, Tormentilla, Torula *Cerevisiae*, Toxicophis *Pugnax*, Tradescantia Diuretica, Tribulus *Terrestris, Trifolium Pratense, Trifolium Repens, Trillium* Pendulum, Trimethylaminum, Triosteum *Perfoliatum, Triticum Repens, Tropaeolum Majus*, Tuberculinum, Tuberculinum Residuum, Tussilago Farfara, Tussilago *Fragrans*, Tussilago Petasites, Typhoidinum, *Ulex Europaeus*, Flos, *Ulmus Fulva, Ulmus Procera*, Flos, Upas Tieute, Uranium Nitricum, Urea, Uricum Acidum, *Urtica Crenulata, Urtica Dioica, Urtica Urens*, Usnea *Barbata, Ustilago Maidis*, Uva-*Ursi* herb, Uva-*Ursi*, V.A.B.-BCG, *Vaccinium Myrtillus*, Vaccinotoxinum, Valeriana *Officinalis*, Vanadium Metallicum, Varicella enus Mercenaria (Chicken Pox), Variolinum (Smallpox), Veratrinum, Veratrum Album, Veratrum *Nigrum*, Veratrum *Viride, Verbascum Thapsus, Verbena Hastata, Verbena Officinalis, Verbena Officinalis*, Flos, *Veronica Beccabunga, Veronica Officinalis, Vesicaria, Vespa Crabro, Viburnum Opulus, Viburnum* Prunifolium, *Vinca Minor, Viloa Odorata, Viola* Tricolor, Vipera Berus, Viscum Album, Vitamin B12, Vitamin K, *Vitis Vinifera*, Flos, Wiesbaden, Wyethia *Helenioides*, X-Ray, Xanthoxylum Fraxineum, Xerophyllum Asphodeloides, Yohimbinum, *Yucca Filamentosa*, Zincum *Aceticum*, Zincum Bromatum, Zincum Carbonicum, Zincum Cyanatum, Zincum Gluconicum, Zincum Iodatum, Zincum Metallicum, Zincum Muriaticum, Zincum Oxydatum, Zincum Phosphoratum, Zincum Picricum, Zincum Sulphuricum, Zincum Valerianicum, *Zingiber Officinale*, and combinations thereof.

Flower essences can also be included in *cannabis* oil compositions prepared according to the invention. Examples of suitable flower essences include, but are not limited to, *Acacia, Actaea*, Agrimony, Alpine Lily, Angel's Trumpet, AloeVera, *Angelica*, Basil, Apricot, *Arnica* Beech, Aspen, Avocado, Beech, Bee Balm, Black Cohosh, Baby Blue Eyes, Black-Eyed Susan, Blackberry, Bloodroot, *Calendula*, Bleeding Heart, California Fuchsia, California Pitcher Plant, Borage, Buttercup, California Wild Rose, California Poppy, CallaLily, Cerato, Canyon Dudleya, Chamomile, Cayenne, Cedar, Chaparral, Centaury, *Centaurium* erythraea or *Centaurium umbellatum*, Cerato, Cherry Plum, Chestnut Bud, Corn, Dandelion, Chicory, Cinquefoil, Coffee, Coreopsis, Crab Apple, *Chrysanthemum, Clematis*, Desert Dandelion, Deerbrush, Cosmos, Dill, Elm, Evening Primrose, Dogwood, Easter Lily, *Eucalyptus*, Fairy Lantern, *Echinacea*, Fawn Lily, Fig, Filaree, Gentian, Goldenrod, Forget-Me-Not, Golden Ear Drops, Golden Yarrow, Fuchsia, Garlic, Gorse, Honeysuckle, Heather, Hornbeam, *Hibiscus*, Hound's Tongue, Holly, *Impatiens*, Indian Paintbrush, Larch, Lily, Indian Pink, Larkspur, *Iris, Iris douglasiana/Iris versicolor*, Lady's Slipper, *Cypripedium parviflorum/Cypripedium reginae*, Lotus, Lavender, Love-Lies-Bleeding, Mariposa Lily, Madia, *Magnolia*, Milkweed, Mallow, Mimulus, Manzanita, Morning Glory, Motherwort, Mountain Pennyroyal, Mustard, Mountain Pride, Nasturtium, Mugwort, *Nicotiana*, Noni, Oak, Olive, Pine, Orange, Oregon Grape, Pansy, Passion Flower, Pear, *Petunia*, Pink Angel's Trumpet, Pink Monkeyflower, Penstemon, Pink Yarrow *Achillea millefolium* var. *rubra*, Peppermint, Poison Oak, Pomegranate, Queen Anne's Lace, Pretty Face, Quince, Purple Monkeyflower, Rabbitbrush, Quaking Grass, Red Chestnut, Red clover, Rescue Remedy, Rock Rose, Sacred *Datura*, Sagebrush, Scarlet Pimpernel, Rock Water Solarized spring water, Saguaro, Rosemary, Rose, Saint John's Wort, Scarlet Monkeyflower, Shasta Daisy, Scleranthus, Shooting Star, Scotch Broom, Snapdragon, Squash, Self-Heal, Star of Bethlehem, Star Thistle, Sweet Chestnut, Star Tulip, Strawberry, Sun Cup, Sweet Pea, Sticky Monkeyflower, Tansy, Sunflower, Thyme, Tiger Lily, *Trillium*, Violet, Walnut, Trumpet Vine, Vervain, Water Lily, Water Violet, Vine, White Chestnut, Wild Oat, Wild Rose, Yellow Star Tulip, Willow, Yerba Santa, Yarrow, *Yucca, Zinnia*, and combinations thereof.

In certain embodiments, additional carrier oils are added to the *cannabis* oils. Examples of carrier oils include, but are not limited to, almond oil; *aloe vera* oil; apricot kernel oil; avocado oil; argan oil; *calendula* oil; carrot seed oil; castor oil; coconut oil; evening primrose oil; fish oils and oils rich in omega-3 fatty acids (e.g., algae, krill, flaxseed); grape seed oil; hazelnut oil; hemp seed oil; jojoba oil; macadamia oil; olive oil; raspberry seed oil; sesame oil; sunflower oil; walnut oil; wheatgerm oil, and combinations thereof.

When added, a carrier oil will typically be present in an amount ranging from about 1% (w/w) to about 95% (w/w). A carrier oil can be present, for example, in an amount ranging from about 5% (w/w) to about 10% (w/w), or from about 10% (w/w) to about 15% (w/w), or from about 15% (w/w) to about 20% (w/w), or from about 20% (w/w) to about 25% (w/w), or from about 25% (w/w) to about 30% (w/w), or from about 30% (w/w) to about 35% (w/w), or from about 35% (w/w) to about 40% (w/w), or from about 40% (w/w) to about 45% (w/w), or from about 45% (w/w) to about 50% (w/w), or from about 50% (w/w) to about 55% (w/w), or from about 55% (w/w) to about 60% (w/w), or from about 60% (w/w) to about 65% (w/w), or from about 65% (w/w) to about 70% (w/w), or from about 70% (w/w) to about 75% (w/w), or from about 75% (w/w) to about 80% (w/w), or from about 80% (w/w) to about 85% (w/w), or from about 85% (w/w) to about 90% (w/w), or from about 90% (w/w) to about 95% (w/w). A carrier oil can be present in an amount ranging from about 5% (w/w) to about 95% (w/w), or from about 10% (w/w) to about 90% (w/w), or from about 15% (w/w) to about 85% (w/w), or from about 20% (w/w) to about 80% (w/w), or from about 25% (w/w) to about 75% (w/w), or from about 30% (w/w) to about 70% (w/w), or from about 35% (w/w) to about 65% (w/w), or from about 40% (w/w) to about 60% (w/w), or from about 45% (w/w) to about 55% (w/w).

In some embodiments, the invention provides a *cannabis* oil composition comprising a *cannabis* oil (e.g., a *cannabis* oil extract prepared according to the methods described herein) and hemp seed oil as a carrier oil. In some such embodiments, the *cannabis* oil is present in the *cannabis* oil composition in an amount ranging from about 7% (w/w) to about 70% (w/w). In some such embodiments, hemp seed oil is present in the *cannabis* oil composition in an amount ranging from about 30% (w/w) to about 95% (w/w). In some embodiments, the *cannabis* oil composition further comprises vitamin E. In some such embodiments, the ratio of the hemp seed oil to the vitamin E is around 200:1 by weight. In some such embodiments, vitamin E is present in the *cannabis* oil composition in an amount ranging from about 0.2% (w/w) to about 0.5% (w/w). The composition containing *cannabis* oil, hemp seed oil, and vitamin E can be administered orally via a gelatin capsule such as a vegetarian gel capsule.

In some embodiments, the invention provides a *cannabis* oil composition comprising about 9% (w/w) *cannabis* oil, about 90.5% (w/w) hemp seed oil, and about 0.5% (w/w) vitamin E. In some such embodiments, the *cannabis* oil composition is formulated in a vegetarian gel capsule for oral administration.

In some embodiments, the invention provides a *cannabis* oil composition comprising about 33.3% (w/w) *cannabis* oil, about 66.4% (w/w) hemp seed oil, and about 0.3% (w/w) vitamin E. In some such embodiments, the *cannabis* oil composition is formulated in a vegetarian gel capsule for oral administration.

In some embodiments, the invention provides a *cannabis* oil composition comprising about 66.7% (w/w) *cannabis* oil, about 33.2% (w/w) hemp seed oil, and about 0.2% (w/w) vitamin E. In some such embodiments, the *cannabis* oil composition is formulated in a vegetarian gel capsule for oral administration.

IV. Pharmaceutical Compositions and Methods of Administration

The *cannabis* oil extracts described herein are useful in the manufacture of a pharmaceutical composition or a medicament for treating a number of conditions including, but not limited to, cancer, headaches, vertigo, body aches, and glaucoma.

Pharmaceutical compositions or medicaments for use in the present invention can be formulated by standard techniques or methods well-known in the art of pharmacy using one or more physiologically acceptable carriers or excipients. Suitable pharmaceutical carriers are described herein and in, e.g., "Remington's Pharmaceutical Sciences" by E. W. Martin. *Cannabis* oil extracts can be formulated for administration by any suitable route, including, but not limited to, orally, topically, nasally, rectally, vaginally, pulmonary, parenterally (e.g., intravenously, subcutaneously, intramuscularly, etc.), and combinations thereof. In some embodiments, the *cannabis* oil is diluted in a liquid, e.g., a carrier oil. The most suitable route of administration in any given case will depend in part on the condition being treated as well as the response of the subject to the particular route of treatment.

In certain embodiments, *cannabis* oil compositions as described herein are administered via a vaporizer or like device as described, for example, in U.S. Pat. No. 8,915,254; U.S. Pat. Appl. Pub. No. 2014/0060552; U.S. Pat. No. 8,488,952; and U.S. Pat. Appl. Pub. No. 2015/0040926. Compositions for pulmonary administration also include, but are not limited to, dry powder compositions consisting of the powder of a *cannabis* oil described herein, and the powder of a suitable carrier and/or lubricant. The compositions for pulmonary administration can be inhaled from any suitable dry powder inhaler device known to a person skilled in the art. In certain instances, the compositions may be conveniently delivered in the form of an aerosol spray from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound(s) and a suitable powder base, for example, lactose or starch.

For oral administration, a pharmaceutical composition or a medicament can take the form of, e.g., a tablet or a capsule prepared by conventional means with a pharmaceutically acceptable excipient. Preferred are tablets and gelatin capsules comprising the active ingredient(s), together with (a) diluents or fillers, e.g., lactose, dextrose, sucrose, mannitol, maltodextrin, lecithin, agarose, xanthan gum, guar gum, sorbitol, cellulose (e.g., ethyl cellulose, microcrystalline cellulose), glycine, pectin, polyacrylates and/or calcium hydrogen phosphate, calcium sulfate, (b) lubricants, e.g., silica, anhydrous colloidal silica, talcum, stearic acid, its magnesium or calcium salt (e.g., magnesium stearate or calcium stearate), metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium or potassium salt, or effervescent mixtures; (e) wetting agents, e.g., sodium lauryl sulfate, and/or (f) absorbents, colorants, flavors and sweeteners. Tablets can be either uncoated or coated according to methods known in the art. The excipients described herein can also be used for preparation of buccal dosage forms and sublingual dosage forms (e.g., films and lozenges) as described, for example, in U.S. Pat. Nos. 5,981,552 and 8,475,832. Formulation in chewing gums as described, for example, in U.S. Pat. No. 8,722,022, is also contemplated.

Further preparations for oral administration can take the form of, for example, solutions, syrups, suspensions, and toothpastes. Liquid preparations for oral administration can be prepared by conventional means with pharmaceutically acceptable additives, for example, suspending agents, for example, sorbitol syrup, cellulose derivatives, or hydrogenated edible fats; emulsifying agents, for example, lecithin, xanthan gum, or *acacia*; non-aqueous vehicles, for example, almond oil, sesame oil, hemp seed oil, fish oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate.

Typical formulations for topical administration include creams, ointments, sprays, lotions, hydrocolloid dressings, and patches, as well as eye drops, ear drops, and deodorants. *Cannabis* oils can be administered via transdermal patches as described, for example, in U.S. Pat. Appl. Pub. No. 2015/0126595 and U.S. Pat. No. 8,449,908. Formulation for rectal or vaginal administration is also contemplated. The *cannabis* oils can be formulated, for example, as suppositories containing conventional suppository bases such as cocoa butter and other glycerides as described in U.S. Pat. Nos. 5,508,037 and 4,933,363. Compositions can contain other solidifying agents such as shea butter, beeswax, kokum butter, mango butter, ilipe butter, tamanu butter, carnauba wax, emulsifying wax, soy wax, castor wax, rice bran wax, and candelila wax. Compositions can further include clays (e.g., Bentonite, French green clays, Fuller's earth, Rhassoul clay, white kaolin clay) and salts (e.g., sea salt, Himalayan pink salt, and magnesium salts such as Epsom salt).

The compositions set forth herein can be formulated for parenteral administration by injection, for example by bolus injection or continuous infusion. Formulations for injection can be presented in unit dosage form, for example, in ampoules or in multi-dose containers, optionally with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure, buffers, and/or other ingredients. Alternatively, the compositions can be in powder form for reconstitution with a suitable vehicle, for example, a carrier oil, before use. In addition, the compositions may also contain other therapeutic agents or substances. The compositions are prepared according to conventional mixing, granulating or coating methods, respectively, and contain about 0.1 to 75%, preferably about 1 to 50%, of the *cannabis* oils.

In general, subjects receiving a *cannabis* oil composition orally are administered doses ranging from 1-2000 mg of *cannabis* oil. A small dose ranging from 1-20 mg will typically be administered orally when treatment of a condition such as cancer is initiated, and the dose will be increased (e.g., doubled) over a period of days or weeks until the maximum dose is reached. As a non-limiting example, a *cannabis* oil of the invention can be administered orally to a cancer patient at a dose of about 15 mg on days 1-4 of a treatment program; then at a dose of about 30 mg on days 5-8 of the treatment program; then at a dose of about 60 mg on days 9-12 of the treatment program; then at a dose of about 125 mg on days 13-16 of the treatment program; then at a dose of about 250 mg on days 17-20 of the treatment program; then at a dose of about 500 mg on days 21-24 of the treatment program; then at a dose of about 1000 mg on day 25 and subsequent days of the treatment program. Further doses (typically in the range of about 1-5 mg of cannabis oil per dose) can be administered via vaporizer throughout the treatment program.

Increasing doses can be administered using vegetarian gel capsule formulations as described herein. As a non-limiting example, gel capsules with a 15-mg dose of *cannabis* oil can be administered on the first 12 days of treatment (1, 2, or 4 capsules per day; capsule fill containing 9% (w/w) *cannabis* oil, 90.5% (w/w) hemp seed oil, 0.5% (w/w) vitamin E). Then, gel capsules with a 120-mg dose of *cannabis* oil can be administered on days 17-20 of treatment (1 or 2 capsules per day; capsule fill containing 33.3% (w/w) *cannabis* oil, 66.4% (w/w) hemp seed oil, 0.3% (w/w) vitamin E). Gel capsules with a 480-mg dose of *cannabis* oil can be administered on days 21-28 of treatment (1 or 2 capsules per day; capsule fill containing 66.7% (w/w) *cannabis* oil, 33.2% (w/w) hemp seed oil, 0.2% (w/w) vitamin E). From day 29 onward, two gel capsules with a 480-mg dose of *cannabis* oil can be administered (capsule fill containing 66.7% (w/w) *cannabis* oil, 33.2% (w/w) hemp seed oil, 0.2% (w/w) vitamin E). Further doses can be administered via vaporizer throughout the treatment program.

V. Blended *Cannabis* Oil Compositions

In another aspect, the invention provides *cannabis* oil compositions having a defined profile of cannabinoids and/or terpenes, which compositions are prepared by blending two or more of the *cannabis* oils described above. The cannabinoid profile refers to the number, identity, and quantity of cannabinoids in a *cannabis* oil; likewise, the terpene profile refers to the number, identity, and quantity of terpenes in the oil. Blending of two or more *cannabis* oils can provide compositions with properties and effects that are distinct from *cannabis* oils prepared from single *cannabis* strains. As a non-limiting example, breast cancer patients can benefit from administration of CBD and CBG. A composition containing a cannabinoid profile, designed to benefit a particular breast cancer patient population, can be obtained by blending complementary *cannabis* oils prepared from a *cannabis* strain rich in CBD (see, e.g., Gallily, et al. *Pharmacology & Pharmacy*, 2015; 6: 75-85) and a *cannabis* strain rich in CBG (see, e.g., Fournier, et al. *Planta Med* 1987; 53(3): 277-280). Furthermore, the aggregate properties of terpene mixtures can contribute meaningfully to the entourage effects of *cannabis*-based medicinal extracts in the treatment of conditions such as pain, inflammation, depression, anxiety, addiction, epilepsy, cancer (including, but not limited to, breast cancer and glioblastoma), fatty cysts, fungal infections, and bacterial infections. See, e.g., Russo, et al. *British Journal of Pharmacology*, 2011; 163: 1344-1364.

A blended *cannabis* oil composition of the invention can contain any ratio of cannabinoids and/or terpenes suitable for treating a given indication or otherwise eliciting a desired response in a subject to whom the composition is administered. For example, blended *cannabis* oil compositions for treatment of cancer will typically have THC:CBD weight ratios ranging from about 10:1 to about 1:10. The THC:CBD weight ratio can range from about 8:1 to about 1:8, or from about 6:1 to about 1:6, or from about 5:1 to about 1:5, or from about 4:1 to about 1:4, or from about 2:1 to about 2:1. In some embodiments, a blended *cannabis* oil composition for treatment of cancer will have a THC:CBD weight ratio of about 4:1.

Blended *cannabis* oil compositions for treatment of immune conditions (e.g., Lyme disease, autoimmune conditions) will typically have THC:CBD weight ratios ranging from about 30:1 to about 1:30. The THC:CBD weight ratio can range from about 25:1 to about 1:25, or from about 20:1 to about 1:20, or from about 16:1 to about 1:16, or from about 12:1 to about 1:12, or from about 8:1 to about 1:8, or from about 6:1 to about 1:6, or from about 5:1 to about 1:5, or from about 4:1 to about 1:4, or from about 2:1 to about 2:1. In some embodiments, a blended *cannabis* oil composition for treatment of an immune condition will have a THC:CBD weight ratio of about 4:1. In some embodiments, a blended *cannabis* oil composition for treatment of an immune condition will have a THC:CBD weight ratio of about 1:2. In some embodiments, a blended *cannabis* oil composition for treatment of an immune condition will have a THC:CBD weight ratio of about 1:20.

Blended *cannabis* oil compositions for treatment of conditions affecting the nervous system (e.g., neurodegenerative disorders, epilepsy, pain, sleep, anxiety, psychological disorders) will typically have THC:CBD weight ratios ranging from about 30:1 to about 1:30. The THC:CBD weight ratio can range from about 25:1 to about 1:25, or from about 20:1 to about 1:20, or from about 16:1 to about 1:16, or from about 12:1 to about 1:12, or from about 8:1 to about 1:8, or from about 6:1 to about 1:6, or from about 5:1 to about 1:5, or from about 4:1 to about 1:4, or from about 2:1 to about 2:1. In some embodiments, a blended *cannabis* oil composition for treatment of a condition affecting the nervous system will have a THC:CBD weight ratio of about 4:1. In some embodiments, a blended *cannabis* oil composition for treatment of a condition affecting the nervous system will have a THC:CBD weight ratio of about 1:1. In some embodiments, a blended *cannabis* oil composition for treatment of a condition affecting the nervous system will have a THC:CBD weight ratio of about 1:20.

A blended *cannabis* oil composition of the invention can contain any ratio of cannabinoids and/or terpenes suitable for treating a given indication or otherwise eliciting a desired response in a subject to whom the composition is administered. For example, blended *cannabis* oil compositions containing predominantly neutral cannabinoids will typically have THC:THCA:CBD:CBDA weight (or molar) ratios ranging from about 20:0.01:1:0.01 to about 1:0.01:20:0.01. Blended *cannabis* oil compositions containing predominantly acidic cannabinoids will typically have THC:THCA:CBD:CBDA weight (or molar) ratios ranging from about 0.01:20:0.01:1 to about 0.01:1:0.01:20. The THC:THCA:CBD:CBDA weight ratio can range from about 8:1:1:0.1 to about 1:0.1:8:1; or from about 6:1:1:0.1 to about 1:0.1:6:1; or from about 4:1:1:0.1 to about 1:0.1:4:1; or from about 2:1:1:0.1 to about 1:0.1:2:1; or from about 1:10:1:10 to about 1:10:0.1:1; or from about 1:4:0.1:1 to about 0.1:1:1:4. In certain embodiments, the blended *cannabis* oil composition has a THC:THCA:CBD:CBDA weight ratio of about 4:1:1:0.1.

Blended oil compositions having a high amount of THC (e.g., a composition with a THC:CBD ratio around 20:1) can be particularly useful for treating severe pain and inflammation, as well as for inducing sleep. Blended oil compositions with a THC:CBD ratio around 4:1 can also have sleep-inducing and anti-inflammatory effects. The anti-inflammatory effect has been observed to increase cumulatively over time in certain subjects.

Blended oil compositions with high levels of THC can induce or impair cognition in certain subjects, particularly in the absence of gradual attenuation of the subject to the neurological effects of the compositions. Blended oil compositions with a THC:CBD ratio around 2:1 can therefore be used to elicit the strong effects of high-THC compositions while preventing anxiety or other side effects due to the softening effect of CBD. CBD can also enhance the effects of THC in a synergistic fashion. In certain oncology patients and seizure patients, blended oil compositions with a THC:CBD ratio around 1:1 can provide symptom relief with less cognitive alteration than blended oil compositions with a THC:CBD ratio around 4:1.

Blended oil compositions with a THC:CBD ratio around 1:2 can be useful for treating patients who require THC for effective symptom control, but cannot tolerate or do not want to experience mood-altering effects (e.g., euphoria or anxiety) associated with high-THC compositions. Depending on the particular subject, a THC:CBD ratio around 1:2 can be sleep-inducing, calming, mood-elevating, and mildly to moderately appetite-inducing. Blended oil compositions with a THC:CBD ratio around 1:4 can be used to incorporate THC as an anti-inflammatory agent that contributes synergistically to alleviation of symptoms by CBD.

Blended oil compositions having a high amount of CBD (e.g., a composition with a THC:CBD ratio around 1:20) can be useful for treating inflammation as well as chronic pain including, but not limited to, back pain, fibromyalgia, and migraine. In certain instances, high-CBD blended oil compositions can be used to supplement or replace NSAIDs or other over-the-counter pain medications and anti-inflammatory medications. High-CBD compositions can also be used to reduce anxiety, enhance serotonin, and elicit focusing and/or calming effects. The anti-spasticity properties of high-CBD blended oil compositions also makes them useful for treating Parkinson's disease, Huntington's disease, multiple sclerosis, and other neurodegenerative diseases.

In some embodiments, the blended *cannabis* oil composition includes a CBD component derived from the AC/DC *cannabis* strain and a THC component derived from a *Cannabis sativa* strain. In some embodiments, the blended *cannabis* oil composition includes an oil prepared from the AC/DC *cannabis* strain, as describe herein, and an equal part (i.e., 1:1 w/w) of oil prepared from a *Cannabis sativa* strain (e.g., Infinite Euphoria). In some such embodiments, the blended *cannabis* oil composition further includes vitamin E. In some such embodiments, the blended *cannabis* oil composition further includes vitamin E and one or more essential oils selected from bergamot essential oil, blood orange essential oil, sweet orange essential oil, lemon essential oil, vanilla essential oil, neroli essential oil, lemongrass essential oil, lavender essential oil, peppermint essential oil, and spearmint essential oil. In some such embodiments, the blended *cannabis* oil composition further includes vitamin E and one or more essential oils selected from bergamot essential oil, blood orange essential oil, neroli essential oil, peppermint essential oil, and spearmint essential oil.

In some embodiments, the blended *cannabis* oil composition includes a CBD component derived from the Medihaze *cannabis* strain and a THC component derived from a *Cannabis indica* strain. In some embodiments, the blended *cannabis* oil composition includes an oil prepared from the Medihaze *cannabis* strain and an equal part (i.e., 1:1 w/w) of oil prepared from a *Cannabis indica* strain (e.g., Afghan Goo, Prize Kush, or Blueberry). In some such embodiments, the blended *cannabis* oil composition further includes vitamin E. In some such embodiments, the blended *cannabis* oil composition further includes vitamin E and one or more essential oils selected from lavender essential oil and lemongrass essential oil.

The blended *cannabis* compositions can further contain additional *cannabis* oil preparations. In some embodiments, for example, the invention provides a composition containing a first *cannabis* oil preparation having a first cannabinoid profile, a second *cannabis* oil preparation having a second cannabinoid profile, and a third *cannabis* oil preparation having a third cannabinoid profile.

In certain embodiments, the invention provides a composition containing a first *cannabis* oil preparation having a first cannabinoid profile, a second *cannabis* oil preparation having a second cannabinoid profile, a third *cannabis* oil preparation having a third cannabinoid profile, and a fourth *cannabis* oil preparation having a fourth cannabinoid profile. In some such embodiments, at least 50% of the total THC in the composition is present in the combined cannabinoid profile of the first *cannabis* oil preparation, the second *cannabis* oil preparation, and the third *cannabis* oil preparation; and at least 50% of the total CBD in the composition is present in the fourth cannabinoid profile. In some such embodiments, at least 75% of the total THC in the composition is present in the combined cannabinoid profile of the first *cannabis* oil preparation, the second *cannabis* oil preparation, and the third *cannabis* oil preparation; and at least 75% of the total CBD in the composition is present in the fourth cannabinoid profile.

In some embodiments, the invention provides a composition containing four *cannabis* oil preparations wherein the first *cannabis* oil preparation is prepared from a *Cannabis indica* strain, the second *cannabis* oil preparation is prepared from a *Cannabis sativa* strain, the third *cannabis* oil preparation is prepared from the Blueberry *cannabis* strain, and the fourth *cannabis* oil preparation is prepared from the AC/DC *cannabis* strain. In some such embodiments, the ratio of the first, second, third, and fourth *cannabis* oil preparations is about 55:10:10:25 by weight. In some such embodiments, the composition further contains vitamin E.

In some such embodiments, the ratio of the first, second, third, and fourth *cannabis* oil preparations is about 60:10:10:20 by weight. In some such embodiments, the THC:CBD ratio is around 4:1.

In some such embodiments, the ratio of the first, second, third, and fourth *cannabis* oil preparations is about 45:10:10:35 by weight. In some such embodiments, the THC:CBD ratio is around 2:1.

In some such embodiments, the ratio of the first, second, third, and fourth *cannabis* oil preparations is about 30:10:10:50 by weight. In some such embodiments, the THC:CBD ratio is around 1:1.

In some such embodiments, the ratio of the first, second, third, and fourth *cannabis* oil preparations is about 10:10:10:70 by weight. In some such embodiments, the THC:CBD ratio is around 1:2.

In some such embodiments, the ratio of the first, second, third, and fourth *cannabis* oil preparations is about 5:5:5:85 by weight. In some such embodiments, the THC:CBD ratio is around 1:4.

In some embodiments, the first *cannabis* oil composition is prepared from a *Cannabis indica* strain selected from the group consisting of Gorilla Glue; Blueberry Smooth, Black Lime Reserve, Purple Trainwreck, Dream Kush, Blue Diesel, Purple OG, Skywalker OG, Dream Kush, Nepalese Kush, Purple Hashplant, Bubble Gum, MK Ultra, Prize Kush, Chocolate Kush, Afgoo, OG Kush, Afghan Kush, Blueberry Kush, Blackberry Kush, Bubba Kush, Northern lights, Granddaddy purple, OG-Kush, and Girl Scout Cookies.

In some embodiments, the first *cannabis* oil composition prepared from the *Cannabis indica* strain contains THC in an amount ranging from about 45% to about 90% (e.g., from 49.7% to 86.35%) and CBD in an amount ranging up to about 5.0% (e.g., from 0.0% to 3.57%).

In some embodiments, the first *cannabis* oil composition further contains linalool in an amount ranging from about 0.001% to about 0.005% (e.g., from 0.001% to 0.36%); and/or β-caryophyllene in an amount ranging from about 0.001% to about 2.5% (e.g., from 0.002% to 1.22%); and/or caryophyllene oxide in an amount ranging from about 0.001% to about 1.0% (e.g., about 0.002% to 0.66%); and/or α-humulene in an amount ranging from about 0.01% to about 1% (e.g., from 0.02% to 0.49%); and/or α-bisabolol in an amount ranging from about 0.005% to about 0.5% (e.g., from 0.008% to 0.43%); and/or α-terpineol in an amount ranging from about 0.05% to about 0.5% (e.g., from 0.08% to 0.15%); and/or endo-fenchyl alcohol in an amount ranging from about 0.04% to about 0.4% (e.g., from 0.06% to 0.15%); and/or terpinolene in an amount ranging from about 0.001% to about 0.025% (e.g., from 0.001% to 0.01%); and/or guaiol in an amount ranging from about 0.001% to about 1.0% (e.g., from 0.007% to 0.33%); and/or cis-ocimene in an amount ranging from about 0.001% to about 0.05% (e.g., from 0.005% to 0.014%); and/or 1-pinene in an amount ranging from about 0.005% to about 0.1% (e.g., from 0.021% to 0.0$^{49}$%); and/or J-myrcene in an amount ranging from about 0.001% to about 0.01% (e.g., from 0.003% to 0.006%); and/or α-terpinene in an amount ranging from about 0.001% to about 0.01% (e.g., from 0.001% to 0.002%); and/or α-pinene in an amount ranging from about 0.001% to about 0.01% (e.g., from 0.002% to 0.007%); and/or 3-carene in an amount ranging up to about 0.005% (e.g., from 0% to 0.003%); and/or β-eudesmol in an amount ranging from about 0.005% to about 0.250% (e.g., from 0.09% to 0.16%); and/or α-eudesmol in an amount ranging from about 0.050% to about 0.500% (e.g., from 0.12% to 0.32%); and/or γ-eudesmol in an amount ranging from about 0.050% to about 0.500% (e.g., from 0.07% to 0.29%); and/or cis-neridol in an amount ranging from about 0.1% to about 1.0% (e.g., from 0.15% to 0.58%); and/or trans-neridol in an amount ranging from about 0.001% to about 0.100% (e.g., from 0.002% to 0.06%); and/or isopulegol in an amount ranging from about 0.01% to about 0.10% (e.g., from 0.016% to 0.054%); and/or cymene in an amount ranging from about 0.001% to about 0.050% (e.g., from 0.004% to 0.025%).

In some embodiments, the second *cannabis* oil composition is prepared from a *Cannabis sativa* strain selected from the group consisting of Sour Boggle, Blue Dream, Jilly Bean, Infinite Euphoria, Dream Queen, Sour Diesel, and Green Crack.

In some embodiments, the second *cannabis* oil composition prepared from the *Cannabis sativa* strain contains THC in an amount ranging from about 45% to about 85% (e.g., from 49.6% to 81.4%) and CBD in an amount ranging up to about 2.5% (e.g., from 0.0% to 1.9%).

In some embodiments, the second *cannabis* oil composition further contains linalool in an amount ranging from about 0.001% to about 1.0% (e.g., from 0.001% to 0.93%); and/or β-caryophyllene in an amount ranging from about 0.001% to about 2.0% (e.g., from 0.002% to 0.96%); and/or caryophyllene oxide in an amount ranging from about 0.001% to about 0.050% (e.g., from 0.002% to 0.42%); and/or α-humulene in an amount ranging from about 0.001% to about 1.0% (e.g., from 0.001% to 0.49%); and/or α-bisabolol in an amount ranging from about 0.001% to about 2.5% (e.g., from 0.005% to 1.17%); and/or α-terpineol in an amount ranging up to about 0.1% (e.g., from 0.0% to 0.07%); and/or endo-fenchyl alcohol in an amount ranging up to about 0.2% (e.g., from 0.0% to 0.14%); and/or terpinolene in an amount ranging up to about 0.05% (e.g., from 0.0% to 0.002%%); and/or isobomeol in an amount ranging from about 0.05% to about 0.50% (e.g., from 0.09% to 0.15%); and/or guaiol in an amount ranging from about 0.001% to about 0.500% (e.g., from 0.004% to 0.29%); and/or geraniol in an amount ranging up to about 0.5% (e.g., from 0.0% to 0.003%); and/or γ-terpinene in an amount ranging from about 0.001% to about 0.005% (e.g., from 0.001% to 0.002%); and/or cis-ocimene in an amount ranging from about 0.001% to about 0.050% (e.g., from 0.002% to 0.013%); and/or camphene in an amount ranging up to about 0.002% (e.g., from 0.0% to 0.001%); and/or β-pinene in an amount ranging from about 0.001% to about 0.250% (e.g., from 0.001% to 0.157%); and/or j3-myrcene in an amount ranging from about 0.001% to about 0.500% (e.g., from 0.002% to 0.19%); and/or α-terpinene in an amount ranging from about 0.001% to about 0.050% (e.g., from 0.001% to 0.002%); and/or α-pinene in an amount ranging from about 0.001% to about 0.100% (e.g., from 0.002% to 0.023%); and/or 3-carene in an amount ranging from about 0.001% to about 0.100% (e.g., from 0.003% to 0.016%); and/or β-eudesmol in an amount ranging up to about 0.250% (e.g., from 0.0% to 0.18%); and/or α-eudesmol in an amount ranging from about 0.05% to about 1.0% (e.g., from 0.09% to 0.53%); and/or γ-eudesmol in an amount ranging from about 0.1% to about 0.5% (e.g., from 0.14% to 0.24%); and/or valencene in an amount ranging from about 0.1% to about 0.5% (e.g., from 0.1% to 0.16%); and/or cis-neridol in an amount ranging from about 0.005% to about 1.0% (e.g., from 0.01% to 0.56%); and/or trans-neridol in an amount ranging from about 0.001% to about 0.500% (e.g., from 0.003% to 0.22%); and/or isopulegol in an amount ranging from about 0.001% to about 0.100% (e.g., from 0.005% to 0.048%); and/or cymene in an amount ranging from about 0.001% to about 0.050% (e.g., from 0.003% to 0.036%).

In some embodiments, the third *cannabis* oil composition prepared from the Blueberry *cannabis* strain contains THC content in an amount ranging from about 50% to about 85% (e.g., from 530.98% to 81.4%) and CBD in an amount ranging from about 0.1% to about 10% (e.g., from 0.14% to 60.63%).

In some embodiments, the third *cannabis* oil composition further contains linalool in an amount ranging from about 0.001% to about 0.200% (e.g., from 0.001% to 0.15%); and/or β-caryophyllene in an amount ranging from about 0.001% to about 1.0% (e.g., from 0.002% to 0.77%); and/or caryophyllene oxide in an amount ranging from about 0.001% to about 0.200% (e.g., from 0.002% to 0.16%); and/or α-humulene in an amount ranging from about 0.001% to about 0.75% (e.g., from 0.001% to 0.49%); and/or α-bisabolol in an amount ranging from about 0.005% to about 0.5% (e.g., from 0.011% to 0.25%); and/or α-terpineol in an amount ranging up to about 0.1% (e.g., from 0.0% to 0.07%); and/or terpinolene in an amount ranging up to about 0.001% (e.g., from 0.0% to 0.001%); and/or isoborneol in an amount ranging up to about 0.2% (e.g., from 0.0% to 0.15%); and/or guaiol in an amount ranging up to about 0.01% (e.g., from 0.0% to 0.009%); and/or geraniol in an amount ranging up to about 0.005% (e.g., from 0.0% to 0.003%); and/or cis-ocimene in an amount ranging from about 0.001% to about 0.01% (e.g., from 0.003% to 0.007%); and/or camphene in an amount ranging up to about 0.01% (e.g., from 0.0% to 0.009%); and/or β-pinene in an amount ranging from about 0.001% to about 0.1% (e.g., from 0.001 0.065%); and/or β-myrcene in an amount ranging from about 0.001% to about 0.01% (e.g., from 0.001

0.009%); and/or α-terpinene in an amount ranging up to about 0.005% (e.g., from 0.0% to 0.001%); and/or α-pinene in an amount ranging from about 0.001% to about 0.01% (e.g., from 0.002% to 0.007%); and/or 3-carene in an amount ranging from about 0.001% to about 0.01% (e.g., from 0.003% to 0.008%); and/or α-eudesmol in an amount ranging up to about 0.1% (e.g., from 0.0% to 0.09%); and/or cis-neridol in an amount ranging from about 0.01% to about 0.5% (e.g., from 0.043% to 0.19%); and/or trans-neridol in an amount ranging from about 0.001% to about 0.05% (e.g., from 0.003% to 0.012%); and/or isopulegol in an amount ranging from about 0.001% to about 0.1% (e.g., from 0.005% to 0.048%); and/or cymene in an amount ranging from about 0.001% to about 0.2% (e.g., from 0.003% to 0.173%).

In some embodiments, the Blueberry strain can be replaced with a strain selected from the group consisting of Blackberry Kush, Bubba Kush, Northern lights, Granddaddy purple, OG-Kush, Sour Diesel, Blue Dream, Green Crack, and Girl Scout Cookies for preparation of the third *cannabis* oil composition.

In some embodiments, the fourth *cannabis* oil composition prepared from the ACDC *cannabis* strain contains THC in an amount ranging from about 1% to about 40% (e.g., from 20.4-370.60%) and CBD in an amount ranging from about 25% to about 75% (e.g., from 29.10-72.60%).

In some embodiments, the fourth *cannabis* oil composition further contains linalool in an amount ranging from about 0.01% to about 0.25% (e.g., from 0.042% to 0.19%); and/or β-caryophyllene in an amount ranging from about 0.05% to about 1.0% (e.g., from 0.086% to 0.66%); and/or caryophyllene oxide in an amount ranging from about 0.001% to about 0.5% (e.g., from 0.002% to 0.42%); and/or α-humulene in an amount ranging from about 0.01% to about 0.5% (e.g., from 0.028% to 0.38%); and/or α-bisabolol in an amount ranging from about 0.005% to about 1.0% (e.g., from 0.011% to 0.99%); and/or α-terpineol in an amount ranging from about 0.05% to about 0.2% (e.g., from 0.08% to 0.1%); and/or endo-fenchyl alcohol in an amount ranging from about 0.05% to about 0.2% (e.g., from 0.08% to 0.1%); and/or isobomeol in an amount ranging from about 0.05% to about 0.5% (e.g., from 0.08% to 0.2%); and/or guaiol in an amount ranging from about 0.005% to about 0.5% (e.g., from 0.01% to 0.28%); and/or geraniol in an amount ranging up to about 0.2% (e.g., from 0.0% to 0.102%); and/or β-pinene in an amount ranging from about 0.005% to about 0.05% (e.g., from 0.015% to 0.028%); and/or β-myrcene in an amount ranging from about 0.001% to about 0.1% (e.g., from 0.002% to 0.06%); and/or α-terpinene in an amount ranging up to about 0.01% (e.g., from 0.0% to 0.005%); and/or α-pinene in an amount ranging from about 0.001% to about 0.05% (e.g., from 0.002% to 0.02%); and/or β-eudesmol in an amount ranging from about 0.01% to about 0.2% (e.g., from 0.06% to 0.12%); and/or α-eudesmol in an amount ranging from about 0.05% to about 0.5% (e.g., from 0.08% to 0.43%); and/or valencene in an amount ranging from about 0.05% to about 0.2% (e.g., from 0.08% to 0.18%); and/or cis-neridol in an amount ranging from about 0.01% to about 1.0% (e.g., from 0.027% to 0.63%); and/or trans-neridol in an amount ranging from about 0.01% to about 0.5% (e.g., from 0.015% to 0.22%); and/or isopulegol in an amount ranging from about 0.01% to about 0.1% (e.g., from 0.012% to 0.075%); and/or cymene in an amount ranging from about 0.01% to about 0.05% (e.g., from 0.011% to 0.025%).

In some embodiments, the ACDC strain can be replaced with a strain selected from the group consisting of Harle Tsu, Medi-Haze, Charlotte's Web, Sour Tsunami, Abacus, Ringo's Gift, Cannatonic, Harlequin, and Buddha Passion for preparation of the fourth *cannabis* oil composition.

The blended oil compositions can be diluted with sunflower oil or another suitable carrier oil, as described above, to provide a diluted *cannabis* oil composition. For example, a diluted *cannabis* oil composition can contain total cannabinoids in amounts ranging from about 500 mg to about 20,000 mg in volumes ranging from about 0.5 fluid ounces (i.e., 15 mL) to about 2.5 fluid ounces (i.e., 75 mL). A diluted *cannabis* oil composition can contain the total cannabinoids in a concentration of around 10 mg/mL, or 20 mg/mL, or 100 mg/mL, or 300 mg/mL. The oil concentrate can be further diluted with sunflower oil or another suitable carrier oil by a factor of 2, 5, 10, 25, or higher to aid oral administration of a desired dose.

When added, a carrier oil will typically be present in a diluted *cannabis* oil composition in an amount ranging from about 1% (w/w) to about 95% (w/w). A carrier oil can be present, for example, in an amount ranging from about 5% (w/w) to about 10% (w/w), or from about 10% (w/w) to about 15% (w/w), or from about 15% (w/w) to about 20% (w/w), or from about 20% (w/w) to about 25% (w/w), or from about 25% (w/w) to about 30% (w/w), or from about 30% (w/w) to about 35% (w/w), or from about 35% (w/w) to about 40% (w/w), or from about 40% (w/w) to about 45% (w/w), or from about 45% (w/w) to about 50% (w/w), or from about 50% (w/w) to about 55% (w/w), or from about 55% (w/w) to about 60% (w/w), or from about 60% (w/w) to about 65% (w/w), or from about 65% (w/w) to about 70% (w/w), or from about 70% (w/w) to about 75% (w/w), or from about 75% (w/w) to about 80% (w/w), or from about 80% (w/w) to about 85% (w/w), or from about 85% (w/w) to about 90% (w/w), or from about 90% (w/w) to about 95% (w/w). A carrier oil can be present in an amount ranging from about 5% (w/w) to about 95% (w/w), or from about 10% (w/w) to about 90% (w/w), or from about 15% (w/w) to about 85% (w/w), or from about 20% (w/w) to about 80% (w/w), or from about 25% (w/w) to about 75% (w/w), or from about 30% (w/w) to about 70% (w/w), or from about 35% (w/w) to about 65% (w/w), or from about 40% (w/w) to about 60% (w/w), or from about 45% (w/w) to about 55% (w/w).

VI. Examples

The following examples are offered to illustrate, but not to limit, the claimed invention.

Example 1. Compositions Containing *Cannabis* Oil and Vitamin E

Figure 2:
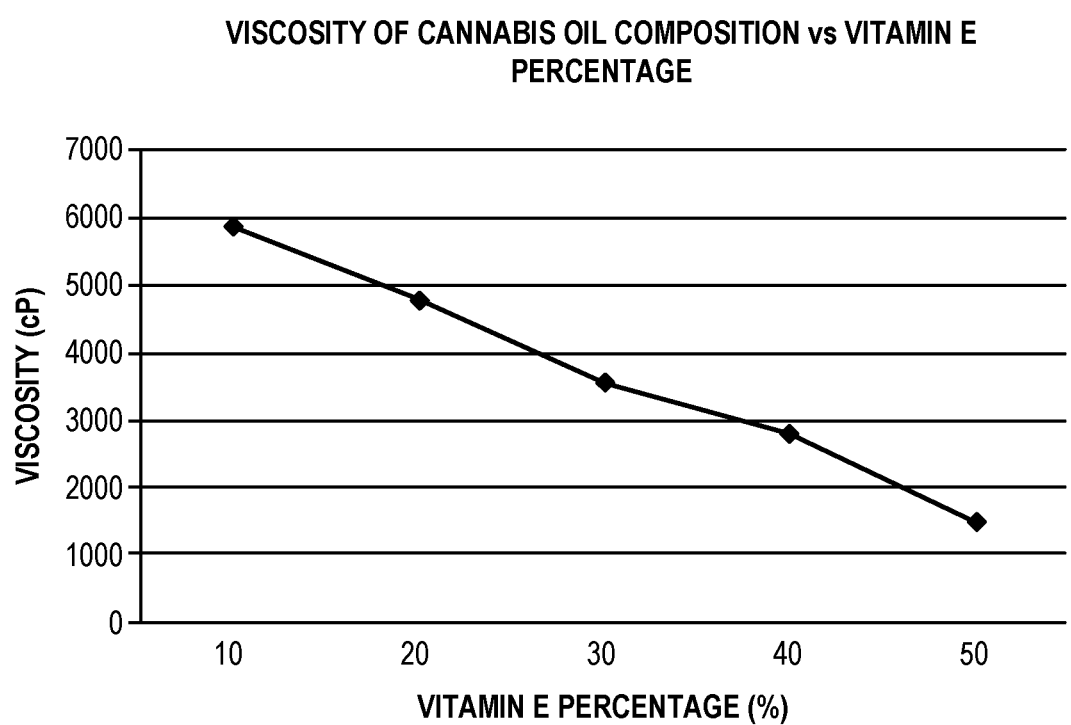
FIG. 2 shows a graph depicting the viscosities of *cannabis* oil compositions as a function of vitamin E percentages in the *cannabis* oil compositions.

Reference is now made to FIG. 2, which is a graph depicting the viscosities of *cannabis* oil compositions as a function of vitamin E percentage in the *cannabis* oil compositions, according to one or more embodiments. As indicated in FIG. 2, the viscosities of the *cannabis* oil compositions can be measured in centipoise (cP) and the % w/w of vitamin E 121 can be based on the total weight of the *cannabis* oil composition.

FIG. 2 depicts the results of viscosity experiments conducted by mixing vitamin E 121 of various quantities with the extract 119. In these experiments, the total weight of the *cannabis* oil composition was set at approximately 25.00 grams. As indicated in Table 2 below, the % w/w of the vitamin E 121 ranged from 10% w/w to 50% w/w:

TABLE 2

Amounts of Vitamin E and Extract in *Cannabis* Oil Composition Used in Viscosity Experiments

| Vitamin E % w/w | Vitamin E Amount (grams) | Extract Amount (grams) | Total *cannabis* Oil Composition (grams) |
|---|---|---|---|
| 10 | 2.50 | 22.50 | 25.00 |
| 20 | 5.00 | 20.00 | 25.00 |
| 30 | 7.50 | 17.50 | 25.00 |
| 40 | 10.00 | 15.00 | 25.00 |
| 50 | 12.50 | 12.50 | 25.00 |

The purpose of the experiments was to determine a preferred quantity of vitamin E 121 that will reduce the viscosity of the *cannabis* oil composition yet preserve the gustatory or aromatic qualities of the extract 119. Moreover, the preferred quantity of vitamin E 121 should also provide beneficial reductions in viscosity while also not displacing too much of the cannabinoids 107 in the *cannabis* oil composition.

As indicated above, *cannabis* oil is often highly viscous, making it difficult to work with and load into new delivery devices such as vaporizers, E-cigarettes, or pens. As will be discussed in more detail below, one unexpected benefit of mixing the vitamin E 121 with the extract 119 is reducing the viscosity of the *cannabis* oil composition and making the *cannabis* oil composition conducive for loading or packing into modern day vaporizers, E-cigarettes, or pens.

The viscosity experiments were conducted using a viscometer. For example, the viscometer can be a falling ball viscometer. More specifically, the falling ball viscometer can be a PDVdi-120 Portable Falling Ball Viscometer from Stony Brook Scientific™. Each of the *cannabis* oil compositions were first heated on a hotplate at approximately 95° C. and mixed with a glass stirring rod. Aliquots of the *cannabis* oil compositions were then transferred into the falling ball viscometer and falling times in seconds were measured at 45.8° C. Results of the viscosity experiments are presented in Table 3 below:

TABLE 3

Falling Times as a Functions of Vitamin E % w/w

| Vitamin E % w/w | Falling Times (s) | Viscosity (cP), calculated using Falling Times |
|---|---|---|
| 10 | 333.1 | 5868.73 |
| 20 | 272.1 | 4794.00 |
| 30 | 200.9 | 3539.56 |
| 40 | 159.3 | 2806.63 |
| 50 | 83.7 | 1474.67 |

The viscosity of each *cannabis* oil composition was calculated using the applicable falling time in Table 3 above and Equation 1 below:

$$\text{Viscosity (cP)} = 9.1463 \text{ cm}^2\text{s}^{-2} * (\text{Needle Density} - \text{Approximate Fluid Density}) * \text{Falling Time} \quad \text{Equation 1:}$$

In the above Equation 1, Needle Density=2.9263 g*cm$^{-3}$ and Approximate Fluid Density=1.0000 g*cm$^{-3}$. As shown in FIG. 2 and Table 3 above, an increase in the % w/w of vitamin E 121 by 10% corresponds to an approximate 1000 cP decrease in the viscosity of the *cannabis* oil composition.

In one preferred embodiment, the *cannabis* oil composition has a viscosity of less than 3500 cP. In another preferred embodiment, the *cannabis* oil composition has a viscosity of less than 3000 cP. In yet another preferred embodiment, the *cannabis* oil composition has a viscosity of less than 2000 cP.

All *cannabis* oil compositions were subjected to organoleptic analysis after addition of vitamin E, including tests designed to ascertain the taste, smell, and ease of inhaling the *cannabis* oil compositions. Based on this organoleptic analysis, it was discovered that vitamin E concentrations around 30% w/w provide useful viscosity levels while preserving the gustatory or aromatic qualities of the extract 119.

Figure 3:
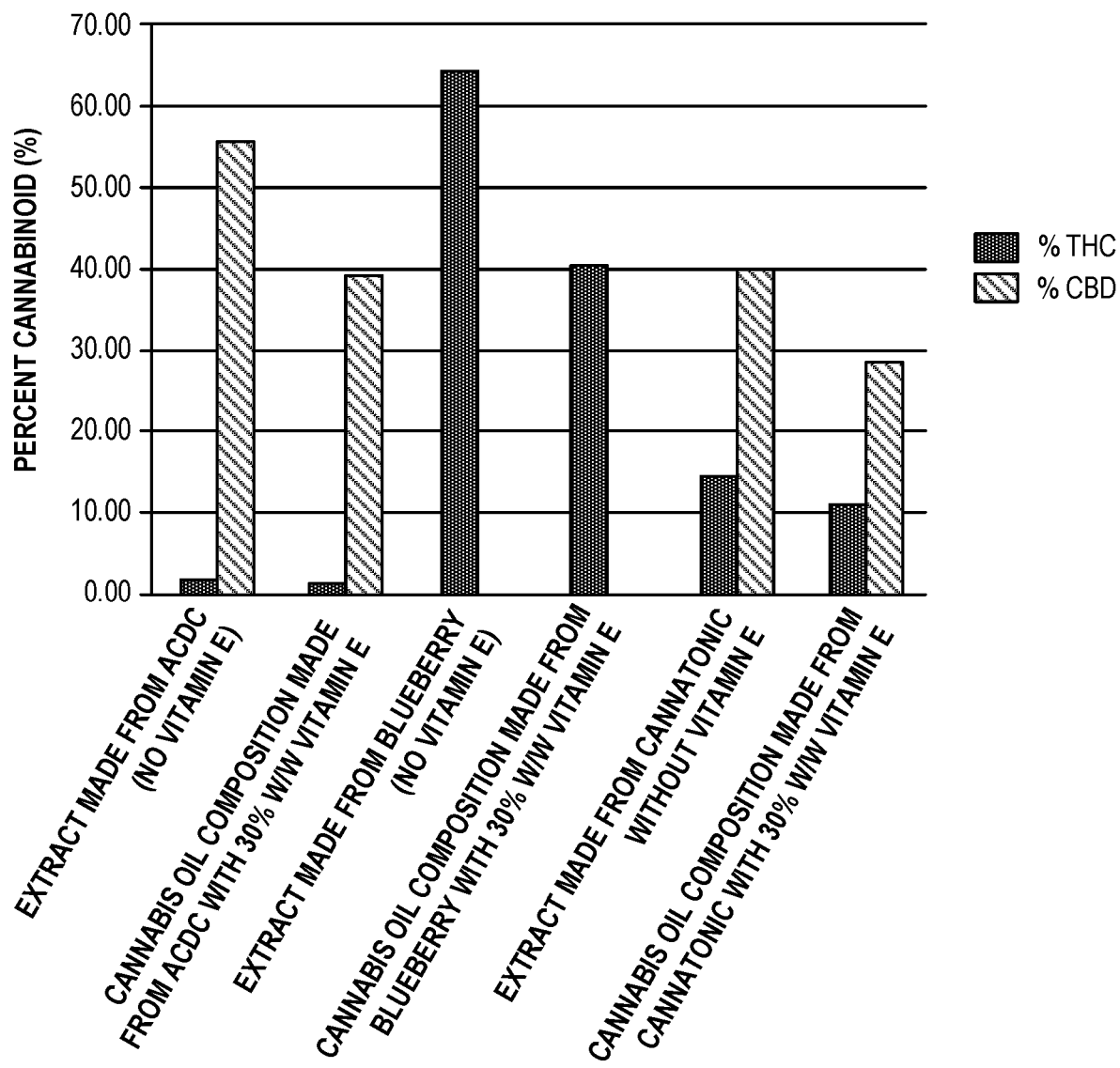
FIG. 3 is a graph depicting THC and CBD percentages in *cannabis* oil compositions made from various strains of *cannabis* plant material.
Figure 4A:
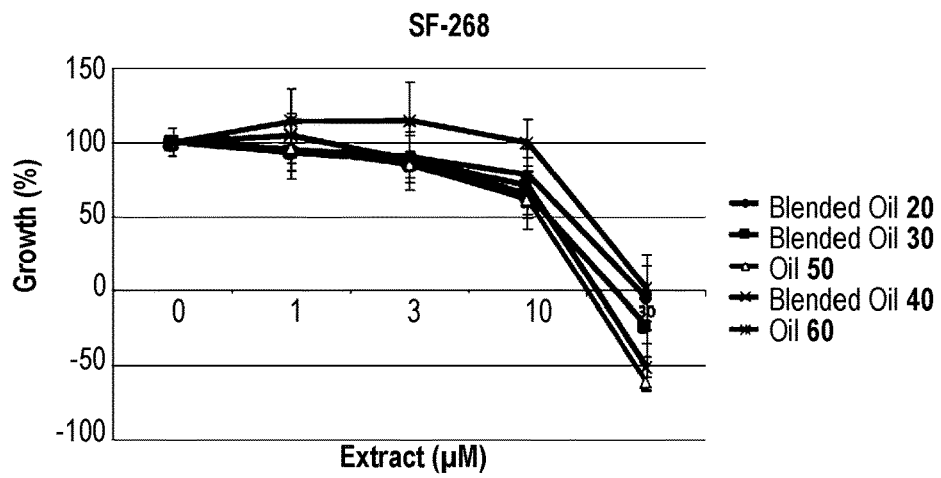
FIG. 4A shows the growth of SF-268 brain cancer cells in the presence of blended *cannabis* oil compositions and single-strain *cannabis* oil compositions.
Figure 4B:
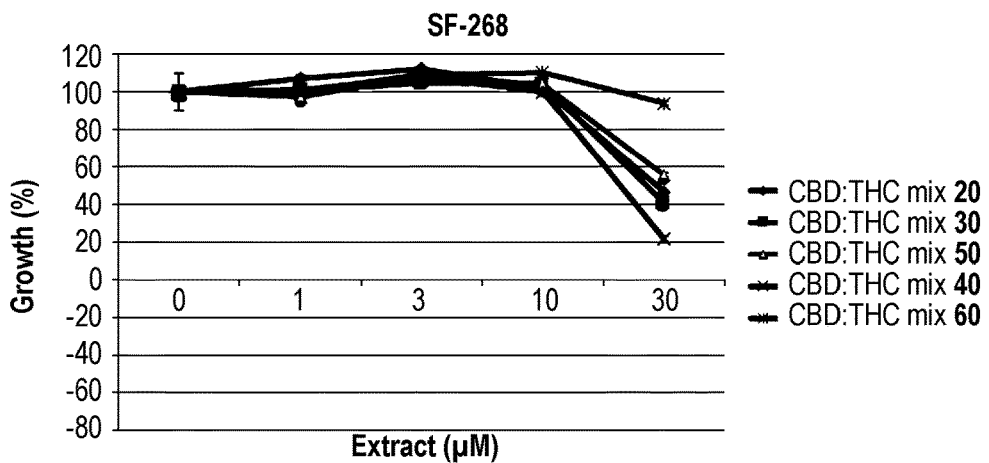
FIG. 4B shows the growth of SF-268 brain cancer cells in the presence THC and CBD at concentrations equal to the concentration in blended *cannabis* oil compositions and single-strain *cannabis* oil compositions.
Figure 4C:
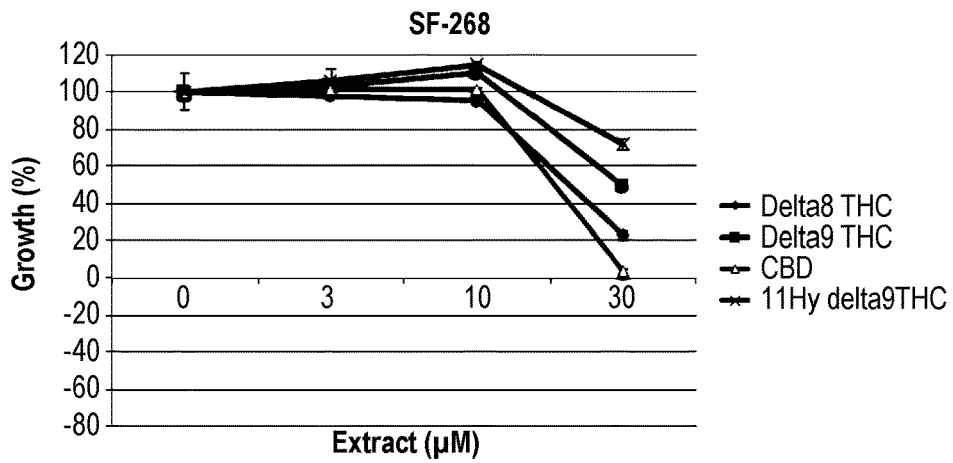
FIG. 4C shows the growth of SF-268 brain cancer cells in the presence of isolated cannabinoids.
Figure 5A:
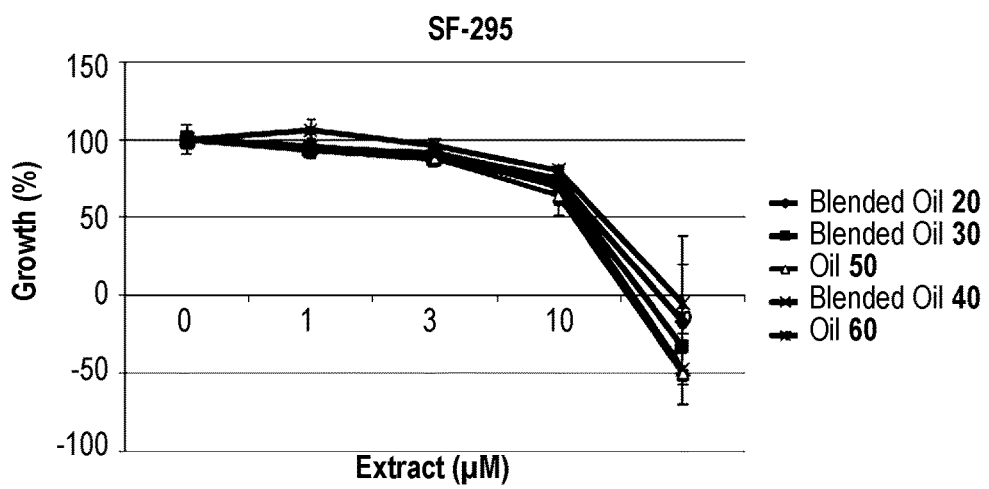
FIG. 5A shows the growth of SF-295 brain cancer cells in the presence of blended *cannabis* oil compositions and single-strain *cannabis* oil compositions.
Figure 5B:
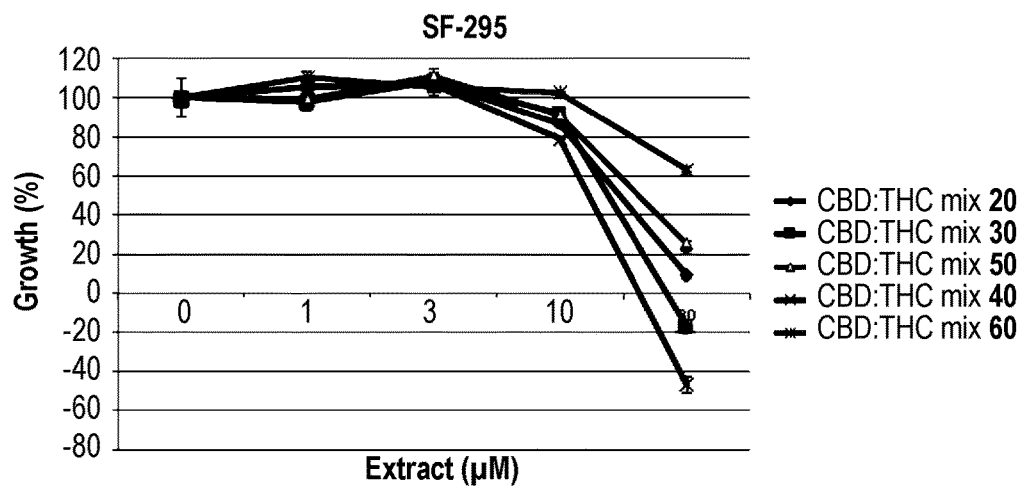
FIG. 5B shows the growth of SF-295 brain cancer cells in the presence THC and CBD at concentrations equal to the concentration in blended *cannabis* oil compositions and single-strain *cannabis* oil compositions.
Figure 5C:
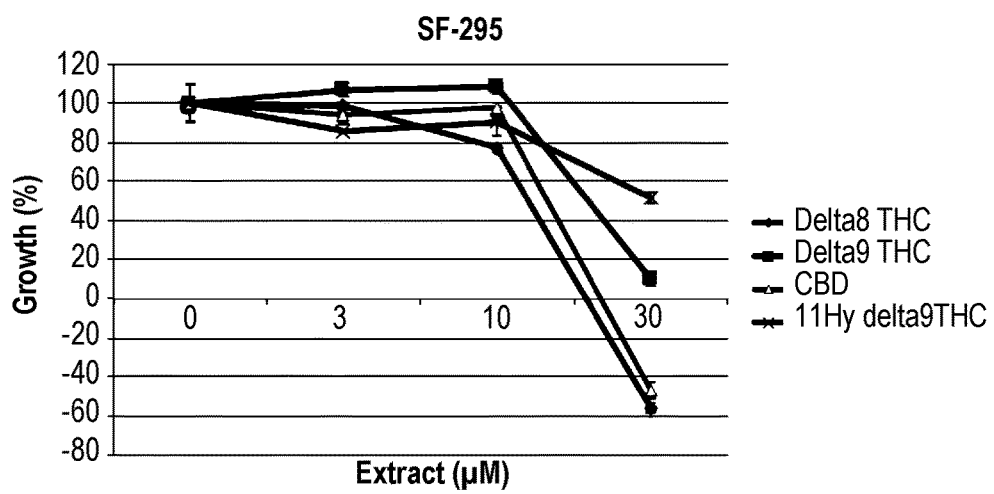
FIG. 5C shows the growth of SF-295 brain cancer cells in the presence of isolated cannabinoids.
Figure 6A:
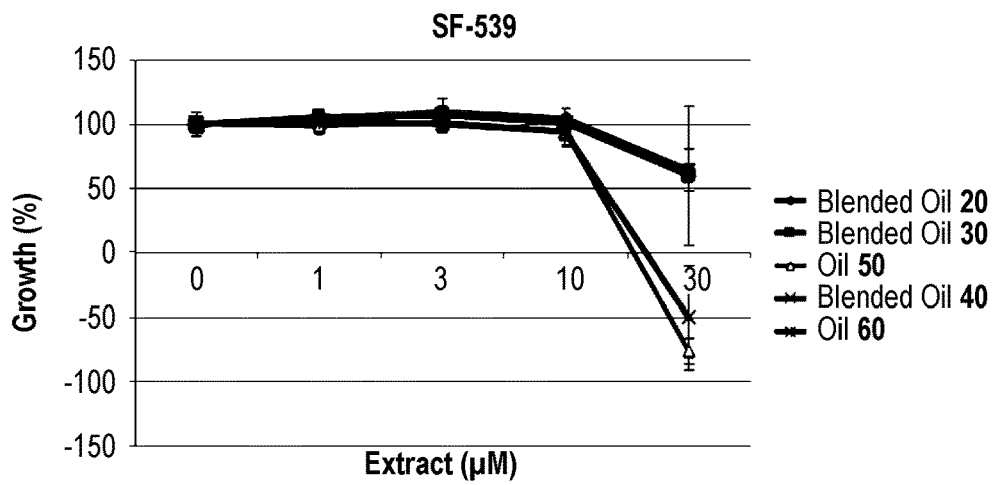
FIG. 6A shows the growth of SF-539 brain cancer cells in the presence of blended *cannabis* oil compositions and single-strain *cannabis* oil compositions.
Figure 6B:
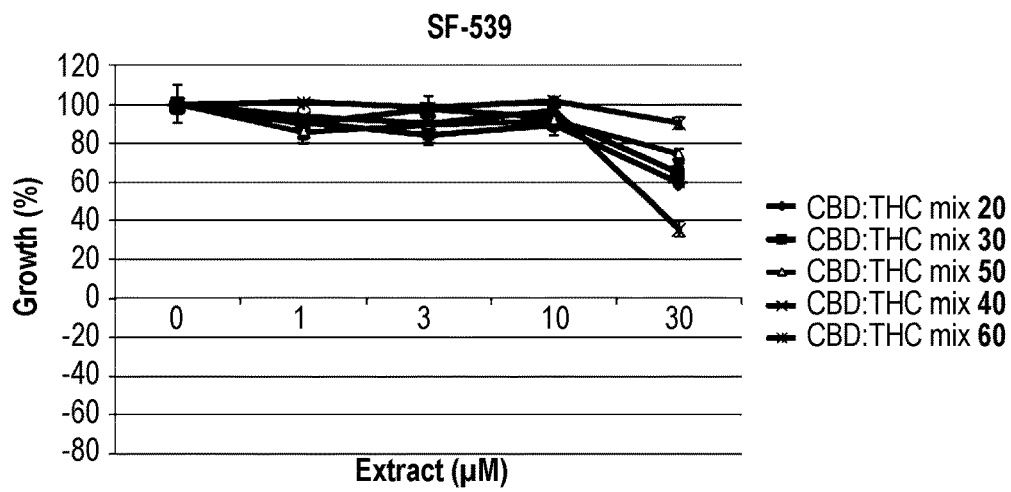
FIG. 6B shows the growth of SF-539 brain cancer cells in the presence THC and CBD at concentrations equal to the concentration in blended *cannabis* oil compositions and single-strain *cannabis* oil compositions.
Figure 6C:
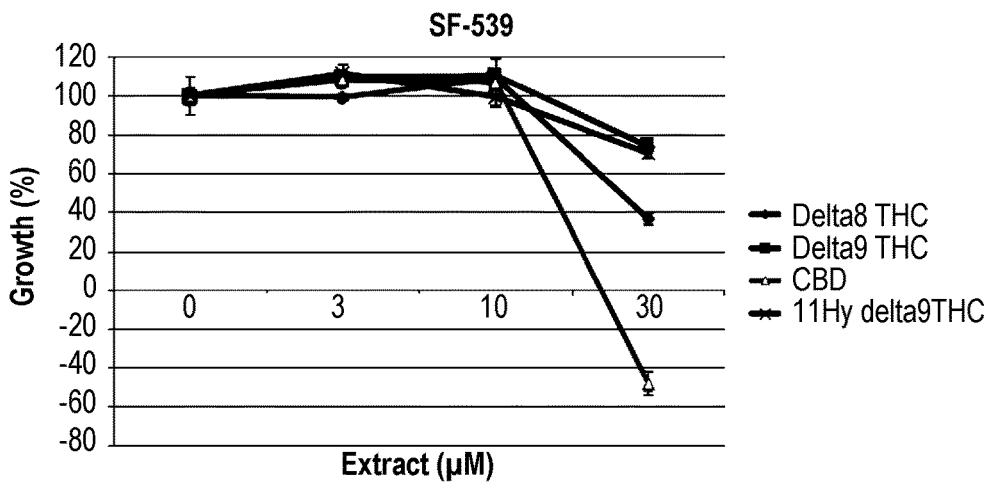
FIG. 6C shows the growth of SF-539 brain cancer cells in the presence of isolated cannabinoids.
Figure 7A:
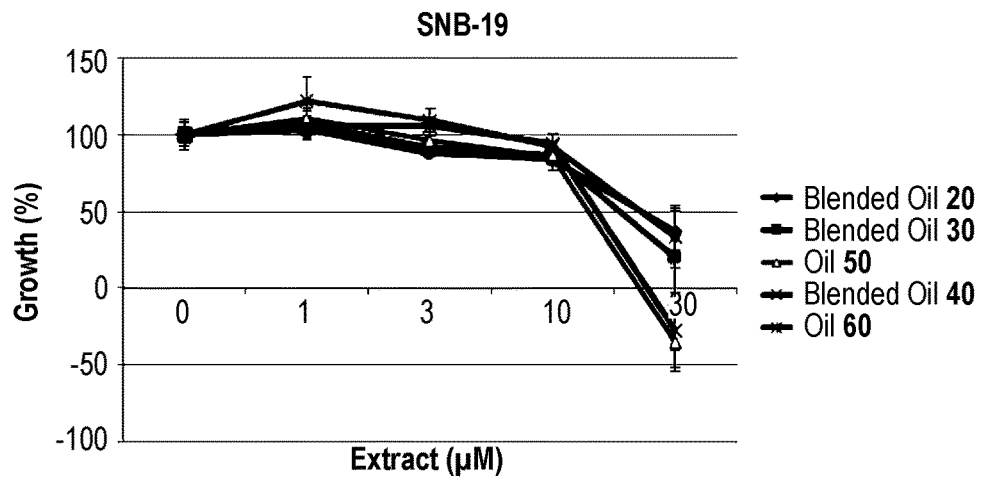
FIG. 7A shows the growth of SNB-19 brain cancer cells in the presence of blended *cannabis* oil compositions and single-strain *cannabis* oil compositions.
Figure 7B:
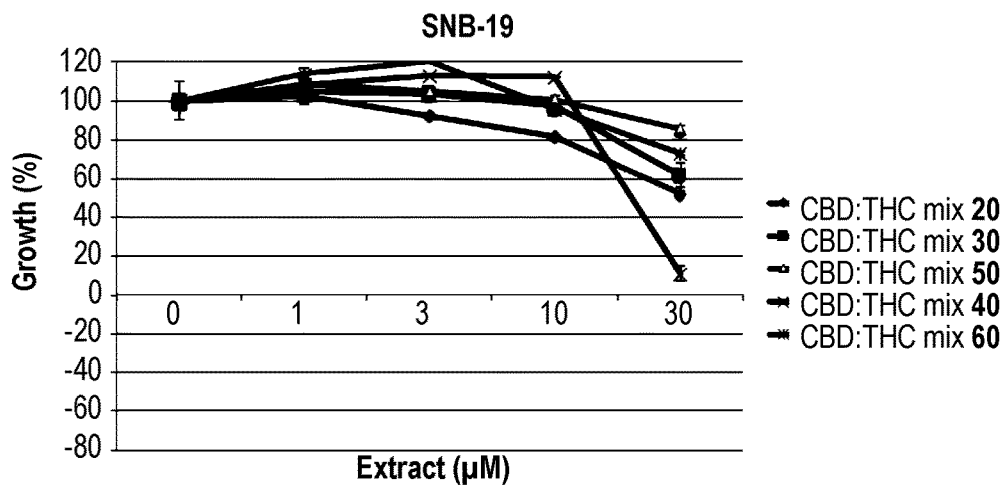
FIG. 7B shows the growth of SNB-19 brain cancer cells in the presence THC and CBD at concentrations equal to the concentration in blended *cannabis* oil compositions and single-strain *cannabis* oil compositions.
Figure 7C:
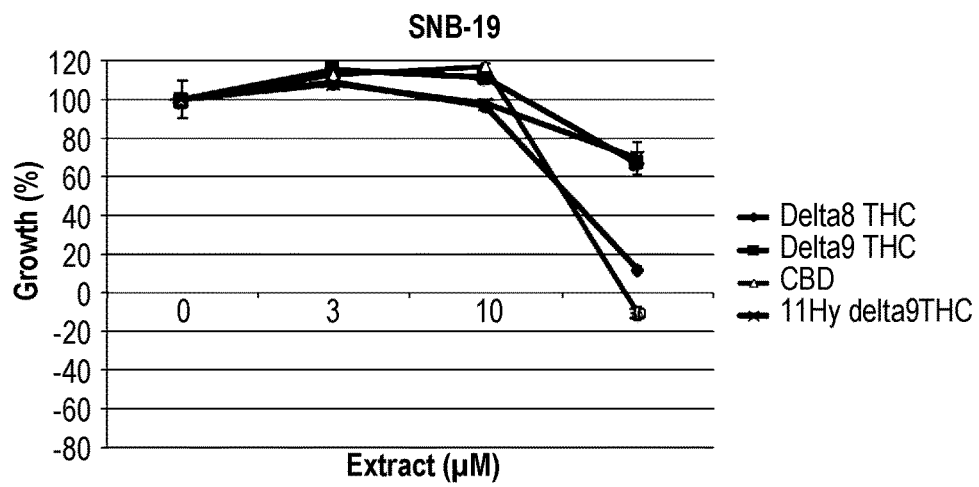
FIG. 7C shows the growth of SNB-19 brain cancer cells in the presence of isolated cannabinoids.
Figure 8A:
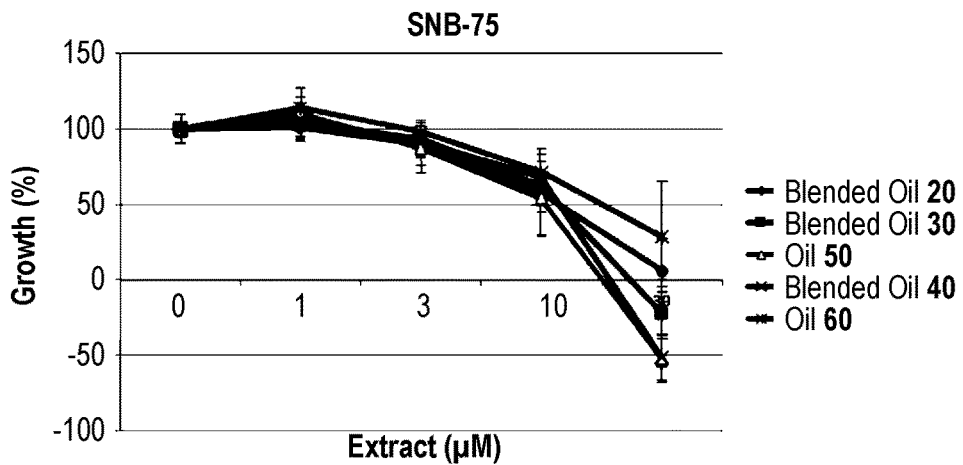
FIG. 8A shows the growth of SNB-75 brain cancer cells in the presence of blended *cannabis* oil compositions and single-strain *cannabis* oil compositions.
Figure 8B:
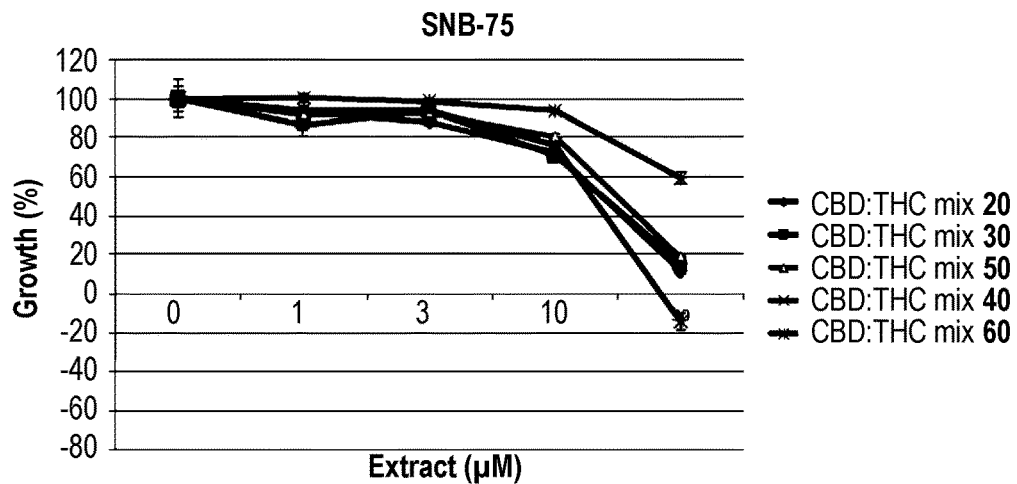
FIG. 8B shows the growth of SNB-75 brain cancer cells in the presence THC and CBD at concentrations equal to the concentration in blended *cannabis* oil compositions and single-strain *cannabis* oil compositions.
Figure 8C:
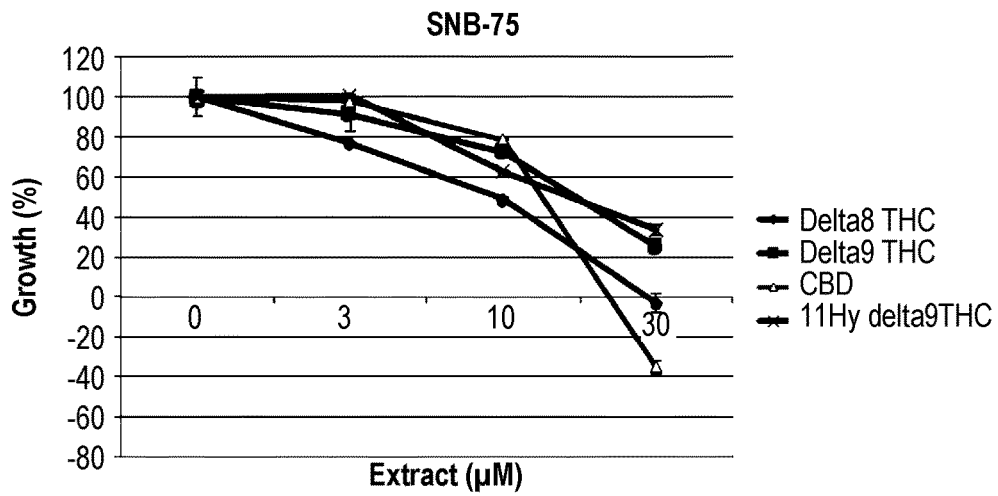
FIG. 8C shows the growth of SNB-75 brain cancer cells in the presence of isolated cannabinoids.
Figure 9A:
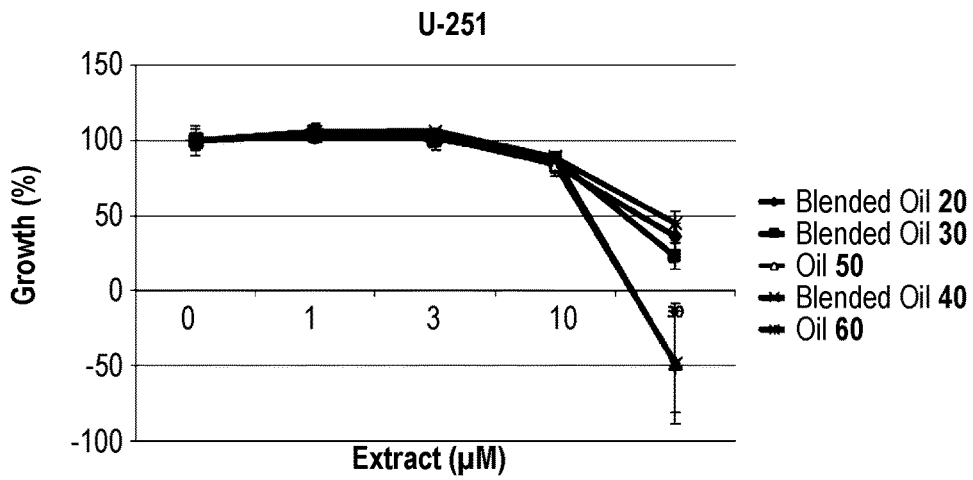
FIG. 9A shows the growth of U251 brain cancer cells in the presence of blended *cannabis* oil compositions and single-strain *cannabis* oil compositions.
Figure 9B:
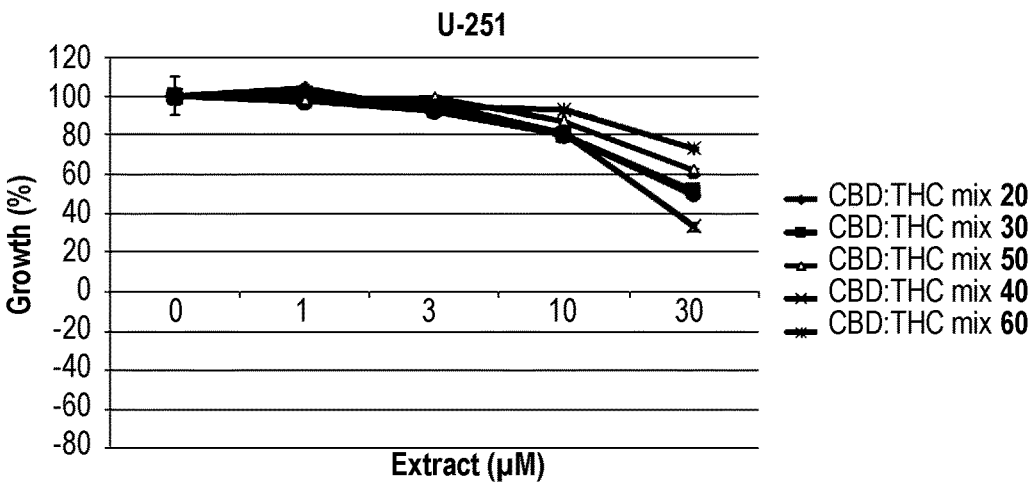
FIG. 9B shows the growth of U251 brain cancer cells in the presence THC and CBD at concentrations equal to the concentration in blended *cannabis* oil compositions and single-strain *cannabis* oil compositions.
Figure 9C:
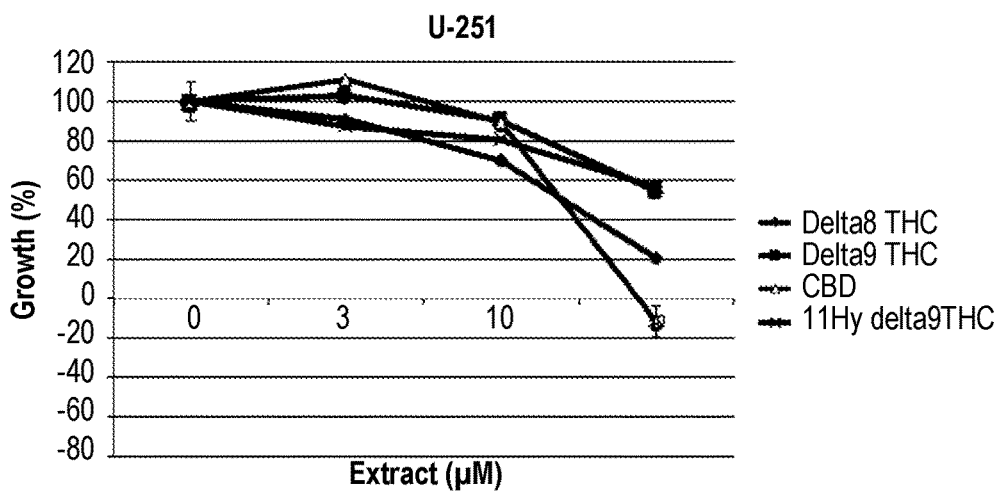
FIG. 9C shows the growth of U251 brain cancer cells in the presence of isolated cannabinoids.
Figure 10A:
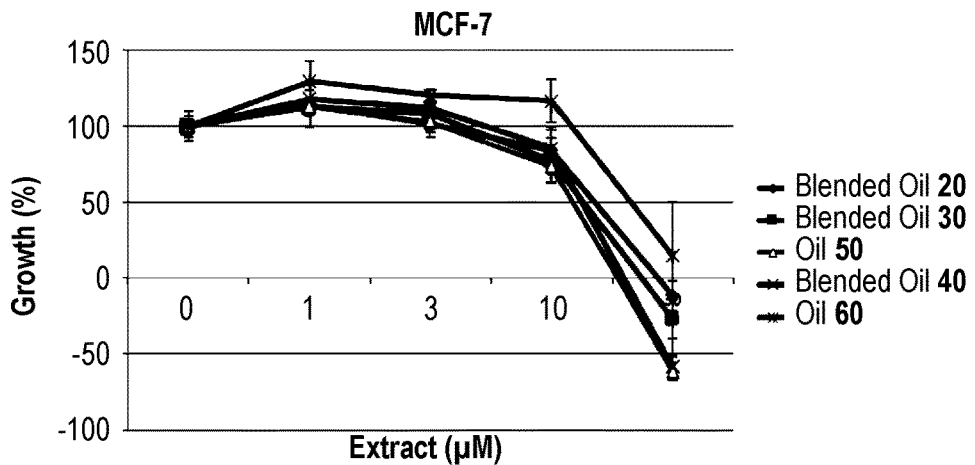
FIG. 10A shows the growth of MCF-7 breast cancer cells in the presence of blended *cannabis* oil compositions and single-strain *cannabis* oil compositions.
Figure 10B:
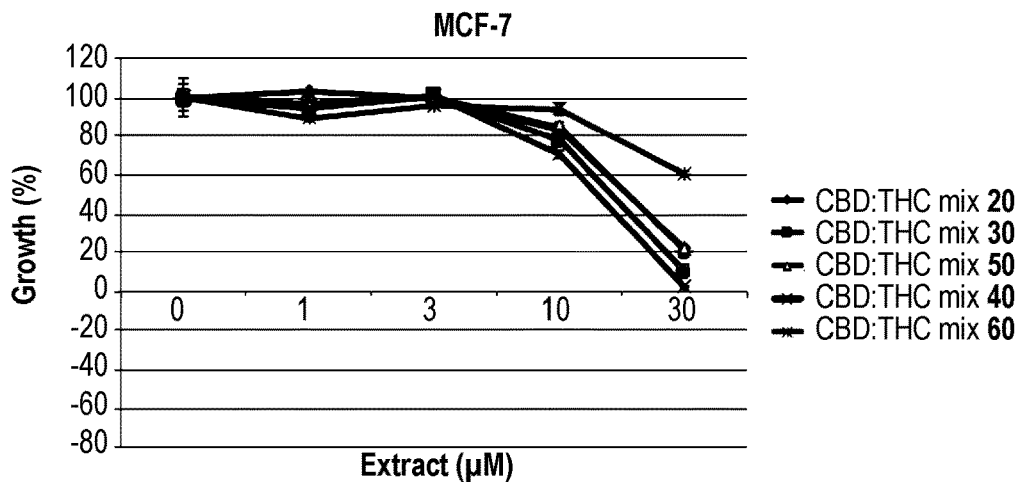
FIG. 10B shows the growth of MCF-7 breast cancer cells in the presence THC and CBD at concentrations equal to the concentration in blended *cannabis* oil compositions and single-strain *cannabis* oil compositions.
Figure 10C:
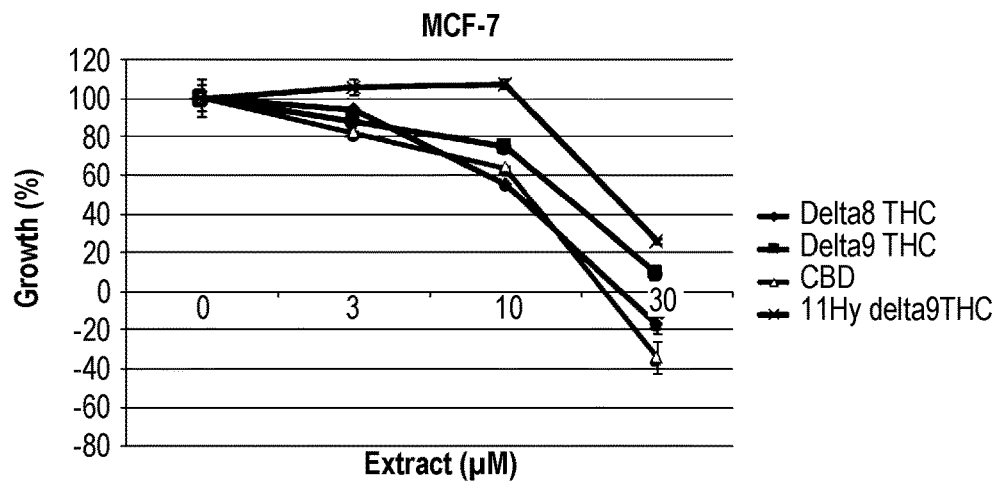
FIG. 10C shows the growth of MCF-7 breast cancer cells in the presence of isolated cannabinoids.
Figure 11A:
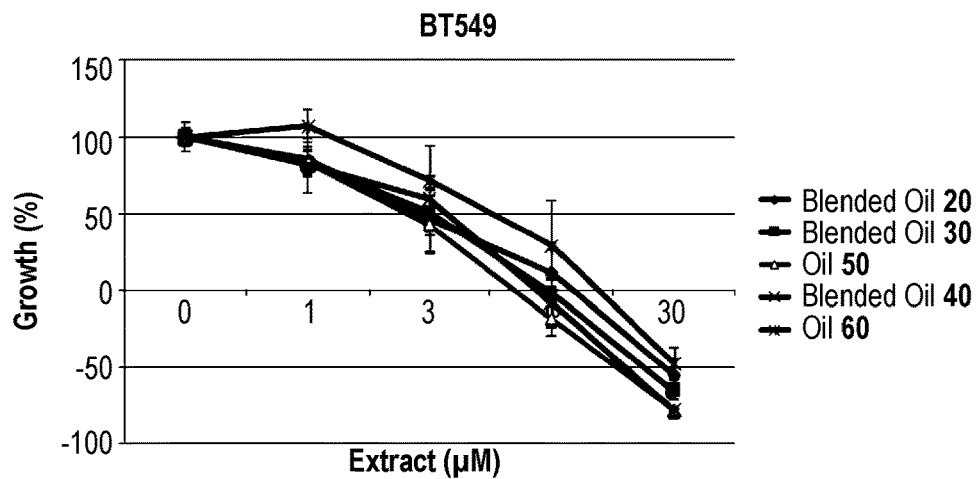
FIG. 11A shows the growth of BT549 breast cancer cells in the presence of blended *cannabis* oil compositions and single-strain *cannabis* oil compositions.
Figure 11B:
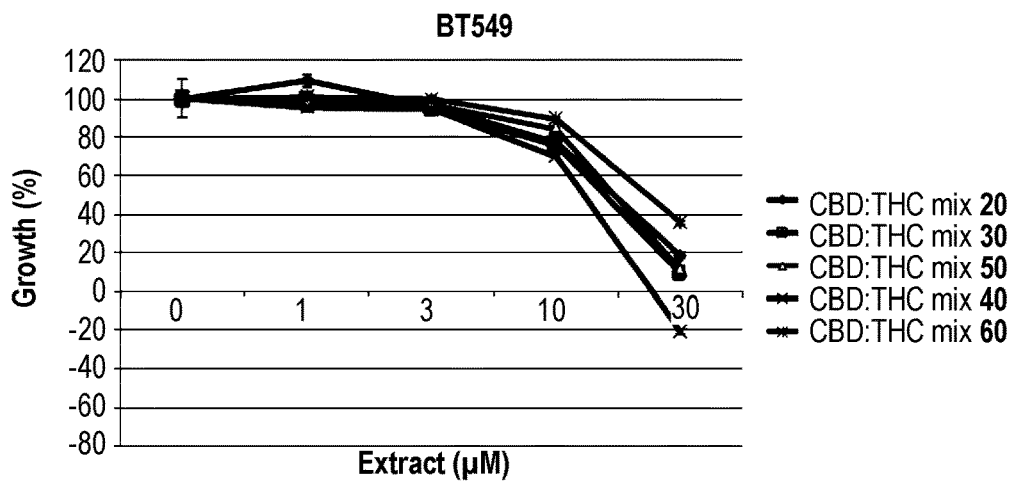
FIG. 11B shows the growth of BT549 breast cancer cells in the presence THC and CBD at concentrations equal to the concentration in blended *cannabis* oil compositions and single-strain *cannabis* oil compositions.
Figure 11C:
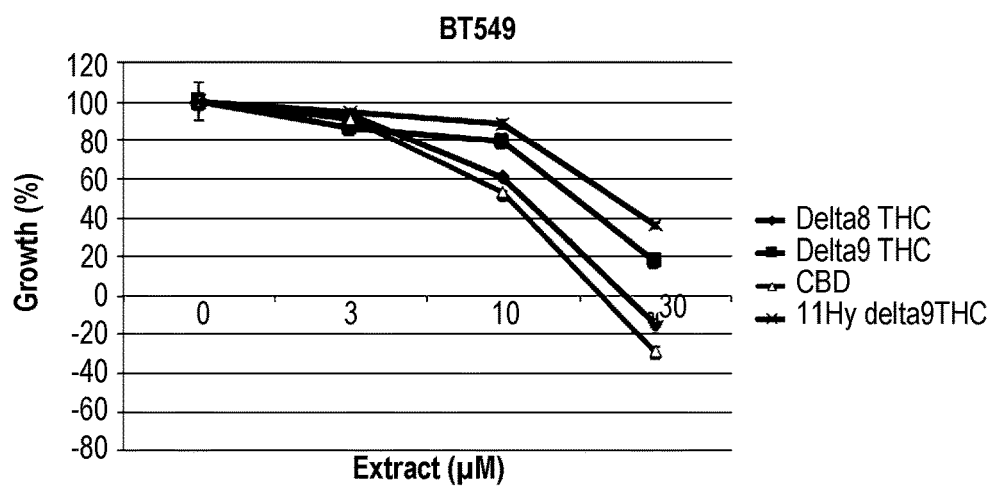
FIG. 11C shows the growth of BT549 breast cancer cells in the presence of isolated cannabinoids.
Figure 12A:
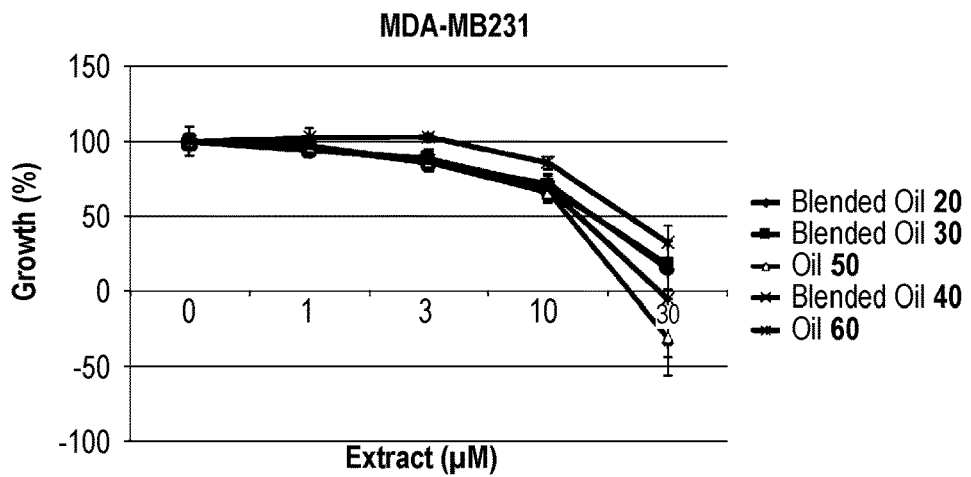
FIG. 12A shows the growth of MDA-MB231 breast cancer cells in the presence of blended *cannabis* oil compositions and single-strain *cannabis* oil compositions.
Figure 12B:
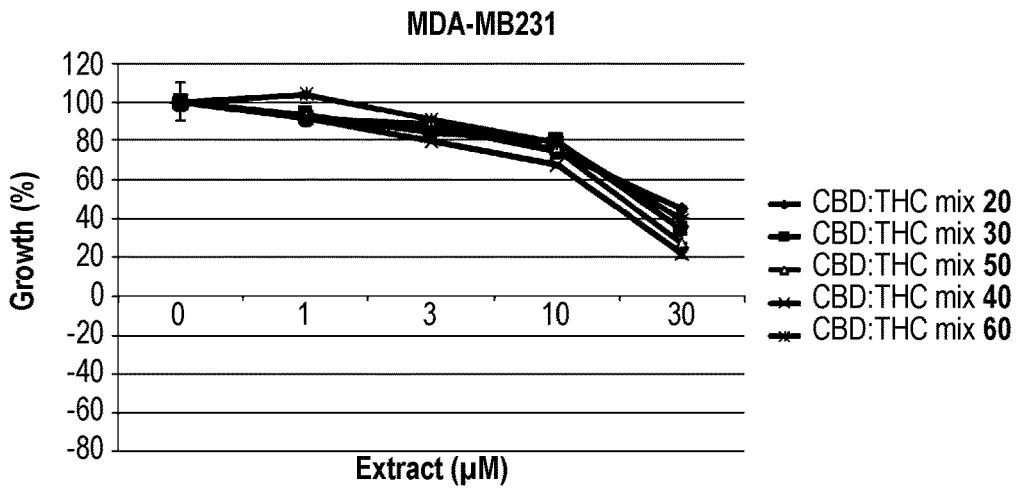
FIG. 12B shows the growth of MDA-MB231 breast cancer cells in the presence THC and CBD at concentrations equal to the concentration in blended *cannabis* oil compositions and single-strain *cannabis* oil compositions.
Figure 12C:
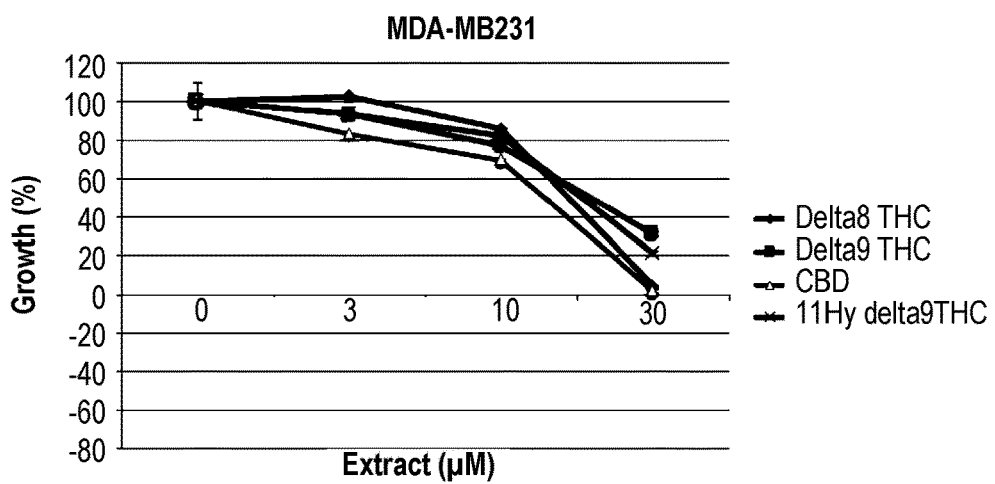
FIG. 12C shows the growth of MDA-MB231 breast cancer cells in the presence of isolated cannabinoids.
Figure 13A:
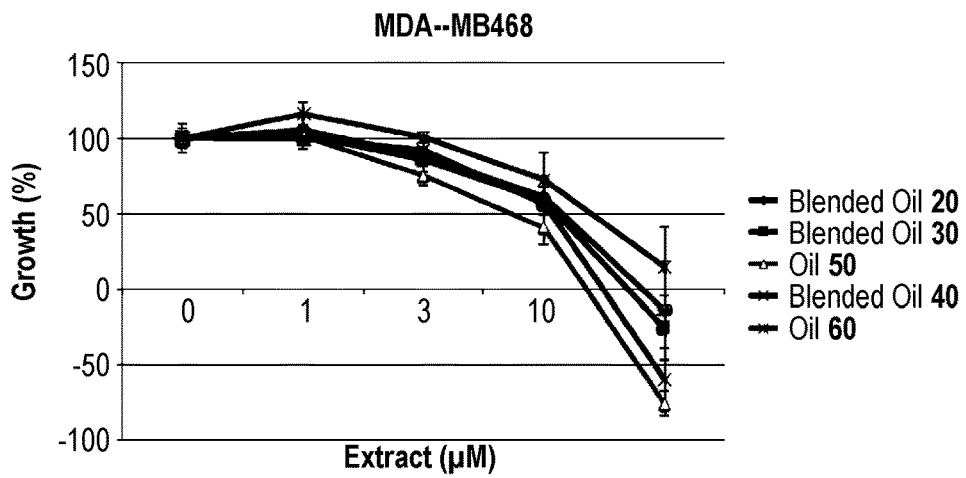
FIG. 13A shows the growth of MDA-MB468 breast cancer cells in the presence of blended *cannabis* oil compositions and single-strain *cannabis* oil compositions.
Figure 13B:
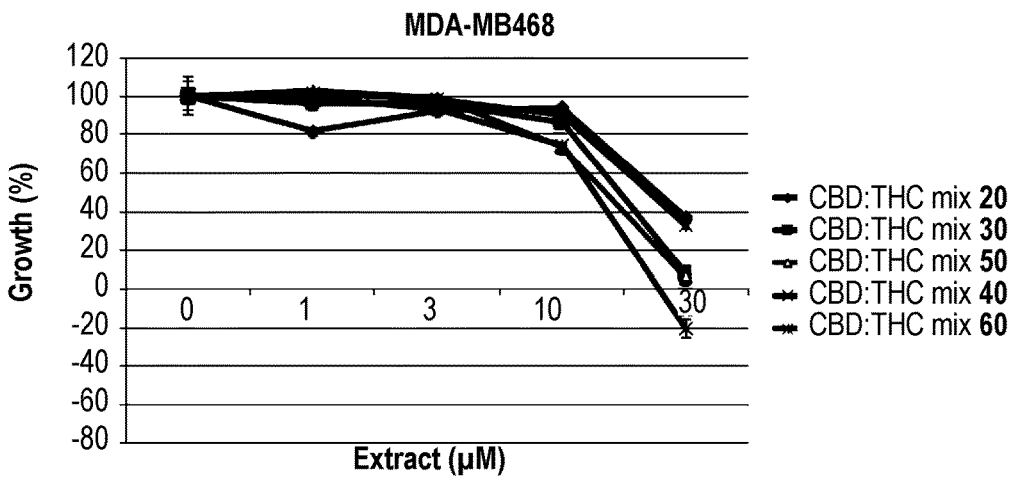
FIG. 13B shows the growth of MDA-MB468 breast cancer cells in the presence THC and CBD at concentrations equal to the concentration in blended *cannabis* oil compositions and single-strain *cannabis* oil compositions.
Figure 13C:
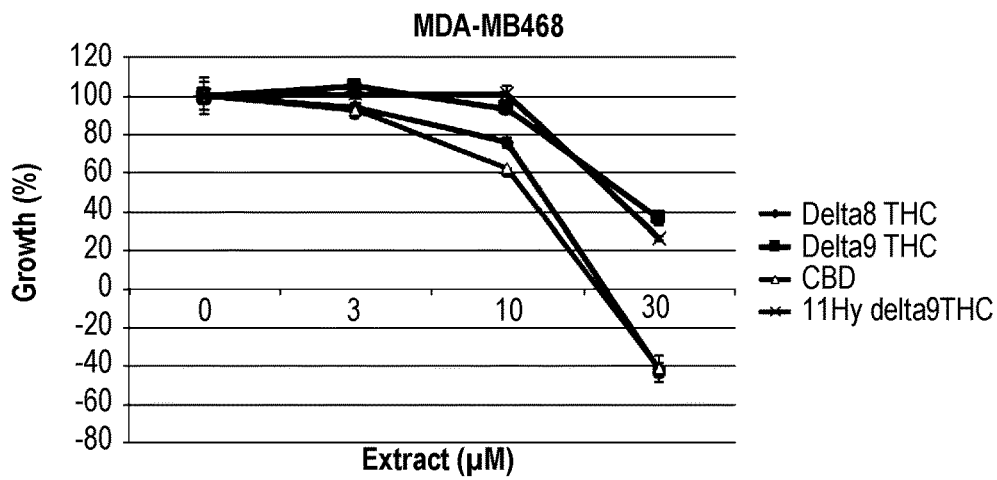
FIG. 13C shows the growth of MDA-MB468 breast cancer cells in the presence of isolated cannabinoids.
Figure 14A:
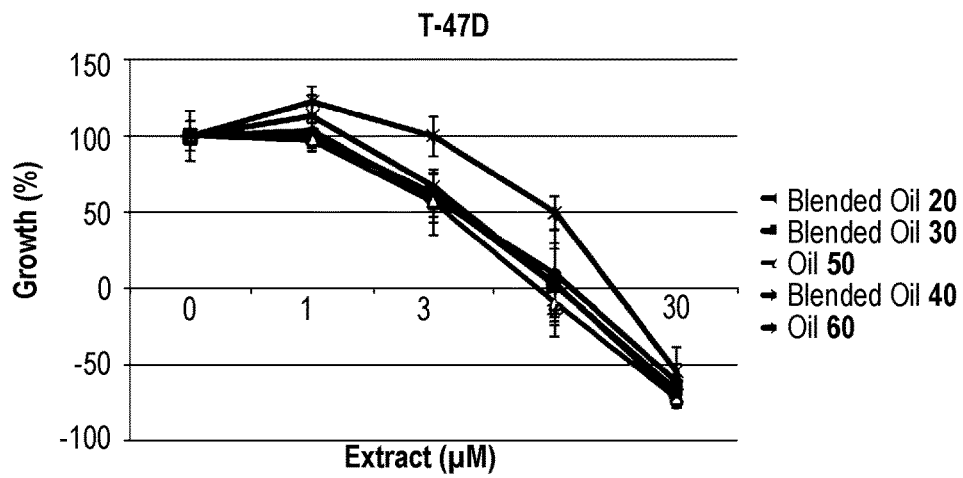
FIG. 14A shows the growth of T-47D breast cancer cells in the presence of blended *cannabis* oil compositions and single-strain *cannabis* oil compositions.
Figure 14B:
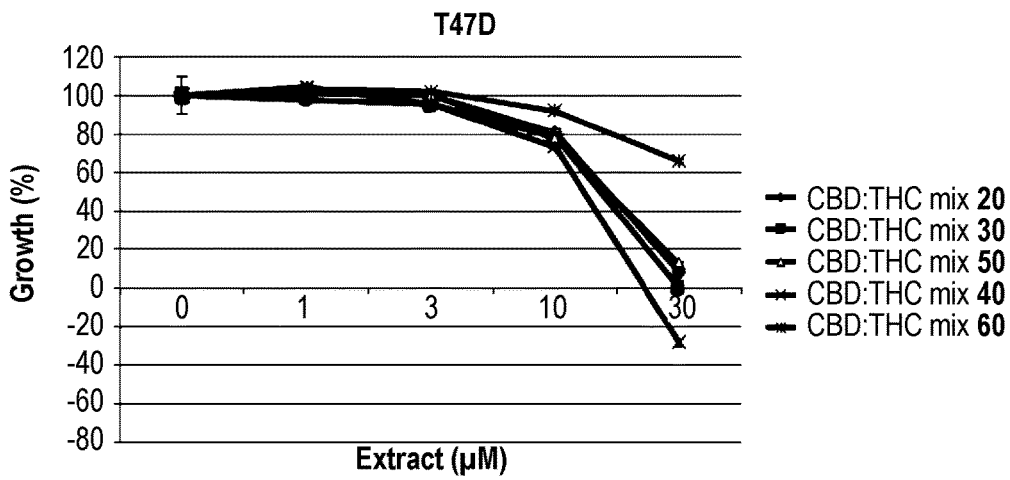
FIG. 14B shows the growth of T-47D breast cancer cells in the presence THC and CBD at concentrations equal to the concentration in blended *cannabis* oil compositions and single-strain *cannabis* oil compositions.
Figure 14C:
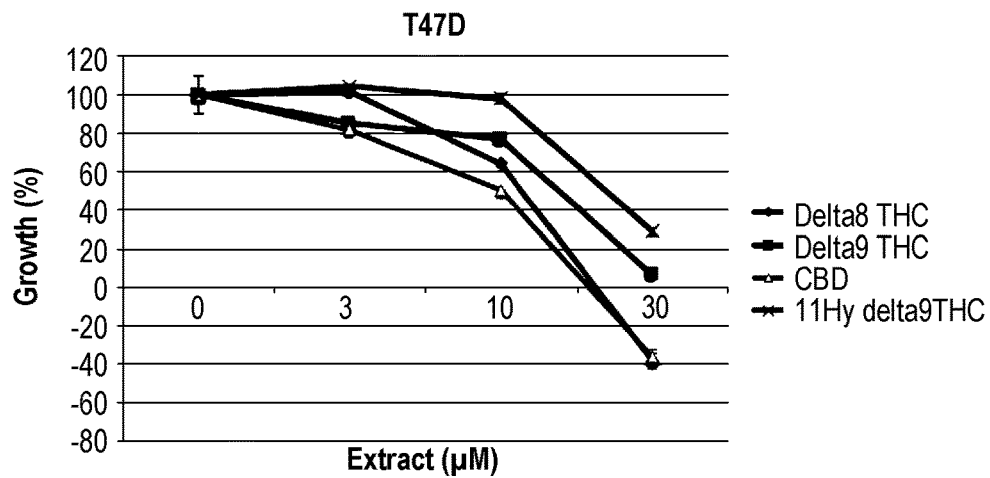
FIG. 14C shows the growth of T-47D breast cancer cells in the presence of isolated cannabinoids.
Figure 15A:
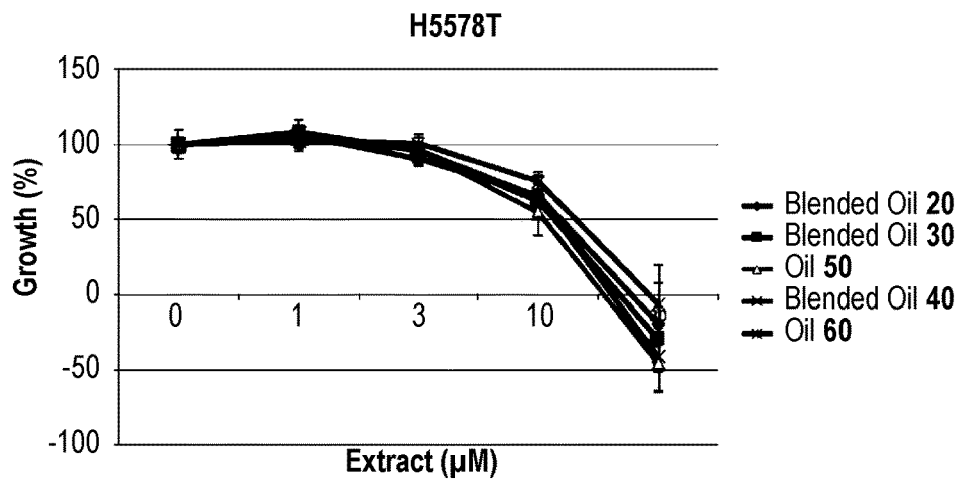
FIG. 15A shows the growth of HS578T breast cancer cells in the presence of blended *cannabis* oil compositions and single-strain *cannabis* oil compositions.
Figure 15B:
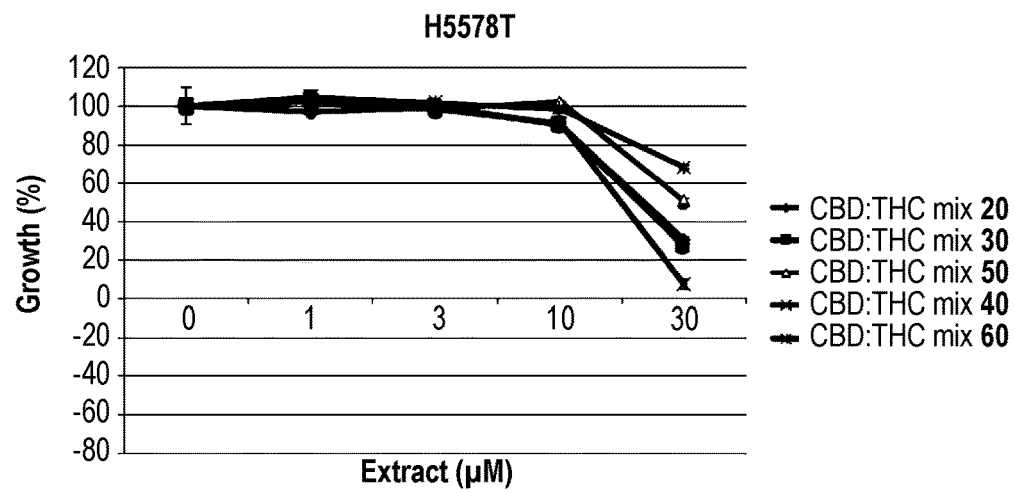
FIG. 15B shows the growth of HS578T breast cancer cells in the presence THC and CBD at concentrations equal to the concentration in blended *cannabis* oil compositions and single-strain *cannabis* oil compositions.
Figure 15C:
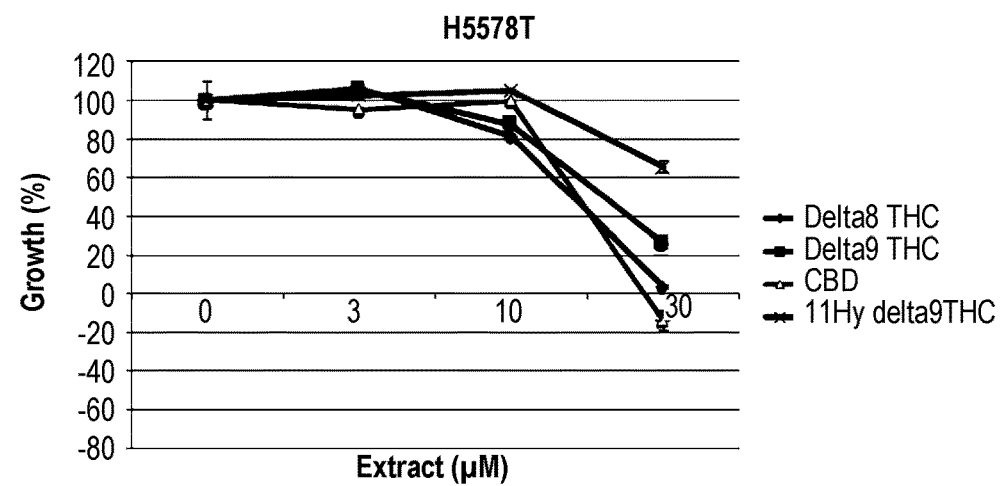
FIG. 15C shows the growth of HS578T breast cancer cells in the presence of isolated cannabinoids.

Reference is now made to FIG. 3, which is a graph depicting THC and CBD percentages in *cannabis* oil compositions made from three strains of *cannabis* plant material 103, according to one or more embodiments. In one embodiment, the *cannabis* oil composition can be made from *cannabis* plant material comprising the AC/DC *cannabis* strain. In another embodiment, the *cannabis* oil composition can be made from *cannabis* plant material comprising the Blueberry *cannabis* strain. In yet another embodiment, the *cannabis* oil composition can be made from *cannabis* plant material comprising the Cannatonic *cannabis* strain.

The three *cannabis* strains were selected for their varying levels of cannabinoids 107. For example, the AC/DC strain was selected to represent *cannabis* strains with high levels of CBD and low levels of THC. Also, for example, the Blueberry strain was selected to represent *cannabis* strains with high levels of THC and low levels of CBD. Also yet another example, the Cannatonic strain was selected to represent *cannabis* strains with moderate levels CBD and THC.

As depicted in FIG. 3, *cannabis* oil compositions of uniform volume were made with 30% w/w vitamin E 121 mixed with extract 119 produced from the AC/DC, Blueberry, and Cannatonic strains of *cannabis* plant material 103. These *cannabis* oil compositions were assayed using HPLC-UV to determine the level of cannabinoids 107 in each *cannabis* oil composition. In addition, HPLC-UV was also performed on extracts with no vitamin E 121 to determine the level of cannabinoids 107 in such extracts.

While the mixing of extract 119 with vitamin E 121 reduced the amount of cannabinoids detected in the *cannabis* oil compositions relative to the extracts, 30% w/w of vitamin E 121 was discovered to reduce the viscosity of the *cannabis* oil compositions made from all three strains. Moreover, organoleptic analysis of each *cannabis* oil composition revealed that 30% w/w of vitamin E 121 also did not have an adverse effect on the aromatic or gustatory qualities of the extract 119 in the *cannabis* oil composition.

Example 2. Preparation of *Cannabis* Oils

Preparation of AC/DC *Cannabis* Oil.

2 pounds of *cannabis* plant material (strain: AC/DC) and 17 L of EtOH were stored for 24 hours at −18° C. prior to extraction. The 2 pounds were split between two colanders, which were placed on top of a collection vessel. 3 L of cold EtOH was poured evenly over each pound (6 L total) of plant material and collected in the vessel below. After dripping for about 2 min, the resulting solution was poured over the same plant material and collected and repeated 3 more times (5 total pours for over each colander). After the final pour, the material was left to drip into the collection vessel for 20 min. The solution was then filtered through the Chemex filter (~300 micron) into a collection flask. This combined solution was poured into a glass jar with airtight lid and left underneath a plasma light source for 15 minutes and then stored at −18° C. for 20 hours (Batch 2-1A).

The plant material from the colanders was placed in a 5-gallon bucket and covered with 11 L of cold EtOH and left to sit for 2 hours. The material was filtered through the Chemex filter into a collection flask. This combined solution was poured into a glass jar with airtight lid and left underneath a plasma light source for 18 hours. Following exposure to light, the solution was stored at −18° C. for 20 hours (Batch 2-1B).

The 2-1A and 2-1B batches were independently filtered while cold through a Buchner funnel with Whatman 150 mm filter paper in place into a filtration flask while under vacuum. The 2-1A batch solution was split between two Megahome distillers. The distillers were turned on and the distillate was collected in a glass receiving vessel until complete. Upon completion, the oil in the distiller was immediately transferred into a tared, glass petri dish and placed into the vacuum oven at 46° C. and 27 mbar for 87 hours (the pressure was checked daily and brought back down to 21-27 mbar as necessary). The 2-1B batch solution was split between three Megahome distillers. The distillers were turned on and the distillate was collected in a glass receiving vessel until complete. Upon completion, the oil in the distiller was immediately transferred into a tared, glass petri dish and placed into the vacuum oven at 44° C. and 22 mbar for 120 hours.

Preparation of Prize Kush Cannabis Oil.

3 pounds of cannabis plant material (strain: Prize Kush) and 21 L of EtOH were stored for 24 hours at −18° C. prior to extraction. The 3 pounds were split between three colanders, which were placed on top of a collection vessel. 3 L of cold EtOH was poured evenly over each pound (9 L total) of plant material and collected in the vessel below. After dripping for about 2 min, the resulting solution was poured over the same plant material and collected and repeated 4 more times (6 total pours for over each colander). After the final pour, the material was left to drip into the collection vessel for 20 min. The solution was then filtered through the Chemex filter (~300 micron) into a collection flask. This combined solution was poured into a glass jar with airtight lid and then stored at −18° C. for 20 hours (2-2A).

The plant material from the colanders was placed in a 5-gallon bucket and covered with 12 L of cold EtOH and left to sit for 2 hours. The material was filtered through the Chemex filter into a collection flask. This combined solution was poured into a glass jar with airtight lid and left underneath a plasma light source for 18 hours. Following exposure to light, the solution was stored at −18° C. for 20 hours (2-2B).

The 2-2A and 2-2B batches were independently filtered while cold through a Buchner funnel with Whatman 150 mm filter paper in place into a filtration flask while under vacuum. The 2-2A batch solution was split between two Megahome distillers. The distillers were turned on and the distillate was collected in a glass receiving vessel until complete. Upon completion, the oil in the distiller was immediately transferred into a tared, glass petri dish and placed into the vacuum oven at 47° C. and 27 mbar for 72 hours (the pressure was checked daily and brought back down to 21-27 mbar as necessary). The 2-2B batch solution was split between four Megahome distillers. The distillers were turned on and the distillate was collected in a glass receiving vessel until complete. Upon completion, the oil in the distiller was immediately transferred into a tared, glass petri dish and placed into the vacuum oven at 47° C. and 27 mbar for 72 hours.

Preparation of Blueberry Cannabis Oil.

2 pounds of cannabis plant material (strain: Blueberry) and 14 L of EtOH were stored for 24 hours at −18° C. prior to extraction. The 2 pounds were split between two colanders, which were placed on top of a collection vessel. 3 L of cold EtOH was poured evenly over each pound (6 L total) of plant material and collected in the vessel below. After dripping for about 2 min, the resulting solution was poured over the same plant material and collected and repeated 4 more times (6 total pours for over each colander). After the final pour, the material was left to drip into the collection vessel for 20 min. The solution was then filtered through the Chemex filter (~300 micron) into a collection flask. This combined solution was poured into a glass jar with airtight lid and then stored at −18° C. for 20 hours (2-A).

The plant material from the colanders was placed in a 5-gallon bucket and covered with 8 L of cold EtOH and left to sit for 2 hours. The material was filtered through the Chemex filter into a collection flask. This combined solution was poured into a glass jar with airtight lid and left underneath a plasma light source for 18 hours. Following exposure to light, the solution was stored at −18° C. for 20 hours (2-3B).

The A and B batches were independently filtered while cold through a Buchner funnel with Whatman 150 mm filter paper in place into a filtration flask while under vacuum. The 2-A batch solution was split between two Megahome distillers. The distillers were turned on and the distillate was collected in a glass receiving vessel until complete. Upon completion, the oil in the distiller was immediately transferred into a tared, glass petri dish and placed into the vacuum oven at 46° C. and 21 mbar for 143 hours (the pressure was checked daily and brought back down to 21-27 mbar as necessary). The 2-3B batch solution was split between four Megahome distillers. The distillers were turned on and the distillate was collected in a glass receiving vessel until complete. Upon completion, the oil in the distiller was immediately transferred into a tared, glass petri dish and placed into the vacuum oven at 47° C. and 27 mbar for 69 hours.

Example 3. Preparation of Cannabis Oils

A first extract (Extract A) is prepared according to the following procedure.

Ethanol (EtOH; Alchemical Solutions organic 190 proof neutral grain wheat spirits) and raw cannabis material are stored in at −10° C. for at least 16 hr, or for other time periods as necessary. In certain instances, ethanol and raw cannabis material are used at room temperature. Three liters of alcohol are typically used for each pound of raw cannabis material.

Cold (or room temperature) raw cannabis material is placed in a tabletop Buchner funnel (18"-36" diameter; Bel-Art) with perforated, creped white cellulose filter paper in place. Ethanol-compatible tubing (e.g., Tyron Tyoprene) is attached to the funnel drain spigot and connected to a collection media bottle. 1-3 lb of raw cannabis material is typically used with an 18" funnel; 2-5 lb of raw cannabis material is typically used with a 24" funnel; and 4-10 lb of cannabis material is typically used with a 36" funnel. 1-5 L (e.g., 3 L) of EtOH per lb of raw cannabis material is poured evenly over the raw cannabis material while collecting the ethanolic eluate ("menstruum") in a 2-5 L media bottle. The menstruum is collected and re-poured over the cannabis material 3-6 times. Re-pouring is stopped before the menstruum turns from yellow-toned to green.

If necessary, the menstruum is filtered through a Chemex 300-μm mesh stainless steel filter into a Chemex glass flask. The menstruum is then transferred to a media bottle with screw cap and stored at −10° C. for no less than 18 hr.

A second extract (Extract B) is prepared using the material ("marc") remaining from the procedure described above. Marc from extract A remains in the tabletop Buchner funnel, and the funnel spigot is closed to prevent draining. Cold (or room temperature) EtOH is poured over the marc remaining in the Buchner funnel in an amount sufficient to completely cover the marc (e.g., 4-5 L per lb). The marc is soaked ("macerated") for a period of time typically ranging from a few minutes to about 6 hours (e.g., 2 hr). If raw *cannabis* material is used without prior preparation of Extract A, the maceration step is typically conducted for less than 1 hr (e.g., less than 15 min). After the maceration step, the funnel valve is opened to separate the marc from the menstruum and menstruum is collected in a suitable vessel.

The menstruum is filtered through a Chemex mesh stainless steel filter into a Chemex glass flask (this step is optional depending upon amount of marc in menstruum after maceration step). The filtered menstruum is poured from the Chemex flask back into a media bottle with screw cap.

For extract B, menstruum, while still in media bottles, is optionally exposed to sunlight (~2 hr) or plasma light (~8-10 hr). Menstruum is solarized until the nettle green color shifts to yellow brown. After solarization, the media bottle is placed into a freezer for 18-48 hr.

An appropriately sized cellulose filter paper is placed on top of the perforated filter of the table-top Buchner funnel. The vacuum tubing, which is connected to a vacuum, is attached to the Buchner funnel. Menstruum, that is still in the media bottle, is removed from freezer. The filter paper is wetted using EtOH. The vacuum pump is turned on and the valve is opened to the vacuum pump. Just before the extract is poured into the funnel, approximately half of an inch of EtOH is poured into the funnel quickly followed by the extract.

The filtered menstruum is poured into an evaporation flask (no more than ~60% full). A B-491 rotavapor is prepared by turning on the heating bath to around 50° C. (e.g., 20-60° C.) and turning on a F-105 recirculating chiller with the water temperature set to 5° C. The evaporation flask is secured to the R-215 rotavapor and the rotation rate of the evaporation flask is set to around 150 rpm (e.g., 30-300 rpm). The vacuum gradient is initiated using a V-855 vacuum controller. The vacuum pressure is maintained around 125 mbar (e.g., 50-300 mbar). Once the liquid has stopped condensing, the vacuum is released and the rotation of the evaporation flask is slowly stopped.

The resulting oil from the evaporation step is optionally transferred to an appropriately sized round-bottom flask (no more than ~40% full) with a magnetic stir bar in the oil for heating. The round-bottom flask containing the evaporated oil/liquid is placed in an OptiTherm reaction block on an IKA stirring hotplate. A condenser is attached to the top of the round-bottom flask and the recirculating chiller is turned on. Once the condenser is turned on, stirring and heating is initiated. The oil is heated at around 120° C. (e.g., 60-150° C.) for between 5 min and 24 hr (e.g., 1 hr) depending on the temperature of the heating block and the desired ratio of acidic to neutral cannabinoids.

Prior to optional silica gel filtration, the oil is homogenized in EtOH (or EtOAc or Heptane; 1:2 ratio, i.e., 100 g oil to 200 mL solvent). Around 2 parts silica gel is combined with 1 part oil/EtOH mixture, and the resulting slurry is concentrated on a rotavapor. A silica gel pad is prepared in an appropriate funnel (6:1 ratio, i.e., 600 g silica to 100 g oil), which is positioned on a vacuum flask, and is wetted with EtOH. The homogenized oil (optionally with silica gel) is placed on top of the silica pad and is pulled using light vacuum until all solution is absorbed on silica. EtOH is gently poured (1000 mL for 100 g of oil) on top of the silica gel and is pulled through with vacuum. The filtrate is collected in a flask and concentrated on the rotavapor at 40° C. bath temperature and 100 mbar vacuum pressure.

The extract is placed into an Across International Vacuum oven set to 46° C./115° F. for no less than 12 hours and no more than 5 days. Alternatively, the extract is transferred to appropriate glass vials for use with a Buchi multivapor apparatus set to 50-70° C. under reduced pressure between 10-100 mbar for a specified time. Once excess EtOH has been fully evaporated, the extract is organoleptically analyzed for determination of complete EtOH removal.

Example 4. Cannabinoid and Terpene Content of *Cannabis* Oils

The cannabinoid content and terpene content of *cannabis* oils prepared according to the methods of the invention was studied. Cannabinoid content was determined using liquid chromatography/mass spectrometry (LC-MS), and terpene content was determined using gas chromatography with flame ionization detection (GC-FID).

TABLE 4

Neutral cannabinoid content of *cannabis* oils

| Example | Cannabis Strain | Cannabinoid content (mg cannabinoid per gram oil) | | | |
|---|---|---|---|---|---|
| | | THC | CBD | CBG | CBN |
| 2-1A | AC/DC | 26.3 | 642.4 | 28.8 | 0.7 |
| 2-1B | AC/DC | 38.4 | 594.1 | 28.5 | 1.2 |
| 2-2A | Prize Kush | 675.6 | 1.0 | 38.7 | 2.5 |
| 2-2B | Prize Kush | 655.6 | 5.0 | 32.6 | 14.9 |
| 2-3A | Blueberry | 790.4 | 7.8 | 11.7 | 8.5 |
| 3A | AC/DC | 26.3 | 659.8 | 24.6 | 0.9 |
| 4B | Afghan Goo | 686.6 | 10.8 | 30.1 | 13.4 |
| 5A | Blackberry Kush | 773.8 | 10.7 | 22.5 | 9.2 |
| 6A | Blue Diesel | 744.5 | 26.4 | 27.7 | 6.8 |
| 7A | Buddha Passion | 282.1 | 484.8 | 17.7 | 3.1 |
| 8A | Cannatonic | 366.0 | 319.9 | 15.5 | 18.5 |
| 9A | Cannatonic | 25.8 | 668.2 | 18.9 | 0.3 |
| 10A | Cannatonic | 186.2 | 525.1 | 30.7 | 2.9 |
| 11A | Girl Scout Cookies | 677.2 | 0.0 | 59.0 | 6.3 |
| 12B | Harle OG | 31.2 | 659.3 | 26.1 | 2.8 |
| 13A | Harle Tsu | 200.4 | 539.4 | 34.3 | 3.0 |
| 14A | Harlequin | 209.1 | 569.2 | 29.9 | 2.2 |
| 14B | Harlequin | 171.3 | 511.2 | 24.8 | 6.1 |
| 15A | Infinite Euphoria | 745.0 | 11.8 | 48.4 | 9.1 |
| 16A | Medihaze | 214.7 | 493.7 | 31.8 | 3.3 |
| 17B | Medihaze | 217.7 | 450.2 | 24.5 | 5.9 |
| 18B | Prize Kush | 707.8 | 5.1 | 34.9 | 11.4 |
| 19A | Sour Kush | 737.7 | 12.4 | 16.2 | 5.9 |
| 19A | Blueberry | 639.1 | 24.2 | 13.3 | 13.5 |

TABLE 5

Acidic cannabinoid content of *cannabis* oils

| Example | Cannabis Strain | Cannabinoid content (mg cannabinoid per gram oil) | | |
|---|---|---|---|---|
| | | THCA | CBDA | CBGA |
| 2-1A | AC/DC | 0.0 | 2.6 | 0.0 |
| 2-1B | AC/DC | 0.0 | 8.2 | 0.0 |
| 2-2A | Prize Kush | 0.0 | 0.0 | 0.0 |
| 2-2B | Prize Kush | 0.0 | 0.0 | 1.8 |
| 2-3A | Blueberry | 0.0 | 0.5 | 0.0 |
| 3A | AC/DC | 0.0 | 5.7 | 0.0 |
| 4B | Afghan Goo | 3.3 | 0.3 | 4.4 |
| 5A | Blackberry Kush | 1.9 | 0.3 | 2.9 |
| 6A | Blue Diesel | 2.8 | 0.4 | 6.6 |
| 7A | Buddha Passion | 0.0 | 25.6 | 1.9 |
| 8A | Cannatonic | 0.0 | 2.6 | 0.8 |
| 9A | Cannatonic | 0.0 | 0.2 | 2.3 |
| 10A | Cannatonic | 0.0 | 1.8 | 0.0 |
| 11A | Girl Scout Cookies | 0.0 | 0.0 | 0.0 |
| 12B | Harle OG | 0.0 | 9.2 | 1.6 |
| 13A | Harle Tsu | 0.0 | 45.9 | 3.8 |
| 14A | Harlequin | 0.0 | 4.1 | 1.1 |
| 14B | Harlequin | 0.0 | 10.5 | 1.4 |
| 15A | Infinite Euphoria | 0.0 | 0.0 | 1.3 |
| 16A | Medihaze | 0.0 | 1.2 | 2.6 |
| 16B | Medihaze | 0.0 | 10.4 | 0.0 |
| 17B | Prize Kush | 6.2 | 0.3 | 6.6 |
| 18A | Sour Kush | 2.2 | 0.3 | 3.0 |
| 19A | Blueberry | 4.4 | 2.9 | 4.0 |

TABLE 6

Terpene content of cannabis oils

| Example | Terpene content (mg terpene per gram oil) | | | | | | |
|---|---|---|---|---|---|---|---|
| | β-myrcene | linalool | α-terpineol | β-caryophyllene | α-humulene | valencene | cis-nerolidol |
| 2-1A | 0.0 | 2.0 | 0.0 | 8.1 | 4.3 | 0.0 | 2.3 |
| 2-1B | 0.0 | 1.8 | 0.0 | 5.7 | 2.9 | 0.0 | 1.8 |
| 2-2A | 0.6 | 0.6 | 0.0 | 5.3 | 1.8 | 0.0 | 8.1 |
| 2-2B | 0.0 | 3.2 | 0.0 | 4.3 | 1.7 | 0.0 | 0.0 |
| 2-3A | 0.0 | 3.4 | 1.6 | 9.2 | 5.2 | 1.3 | 5.5 |
| 3A | 0.0 | 1.6 | 0.0 | 5.3 | 2.4 | 0.0 | 1.3 |
| 4B | 0.0 | 4.0 | 0.0 | 2.9 | 0.0 | 0.0 | 0.0 |
| 5A | 0.0 | 2.2 | 0.0 | 5.4 | 2.6 | 0.0 | 3.4 |
| 6A | 0.0 | 2.9 | 0.0 | 10.6 | 4.4 | 0.0 | 3.2 |
| 7A | 0.0 | 2.6 | 0.0 | 4.7 | 1.8 | 0.0 | 4.0 |
| 8A | 0.0 | 0.0 | 0.0 | 0.0 | 0.0 | 0.0 | 0.0 |
| 9A | 0.0 | 1.9 | 0.0 | 6.1 | 3.3 | 0.0 | 2.2 |
| 10A | 0.0 | 2.0 | 0.0 | 5.3 | 3.1 | 0.0 | 1.9 |
| 11A | 0.0 | 0.0 | 0.0 | 2.6 | 1.1 | 0.0 | 3.3 |
| 12A | 0.0 | 0.0 | 0.0 | 0.0 | 0.0 | 0.0 | 0.0 |
| 13A | 0.0 | 2.3 | 0.0 | 4.7 | 2.4 | 0.0 | 1.5 |
| 14A | 0.0 | 2.1 | 0.0 | 4.9 | 2.2 | 0.0 | 1.7 |
| 14B | 0.0 | 1.9 | 0.0 | 4.6 | 2.0 | 0.0 | 0.0 |
| 15A | 0.0 | 2.5 | 0.0 | 4.5 | 1.8 | 0.0 | 2.6 |
| 16A | 0.0 | 1.7 | 0.0 | 5.0 | 2.8 | 0.0 | 3.2 |
| 16B | 0.0 | 2.1 | 0.0 | 2.9 | 1.5 | 0.0 | 0.0 |
| 17B | 0.0 | 3.7 | 0.0 | 3.7 | 1.4 | 0.0 | 0.0 |
| 18A | 0.0 | 2.4 | 0.0 | 8.8 | 4.4 | 0.0 | 5.5 |
| 19A | 0.0 | 3.2 | 0.0 | 7.5 | 4.2 | 0.0 | 4.8 |

TABLE 7

Terpene content of cannabis oils

| Example | Terpene content (mg terpene per gram oil) | | | | | | | |
|---|---|---|---|---|---|---|---|---|
| | caryophyllene oxide | guaiol | γ-eudesmol | β-eudesmol | α-eudemsol | α-bisabolol | other terpenoids | TOTAL |
| 2-1A | 1.3 | 6.8 | 1.7 | 3.8 | 4.9 | 10.2 | 16.9 | 62.3 |
| 2-1B | 3.0 | 3.9 | 1.6 | 3.4 | 4.7 | 8.0 | 6.0 | 42.6 |
| 2-2A | 0.0 | 0.0 | 0.0 | 0.0 | 0.0 | 0.9 | 1.2 | 18.6 |
| 2-2B | 1.7 | 0.0 | 0.0 | 0.0 | 2.6 | 0.0 | 0.0 | 13.6 |
| 2-3A | 0.0 | 0.0 | 0.0 | 0.0 | 0.0 | 0.0 | 14.2 | 40.4 |
| 3A | 0.0 | 6.8 | 1.7 | 3.9 | 4.9 | 8.3 | 15.9 | 52.1 |
| 4B | 0.0 | 1.5 | 0.0 | 0.0 | 4.0 | 0.0 | 1.7 | 14.2 |
| 5A | 0.0 | 2.3 | 0.0 | 0.0 | 1.7 | 0.0 | 10.4 | 27.9 |
| 6A | 0.0 | 2.2 | 0.0 | 0.0 | 1.6 | 0.0 | 8.7 | 33.6 |
| 7A | 0.0 | 0.0 | 0.0 | 0.0 | 0.0 | 0.0 | 6.0 | 19.2 |
| 8A | 0.0 | 2.1 | 0.0 | 0.0 | 1.4 | 1.9 | 4.1 | 9.4 |

TABLE 7-continued

Terpene content of cannabis oils

Terpene content (mg terpene per gram oil)

| Example | caryophyllene oxide | guaiol | γ-eudesmol | β-eudesmol | α-eudemsol | α-bisabolol | other terpenoids | TOTAL |
|---|---|---|---|---|---|---|---|---|
| 9A | 0.0 | 0.0 | 0.0 | 0.0 | 1.7 | 0.0 | 3.2 | 18.4 |
| 10A | 0.0 | 3.1 | 0.0 | 1.4 | 2.3 | 2.6 | 9.8 | 31.6 |
| 11A | 0.0 | 0.0 | 0.0 | 0.0 | 0.0 | 1.6 | 0.0 | 8.6 |
| 12A | 0.0 | 2.1 | 0.0 | 1.5 | 2.8 | 0.0 | 2.1 | 8.5 |
| 13A | 0.0 | 2.3 | 0.0 | 0.0 | 2.0 | 2.4 | 7.6 | 25.1 |
| 14A | 0.0 | 3.2 | 0.0 | 1.6 | 1.9 | 2.5 | 9.5 | 29.6 |
| 14B | 1.8 | 2.4 | 0.0 | 0.0 | 3.2 | 2.5 | 4.1 | 22.5 |
| 15A | 0.0 | 2.5 | 0.0 | 0.0 | 2.3 | 0.0 | 6.4 | 22.6 |
| 16A | 0.0 | 2.3 | 0.0 | 0.0 | 2.1 | 1.7 | 8.6 | 27.4 |
| 16B | 0.0 | 0.0 | 0.0 | 0.0 | 3.9 | 0.0 | 1.5 | 11.9 |
| 17B | 0.0 | 0.0 | 0.0 | 0.0 | 2.1 | 0.0 | 0.0 | 10.9 |
| 18A | 0.0 | 0.0 | 0.0 | 0.0 | 0.0 | 2.2 | 7.8 | 31.0 |
| 19A | 1.7 | 0.0 | 0.0 | 0.0 | 1.5 | 0.0 | 8.9 | 31.8 |

Example 5. Activation of Cannabinoid Receptors by *Cannabis* Oils of the Invention Activation of cannabinoid receptors CNR1 (also known as CB1) and CNR2 (also known as CB2) by *cannabis* oils of the invention was characterized using a β-arrestin GPCR assay (PathHunter®, DiscoverRX) specific for either receptor. The assay is a cell-based functional assay that quantitatively measures GPCR activation through β-arrestin recruitment to activated GPCRs. GPCR activity is monitored by detecting the interaction of β-arrestin with the activated GPCR using β-galactosidase (β-gal) enzyme fragment complementation. Aspects of the assay are described, for example, in U.S. Pat. Nos. 6,342,345; 7,135,325; and 8,101,373. Activation of CNR1 and CNR2 by *cannabis* oils prepared according to the methods was observed using the β-arrestin assay, as summarized in Table 8 below.

Activation of CNR1 and CNR2 is accompanied by the release of second messenger signaling molecules including cyclic adenosine monophosphate (cAMP). CNR1 activation and CNR2 activation by *cannabis* oils of the invention were characterized using a cAMP competitive inhibition immunoassay (HitHunter®, DiscoverRX). In the assay, a fragment β-galactosidase (β-gal) enzyme donor (ED) is conjugated with cAMP, which competes with cellular cAMP (resulting from GPCR activation) for binding to an anti-cAMP antibody. When GPCR activation results in high levels of cellular cAMP, the anti-cAMP antibody becomes saturated allowing for the ED-cAMP complex to complement with the β-gal acceptor (EA). The complex forms an active enzyme that hydrolyzes a substrate to produce a chemiluminescent signal that is directly proportional to the amount of cAMP in the cells. Aspects of the assay are described, for example, in U.S. Pat. Nos. 4,708,929; 4,956,274; 5,244,785; 5,444,161; 5,604,091; and 5,643,734. Activation of CNR1 and CNR2 by *cannabis* oils prepared according to the methods was observed using the cAMP assay, as summarized in Table 8 below.

TABLE 8

GPCR Activation Activity of *Cannabis* Oils Determined by Cell-Based Assays

| Example | Strain | CNR1 cAMP EC50 (μM) | CNR1 β-Arrestin EC50 (μM) | CNR2 cAMP EC50 (μM) | CNR2 β-Arrestin EC50 (μM) |
|---|---|---|---|---|---|
| THC | Control | 0.00102 | 3.05 | 0.279 | >16.7 |
| 11-OH-THC | Control | 0.0108 | >16.7 | 0.571 | >16.7 |
| CBD | Control | >16.7 | >16.7 | >16.7 | >16.7 |
| 2-1A | AC/DC | 0.117 | >16.7 | >16.7 | >16.7 |
| 2-1B | AC/DC | 0.0791 | >16.7 | >16.7 | >16.7 |
| 2-2A | Prize Kush | 0.00661 | >16.7 | 0.245 | >16.7 |
| 2-2B | Prize Kush | 0.00572 | >16.7 | 0.199 | >16.7 |
| 2-3A | Blueberry | 0.00311 | >16.7 | 0.252 | >16.7 |
| 3A | AC/DC | 0.159 | >16.7 | >16.7 | >16.7 |
| 4B | Afghan Goo | 0.00453 | >16.7 | 0.193 | >16.7 |
| 5A | Blackberry Kush | 0.00459 | 1.63 | 0.308 | >16.7 |
| 6A | Blue Diesel | 0.00527 | >16.7 | 0.277 | >16.7 |
| 7A | Buddha Passion | 0.0114 | >16.7 | >16.7 | >16.7 |
| 8A | Cannatonic | 0.0111 | >16.7 | >16.7 | >16.7 |
| 9A | Cannatonic | 0.0133 | >16.7 | >16.7 | >16.7 |
| 10A | Cannatonic | 0.0107 | >16.7 | >16.7 | >16.7 |
| 11A | Girl Scout Cookies | 0.00582 | >16.7 | 0.190 | >16.7 |
| 12A | Harle OG | 0.0902 | >16.7 | >16.7 | >16.7 |
| 13A | Harle Tsu | 0.208 | >16.7 | >16.7 | >16.7 |
| 14A | Harlequin | 0.0245 | >16.7 | >16.7 | >16.7 |
| 14B | Harlequin | 0.0211 | >16.7 | >16.7 | >16.7 |
| 15A | Infinite Euphoria | 0.00725 | >16.7 | 0.160 | >16.7 |

TABLE 8-continued

GPCR Activation Activity of *Cannabis* Oils Determined by Cell-Based Assays

| | | CNR1 | | CNR2 | |
|---|---|---|---|---|---|
| Example | Strain | cAMP EC50 (μM) | β-Arrestin EC50 (μM) | cAMP EC50 (μM) | β-Arrestin EC50 (μM) |
| 16A | Medihaze | 0.0202 | >16.7 | >16.7 | >16.7 |
| 16B | Medihaze | 0.0248 | >16.7 | >16.7 | >16.7 |
| 17B | Prize Kush | 0.00405 | >16.7 | 0.340 | >16.7 |
| 18A | Sour Kush | 0.00374 | >16.7 | 0.185 | >16.7 |
| 19A | Blueberry | 0.00176 | 6.76 | 0.504 | >16.7 |

Example 6. Preparation of Blended Oil Compositions

*Cannabis* extracts were prepared as described above, using a *C. sativa* strain (Infinite Euphoria), *C. indica* strains (Agoo, Girl Scout Cookies), ACDC, and Blueberry. Blended oil compositions were prepared by combining the *C. sativa* preparation and/or the *C. indica* preparation(s) with the ACDC preparation and the Blueberry preparation. The cannabinoid content and the terpene content of the blended oil compositions is summarized in Table 9, Table 10, and Table 11. The extracts were weighed in a sterile glass beaker and heated on a hot plate set to 70-110° C. in order to reduce viscosity and facilitate mixing. The oil blends were stirred between 5 minutes and 30 minutes with a glass stir rod until homogenous.

TABLE 9

Blended oil composition-cannabinoid and terpene content of component extracts and blended oil composition.

| Component | *C. indica* preparation 20-1 % (w/w) | *C. sativa* preparation 20-2 % (w/w) | Blueberry preparation 20-3 % (w/w) | ACDC preparation 20-4 % (w/w) | Blended oil composition 20 % (w/w) |
|---|---|---|---|---|---|
| THC | 82.3% | 71.5% | 68.8% | 2.8% | 32.0% |
| CBD | 1.1% | 0.5% | ND | 68.7% | 41.0% |
| CBG | 2.5% | 4.9% | ND | 2.5% | 2.7% |
| CBN | 0.3% | 0.5% | 0.5% | ND | 0.5% |
| THCA | ND | 0.3% | 3.7% | ND | ND |
| CBDA | ND | ND | ND | 0.6% | 0.5% |
| CBGA | ND | ND | 0.4% | ND | 0.2% |
| total THC | 82.3% | 71.8% | 72.0% | 2.8% | 32.0% |
| total CBD | 1.1% | 0.5% | ND | 69.2% | 41.5% |
| total cannabinoids | 86.2% | 0.0% | 73.4% | 74.6% | 77.0% |
| β-caryophyllene | 0.4% | 2.3% | 0.7% | ND | 0.4% |
| α-humulene | 0.2% | 0.8% | 0.4% | ND | 0.2% |
| guaiol | 0.2% | ND | ND | 0.2% | 0.4% |
| linalool | 0.2% | 0.7% | 0.2% | 0.6% | 0.1% |
| caryophyllene oxide | ND | 0.4% | 0.2% | 0.3% | 0.1% |
| α-terpineol | ND | ND | 0.1% | ND | ND |
| endo-fenchyl alcohol | ND | ND | ND | ND | ND |
| α-bisabolol | 0.1% | ND | 0.2% | 0.3% | 0.5% |
| α-eudesmol | 0.1% | ND | 0.2% | 0.2% | 0.3% |
| β-eudesmol | 0.1% | ND | ND | 0.2% | 0.2% |
| γ-eudesmol | ND | ND | ND | 0.2% | ND |
| isoborneol | ND | ND | ND | 0.5% | 0.1% |
| unknown monoterpenes | 0.8% | ND | ND | ND | ND |
| unknown sesquiterpenes | 2.5% | ND | 1.2% | 0.1% | 1.0% |
| total terpenes | 4.6% | 4.2% | 4.0% | 2.6% | 3.4% |
| Mass | 16.46 g | 6.79 g | 6.65 g | 35.64 g | 65.64 g |

TABLE 10

THC-rich blended oil composition-cannabinoid and terpene content of component extracts and blended oil composition.

| Component | *C. indica* preparation 30-1 % (w/w) | *C. sativa* preparation 30-2 % (w/w) | Blueberry preparation 30-3 % (w/w) | ACDC preparation 30-4 % (w/w) | Blended oil composition 30 % (w/w) |
|---|---|---|---|---|---|
| THC | 82.3% | 71.5% | 68.8% | 2.3% | 61.1% |
| CBD | 1.1% | 0.5% | ND | 58.6% | 7.3% |

TABLE 10-continued

THC-rich blended oil composition-cannabinoid and terpene content of component extracts and blended oil composition.

| Component | C. indica preparation 30-1 % (w/w) | C. sativa preparation 30-2 % (w/w) | Blueberry preparation 30-3 % (w/w) | ACDC preparation 30-4 % (w/w) | Blended oil composition 30 % (w/w) |
|---|---|---|---|---|---|
| CBG | 2.5% | 4.9% | ND | 1.9% | 1.9% |
| CBN | 0.3% | 0.5% | 0.5% | ND | 0.8% |
| THCA | ND | 0.3% | 3.7% | 0.9% | 0.6% |
| CBDA | ND | ND | ND | 0.4% | 0.2% |
| CBGA | ND | ND | 0.4% | 0.3% | 0.4% |
| total THC | 82.3% | 71.8% | 72.0% | 3.3% | 61.6% |
| total CBD | 1.1% | 0.5% | ND | 59.0% | 7.5% |
| total cannabinoids | 86.2% | 0.0% | 73.4% | 0.0% | 72.2% |
| β-caryophyllene | 0.4% | 2.3% | 0.7% | 0.1% | 0.3% |
| α-humulene | 0.2% | 0.8% | 0.4% | 0.0% | 0.1% |
| guaiol | 0.2% | ND | ND | 0.0% | 0.2% |
| linalool | 0.2% | 0.7% | 0.2% | 0.1% | 0.1% |
| caryophyllene oxide | ND | 0.4% | 0.2% | ND | ND |
| α-terpineol | ND | ND | 0.1% | ND | ND |
| endo-fenchyl alcohol | ND | ND | ND | ND | ND |
| α-bisabolol | 0.1% | ND | 0.2% | ND | 0.2% |
| α-eudesmol | 0.1% | ND | 0.2% | ND | 0.2% |
| β-eudesmol | 0.1% | ND | ND | ND | ND |
| γ-eudesmol | ND | ND | ND | ND | ND |
| isoborneol | ND | ND | ND | ND | 0.1% |
| unknown monoterpenes | 0.8% | ND | ND | ND | ND |
| unknown sesquiterpenes | 2.5% | ND | 1.2% | ND | 0.5% |
| total terpenes | 4.6% | 4.2% | 4.0% | 0.4% | 1.8% |
| Mass | 52.13 g | 8.58 g | 8.58 g | 15.92 g | 85.21 g |

TABLE 11

CBD-rich blended oil composition - cannabinoid and terpene content of component extracts and blended oil composition.

| Component | C. indica preparation 40-1 % (w/w) | Blueberry preparation 40-2 % (w/w) | ACDC preparation 40-3 % (w/w) | Blended oil preparation 40 % (w/w) |
|---|---|---|---|---|
| THC | 70.0% | 68.8% | 2.6% | 11.8% |
| CBD | 0.9% | ND | 63.5% | 55.1% |
| CBG | 5.1% | ND | 2.0% | 2.7% |
| CBN | 0.3% | 0.5% | ND | 0.3% |
| THCA | 1.9% | 3.7% | ND | ND |
| CBDA | ND | ND | 1.2% | 0.7% |
| CBGA | 1.3% | 0.4% | ND | 0.2% |
| total THC | 71.7% | 72.0% | 2.6% | 11.8% |
| total CBD | 0.9% | ND | 64.5% | 55.8% |
| total cannabinoids | 79.6% | 73.4% | 69.3% | 70.8% |
| β-caryophyllene | 1.7% | 0.7% | 0.4% | 0.5% |
| α-humulene | 0.9% | 0.4% | 0.2% | 0.2% |
| guaiol | ND | ND | 0.6% | 0.4% |
| linalool | 0.2% | 0.2% | 0.1% | ND |
| caryophyllene oxide | ND | 0.2% | 0.1% | ND |
| α-terpineol | ND | 0.1% | ND | ND |
| endo-fenchyl alcohol | ND | ND | ND | ND |
| α-bisabolol | 0.2% | 0.2% | 0.7% | 0.6% |
| α-eudesmol | ND | 0.2% | ND | 0.3% |
| β-eudesmol | ND | ND | ND | 0.2% |
| γ-eudesmol | ND | ND | ND | ND |
| isoborneol | ND | ND | 0.1% | ND |
| unknown monoterpenes | ND | ND | ND | ND |
| unknown sesquiterpenes | ND | 1.2% | 2.1% | 1.2% |
| total terpenes | 3.9% | 4.0% | 4.3% | 3.5% |
| Mass | 4.96 g | 12.61 g | 107.92 g | 125.49 g |

Example 7. In Vitro Inhibition of Cancer Cell Growth Using Blended *Cannabis* Oil Compositions Brain cancer cell lines (SF-268, SF-295, SF-539, SNB-19, SNB-75, U251) and breast cancer cell lines (MCF7, BT-549, MDA-MB-231, MDA-MB-468, T-47D, HS 578T) from the NCI-60 Human Tumor Cell Lines Screen were grown for three days in the presence of blended oil compositions 20, 30, and 40 to determine the effects of the compositions on cancer cell proliferation. Blended oil compositions were tested over a range of compositions, in addition to single-strain composition 50 (containing 64.1% CBD and 2.9% THC), prepared from ACDC, and single-strain composition 60 (containing 2.42% CBD and 63.9% THC), prepared from Blueberry.

Percentage of growth inhibition was calculated using the following parameters:

$$(T_i - T_z)/(C - T_z) \times 100 \text{ when } T_i > T_z$$

$$(T_i - T_z)/T_z \times 100 \text{ when } T_i < T_z$$

$T_i$ = absorbance after drug treatment
$T_z$ = absorbance at time zero
$C$ = absorbance of control growth.

Growth inhibition resulting from treatment with the blended oil compositions and single-strain oil compositions in shown in FIGS. 4A, 5A, 6A, 7A, 8A, 9A, 10A, 11A, 12A, 13A, 14A, and 15A. Growth inhibition using mixtures of Δ9-THC and CBD having the same concentration of the oils (THC:CBD Mix 20, THC:CBD Mix 30, THC:CBD Mix 40, THC:CBD Mix 50, THC:CBD Mix 60) was also studied. See, FIGS. 4B, 5B, 6B, 7B, 8B, 9B, 10B, 11B, 12B, 13B, 14B, and 15B. In addition, growth inhibition using isolated cannabinoids (Δ8 THC, Δ9 THC, CBD, and 11Hy Δ9 THC) was examined. See, FIGS. 4C, 5C, 6C, 7C, 8C, 9C, 10C, 11C, 12C, 13C, 14C, and 15C. Oils and compound mixtures were diluted in DMSO and added to cell culture in the concentrations indicated in FIGS. 4-15. At the highest concentration of oils tested, (30 µM) the percentage of growth inhibition ranged between −40% and −80%. In the majority of experiments conducted, stronger cancer cell growth inhibition was observed for *cannabis* oil compositions than isolated cannabinoids or mixtures of isolated cannabinoids. At the highest concentration of mixed cannabinoids tested, (30 µM) the percentage of growth inhibition ranged between 20% and −50%. The results indicate that isolated cannabinoids do not provide the maximum benefit associated with plant extracts containing an entourage of cannabinoids and terpenes.

VII. Exemplary Embodiments

Exemplary embodiments provided in accordance with the presently disclosed subject matter include, but are not limited to, the claims and the following embodiments:

1. A composition comprising a first *cannabis* oil preparation having a first cannabinoid profile and a second *cannabis* oil preparation having a second cannabinoid profile.
2. The composition of embodiment 1, wherein the composition comprises Δ$^9$-tetrahydrocannabinol (THC) and (−)-cannabidiol (CBD).
3. The composition of embodiment 1 or embodiment 2, wherein the ratio of THC to CBD ranges from about 30:1 to about 1:30 by weight.
4. The composition of embodiment 3, wherein the ratio of THC to CBD is about 4:1 by weight.
5. The composition of embodiment 3, wherein the ratio of THC to CBD is about 1:1 by weight.
6. The composition of embodiment 3, wherein the ratio of THC to CBD is about 1:2 by weight.
7. The composition of embodiment 3, wherein the ratio of THC to CBD is about 1:20 by weight.
8. The composition of any one of embodiments 2-7, wherein greater than 50% of the total THC in the composition is present in the first cannabinoid profile, and greater than 50% of the total CBD in the composition is present in the second cannabinoid profile.
9. The composition of embodiment 8, wherein at least 75% of the total THC in the composition is present in the first cannabinoid profile, and at least 75% of the total CBD in the composition is present in the second cannabinoid profile.
10. The composition of any one of embodiments 2-7, further comprising a third *cannabis* oil preparation having a third cannabinoid profile.
11. The composition of embodiment 10, further comprising a fourth *cannabis* oil preparation having a fourth cannabinoid profile.
12. The composition of embodiment 11, wherein at least 50% of the total THC in the composition is present in the combined cannabinoid profile of the first *cannabis* oil preparation, the second *cannabis* oil preparation, and the third *cannabis* oil preparation, and at least 50% of the total CBD in the composition is present in the fourth cannabinoid profile.
13. The composition of embodiment 12, wherein at least 75% of the total THC in the composition is present in the combined cannabinoid profile of the first *cannabis* oil preparation, the second *cannabis* oil preparation, and the third *cannabis* oil preparation, and at least 75% of the total CBD in the composition is present in the fourth cannabinoid profile.
14. The composition of any one of embodiments 2-13, further comprising Δ$^9$-tetrahydrocannabinolic acid (THCA), cannabidiolic acid (CBDA), or a combination thereof.
15. The composition of any one of embodiments 2-14, further comprising one or more cannabinoids selected from the group consisting of cannabigerol (CBG), cannibinol (CBN), and cannabigerolic acid (CBGA).
16. The composition of embodiment 1, wherein the first *cannabis* oil preparation is prepared from the AC/DC *cannabis* strain, and wherein the second *cannabis* oil preparation is prepared from a *Cannabis sativa* strain.
17. The composition of embodiment 16, wherein the ratio of the first *cannabis* oil preparation to the second *cannabis* oil preparation is about 1:1 by weight.
18. The composition of embodiment 1, wherein the first *cannabis* oil preparation is prepared from the Medihaze *cannabis* strain, and wherein the second *cannabis* oil preparation is prepared from a *Cannabis indica* strain.
19. The composition of embodiment 18, wherein the ratio of the first *cannabis* oil preparation to the second *cannabis* oil preparation is about 1:1 by weight.
20. The composition of any one of embodiments 16-19, further comprising one or more essential oils selected from the group consisting of bergamot essential oil, blood orange essential oil, neroli essential oil, lemon essential oil, peppermint essential oil, and spearmint essential oil.
21. The composition of any one of embodiments 16-19, further comprising one or more essential oils selected from the group consisting of Sweet Orange (*Citrus sinensis* spp), Peppermint (*Mentha piperita* spp), Lemon (*Citrus limon* spp), Lavender (*Lavendula angustifolia* spp) and Vanilla (*Vanilla planifolia* spp).
22. The composition of any one of embodiments 16-19, further comprising one or more essential oils selected from lavender essential oil and lemongrass essential oil.
23. The composition of any one of embodiments 16-19, further comprising vanilla essential oil.
24. The composition of any one of embodiments 16-23, further comprising vitamin E.
25. The composition of embodiment 11, wherein the first *cannabis* oil preparation is prepared from a *Cannabis indica* strain, the second *cannabis* oil preparation is prepared from a *Cannabis sativa* strain, the third *cannabis* oil preparation is prepared from the Blueberry *cannabis* strain, and the fourth *cannabis* oil preparation is prepared from the AC/DC *cannabis* strain.
26. The composition of embodiment 25, where the ratio of the first, second, third, and fourth *cannabis* oil preparations is about 55:10:10:25 by weight.

27. The composition of embodiment 25 or embodiment 26, further comprising vitamin E.
28. A method for treating cancer, the method comprising administering a composition according to any one claims 1-27 to a subject in need thereof.

A number of embodiments have been described. Nevertheless, it will be understood that various modifications may be made without departing from the spirit and scope of the claimed invention. The flowcharts depicted in the figures do not require the particular order shown, or sequential order, to achieve desirable results. In addition, other steps may be provided, or steps may be eliminated, from the described flows, and other components may be added to, or removed from, the described composition. Accordingly, other embodiments are within the scope of the following claims.

It may be appreciated that the various method steps may be performed in any order. The steps may also be merged with each other, may perform overlapping functions, or may be coupled with other steps not shown to be connected in the figures. Accordingly, the specification, the drawings, or a combination thereof may be regarded in an illustrative rather than a restrictive sense.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A gel capsule consisting essentially of: two or more of a *cannabis sativa* oil, a *cannabis indica* oil, and a *cannabis* oil consisting essentially of 50% to 80% by weight cannabidiol and 1% to 10% by weight tetrahydrocannabinol; and two or more of bergamot essential oil, blood orange essential oil, neroli essential oil, lemon essential oil, peppermint essential oil, spearmint essential oil, lemongrass essential oil, sweet orange essential oil, lavender essential oil, and vanilla essential oil.

2. The gel capsule of claim 1, wherein the gel capsule is formulated for oral administration.

3. The gel capsule of claim 1, wherein the gel capsule is formulated for pulmonary administration.

4. A method for treating Lyme disease in a human in need thereof, the method consisting essentially of administering a therapeutically effective amount of a gel capsule of claim 1 to the human in need thereof.

* * * * *